US012799297B2

(12) United States Patent
Kim et al.

(10) Patent No.: US 12,799,297 B2
(45) Date of Patent: Nov. 17, 2026

(54) METHOD FOR PRODUCING HIGH VALUE-ADDED COMPOUNDS FROM POLYETHYLENE TEREPHTHALATE

(71) Applicants: Korea University Research and Business Foundation, Seoul (KR); EWHA UNIVERSITY—INDUSTRY COLLABORATION FOUNDATION, Seoul (KR)

(72) Inventors: Kyoung Heon Kim, Seoul (KR); Jeong Chan Joo, Seoul (KR); Hee Taek Kim, Daejeon (KR); Si Jae Park, Goyang-si (KR); Hyun Gil Cha, Ulsan (KR); Bong Keun Song, Daejeon (KR); Jae Kyun Kim, Seoul (KR)

(73) Assignees: Korea University Research and Business Foundation, Seoul (KR); EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 1256 days.

(21) Appl. No.: 17/602,574

(22) PCT Filed: Apr. 8, 2020

(86) PCT No.: PCT/KR2020/004769
§ 371 (c)(1),
(2) Date: Oct. 8, 2021

(87) PCT Pub. No.: WO2020/209607
PCT Pub. Date: Oct. 15, 2020

(65) Prior Publication Data
US 2022/0177668 A1 Jun. 9, 2022

(30) Foreign Application Priority Data
Apr. 8, 2019 (KR) ........................ 10-2019-0040992

(51) Int. Cl.
*C08J 11/14* (2006.01)
*C08G 63/183* (2006.01)
(Continued)

(52) U.S. Cl.
CPC ............. *C08J 11/14* (2013.01); *C08G 63/183* (2013.01); *C12P 7/22* (2013.01); *C12P 7/42* (2013.01);
(Continued)

(58) Field of Classification Search
CPC ......... C08J 11/14; C08G 63/183; C12P 7/22; C12P 7/42; C12P 7/44
(Continued)

(56) References Cited

U.S. PATENT DOCUMENTS

| | | | | |
|---|---|---|---|---|
| 2010/0133088 A1 | 6/2010 | Hajek et al. | | |
| 2010/0209978 A1 | 8/2010 | Shimo et al. | | |
| 2014/0120593 A1* | 5/2014 | Nukui | C12P 7/42 435/142 | |

FOREIGN PATENT DOCUMENTS

| | | | |
|---|---|---|---|
| KR | 10-2014-0033495 A | 3/2014 | |
| WO | WO-2019046946 A1 * | 3/2019 | C12N 1/20 |

OTHER PUBLICATIONS

Bradbury et al., "Glycerol as an enzyme-stabilizing agent: effects on aldehyde dehydrogenase." Proceedings of the National Academy of Sciences 69.9 (1972): 2373-2376 (Year: 1972).*
(Continued)

*Primary Examiner* — James Lin
*Assistant Examiner* — John Lee
(74) *Attorney, Agent, or Firm* — Sughrue Mion, PLLC

(57) ABSTRACT

The present invention pertains to a method for producing high value-added compounds from polyethylene terephthalate. More specifically, the present invention demonstrates that a monomeric terephthalic acid obtained from the chemi-
(Continued)

cal hydrolysis of polyethylene terephthalate can be converted to high value-added aromatic compounds and aromatic-derived compounds, and ethylene glycol, which is another monomer of polyethylene terephthalate, can be converted to glycolic acid, which is a cosmetic material. The present invention is characterized by recycling polyethylene terephthalate waste into high value-added compounds.

2 Claims, 36 Drawing Sheets

Specification includes a Sequence Listing.

(51) Int. Cl.
*C12P 7/22* (2006.01)
*C12P 7/42* (2006.01)
*C12P 7/44* (2006.01)

(52) U.S. Cl.
CPC ......... *C12P 7/44* (2013.01); *C12Y 103/01053* (2013.01); *C12Y 114/12015* (2013.01); *C12Y 401/01063* (2013.01)

(58) Field of Classification Search
USPC ..................................................... 204/157.87
See application file for complete search history.

(56) References Cited

OTHER PUBLICATIONS

Brosnan, John T., et al. "Methionine: a metabolically unique amino acid." Livestock Science 112.1-2 (2007): 2-7 (Year: 2007).*

Johnson, Christopher W., et al. "Enhancing muconic acid production from glucose and lignin-derived aromatic compounds via increased protocatechuate decarboxylase activity." Metabolic engineering communications 3 (2016): 111-119 (Year: 2016).*

Lautala et al., "Radiochemical high-performance liquid chromatographic assay for the determination of catechol O-methyltransferase activity towards various substrates." Journal of chromatography B: biomedical sciences and applications 736.1-2 (1999): 143-151 (Year: 1999).*

Wang, Jia, et al. "Microbial synthesis of pyrogallol using genetically engineered *Escherichia coli*." Metabolic Engineering 45 (2018):134-141 (Year: 2018).*

Wang, Jia, et al. "Exploring the promiscuity of phenol hydroxylase from Pseudomonas stutzeri OX1 for the biosynthesis of phenolic compounds." ACS synthetic biology 7.5 (2018): 1238-1243. (Year: 2018).*

Mikio Sasoh, et al., "Characterization of the Terephthalate Degradation Genes of *Comamonas* sp. Strain E6", Applied and Environmental Microbiology, 2006, pp. 1825-1832, vol. 72, No. 3.

Natalia Jiménez, et al., "Uncovering the Lactobacillus plantarum WCFS1 Gallate Decarboxylase Involved in Tannin Degradation", Applied and environmental microbiology, May 2013, pp. 4253-4263, vol. 79, No. 14.

Hee Taek Kim, et al., "Biological Valorization of Poly(ethylene terephthalate) Monomers for Upcycling Waste PET", ACS Sustainable Chemistry & Engineering, Nov. 12, 2019, pp. 19396-19406, vol. 7.

International Search Report for PCT/KR2020/004769 dated Jul. 14, 2020 [PCT/ISA/210].

Written Opinion for PCT/KR2020/004769 dated Jul. 14, 2020 [PCT/ISA/237].

* cited by examiner

FIG. 8A
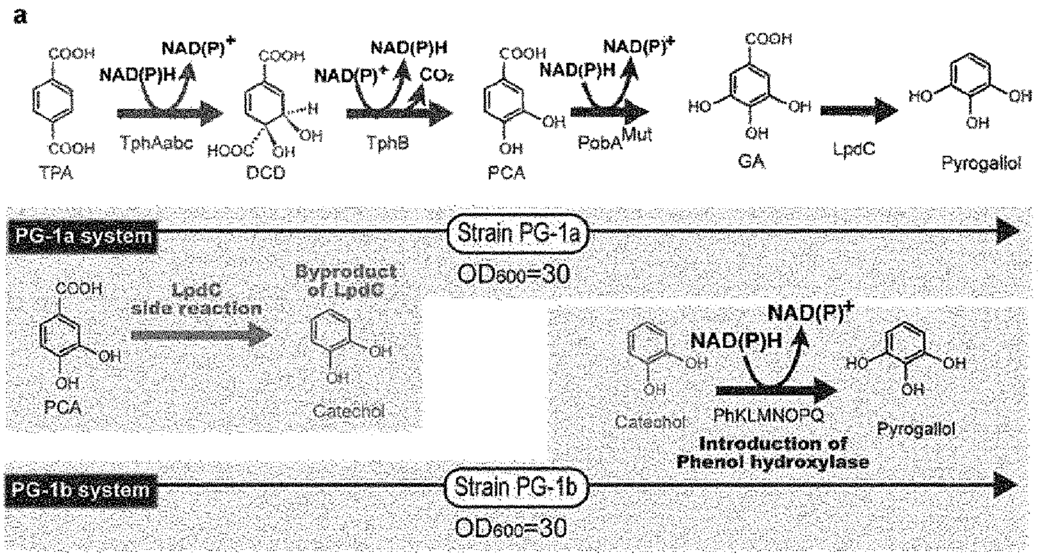
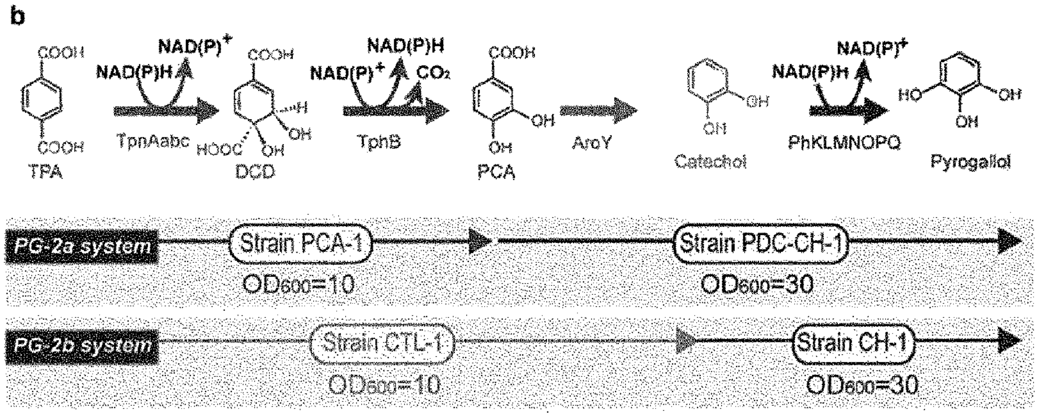
FIG. 8B
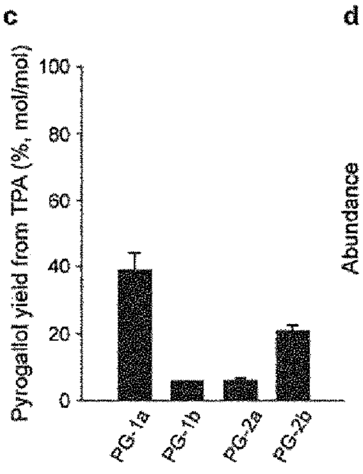
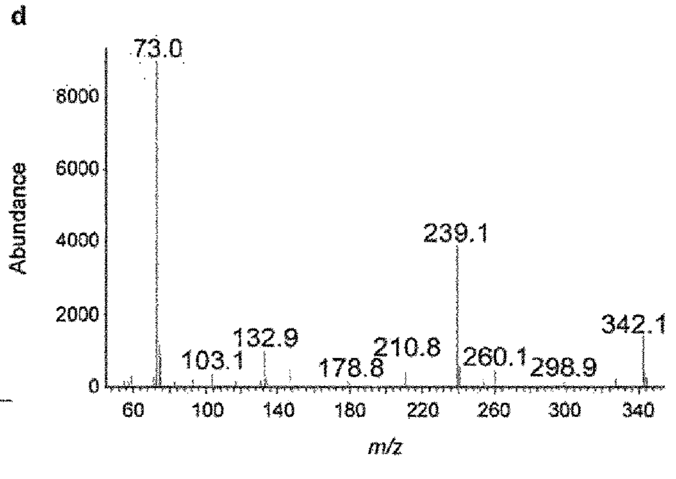
FIG. 8C
FIG. 8D

FIG. 13A
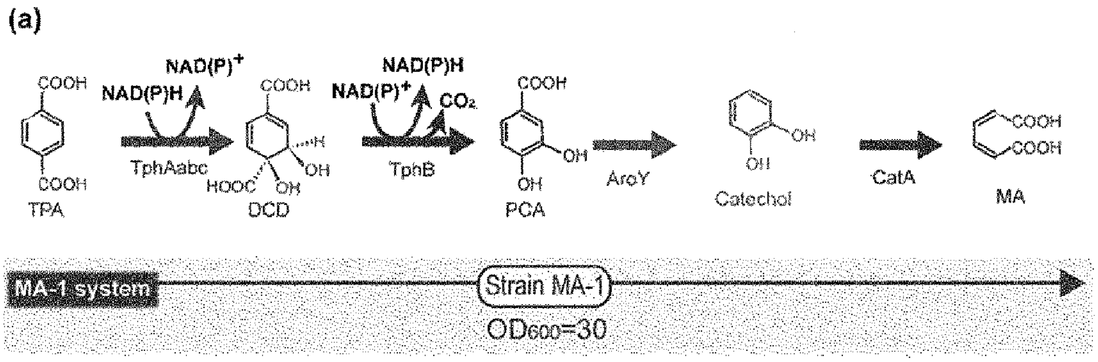
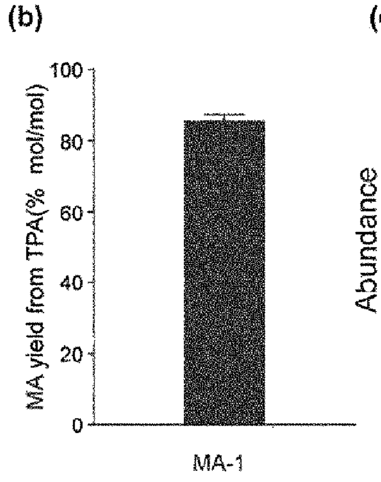
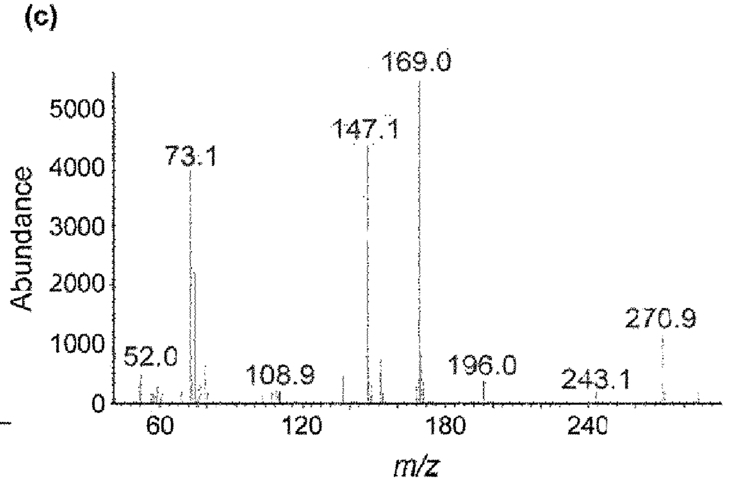
FIG. 13B
FIG. 13C

FIG. 14A
a
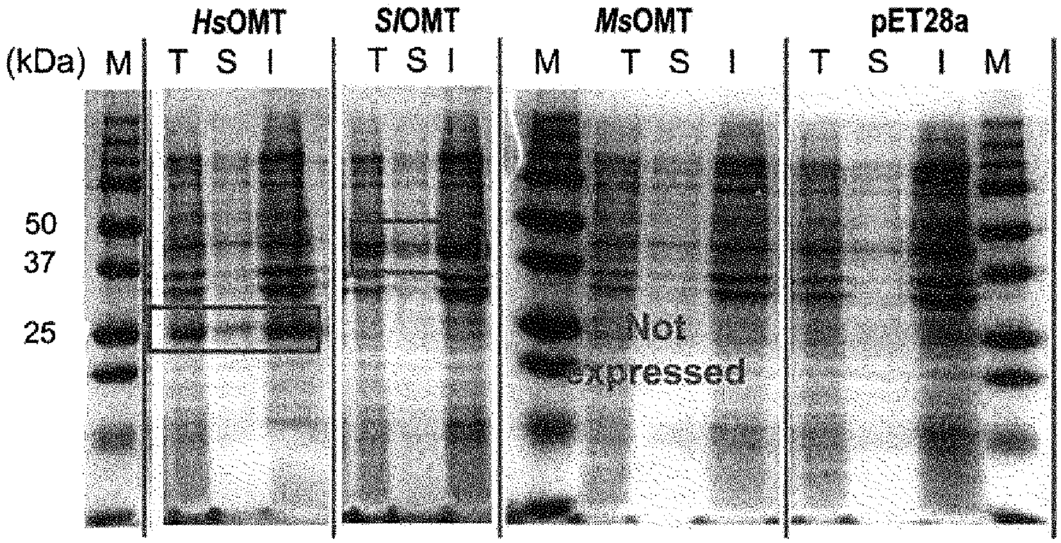
b
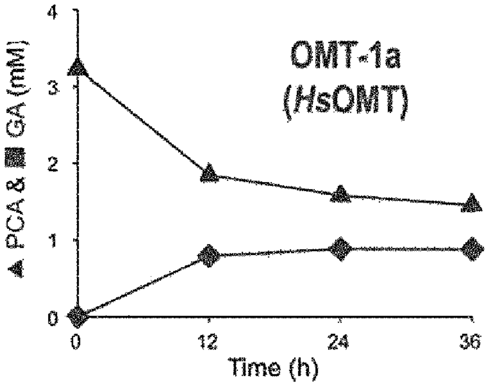
c
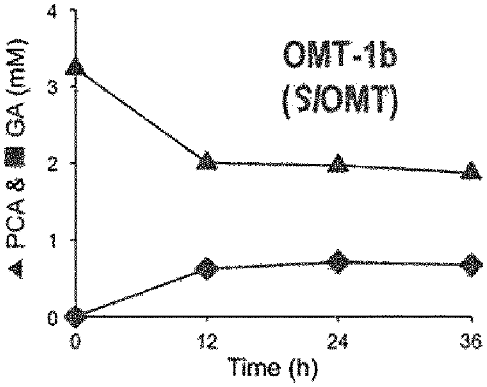
FIG 14B
FIG. 14C

FIG. 16A
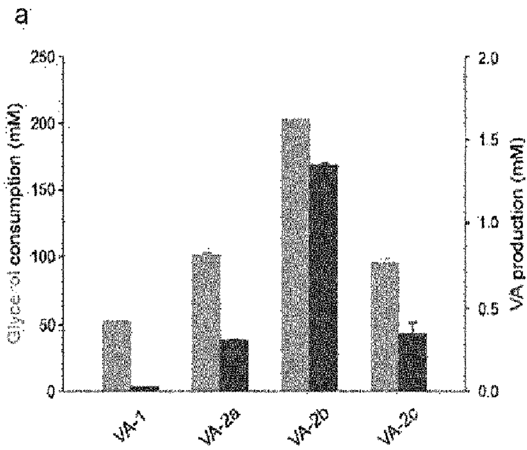
FIG. 16B
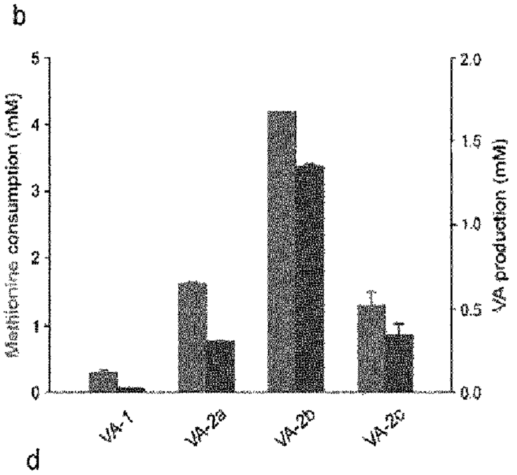
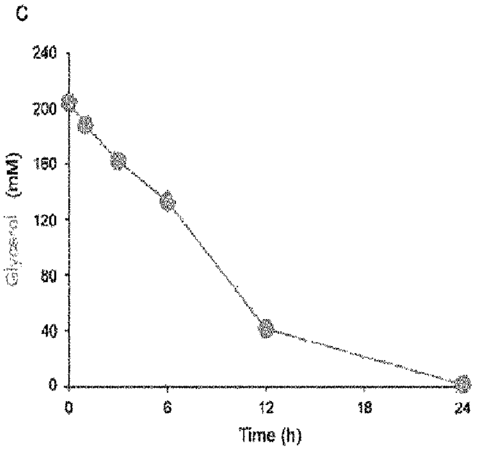
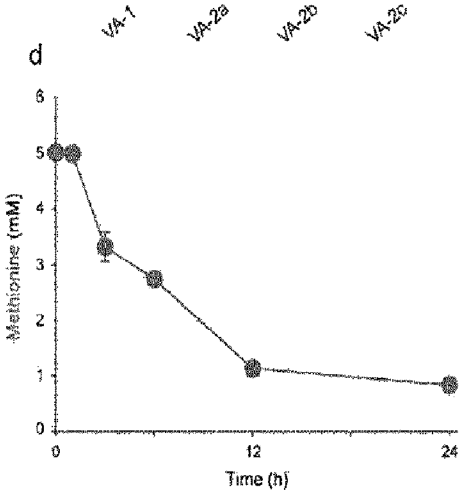
FIG. 16C
FIG. 16D

FIG. 19A
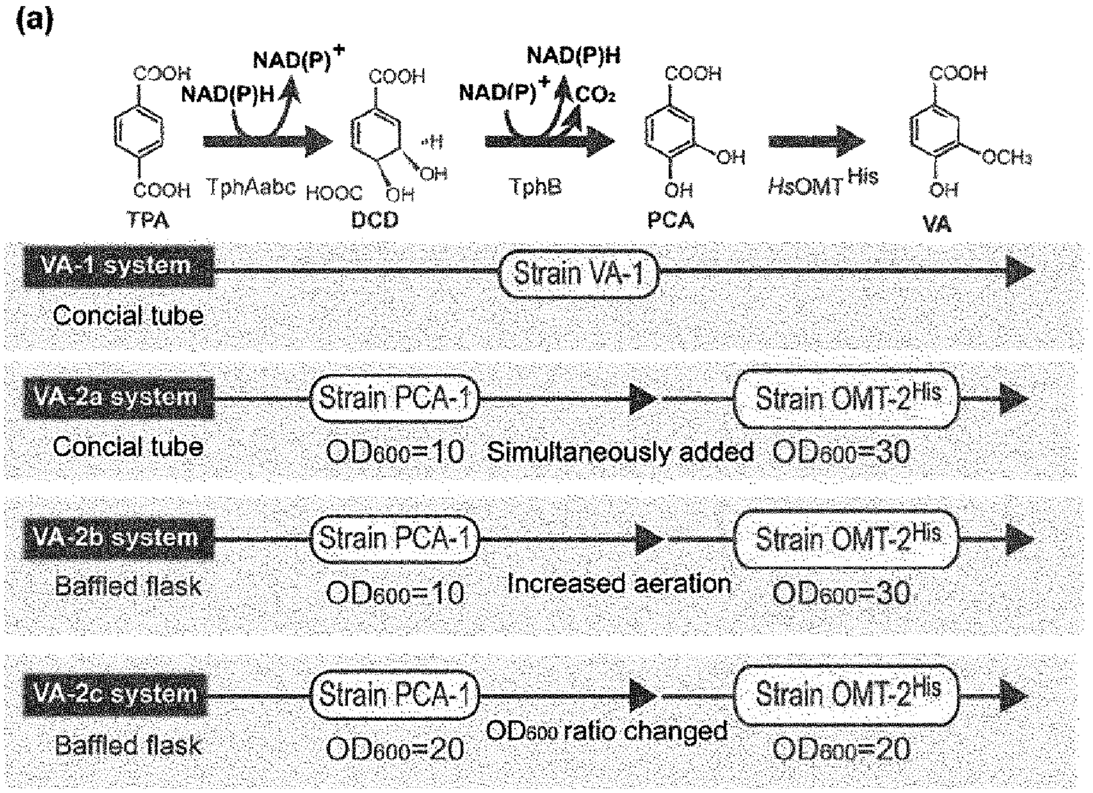
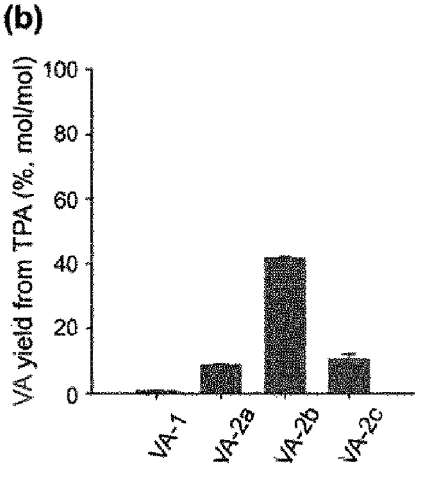
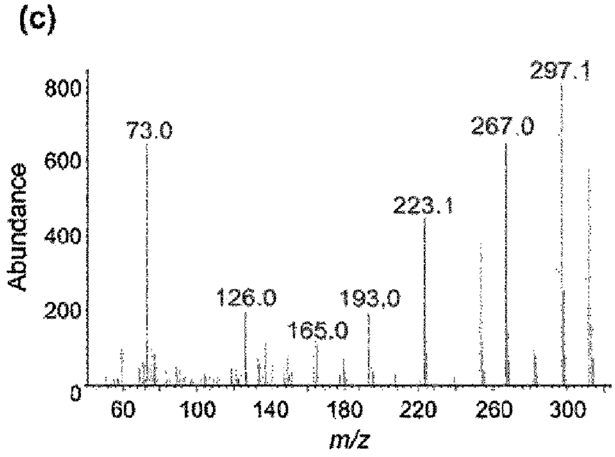
FIG. 19B
FIG. 19C

FIG. 20A
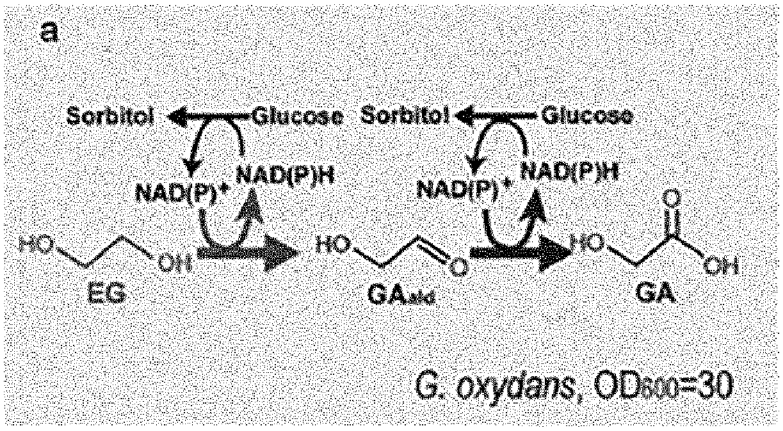
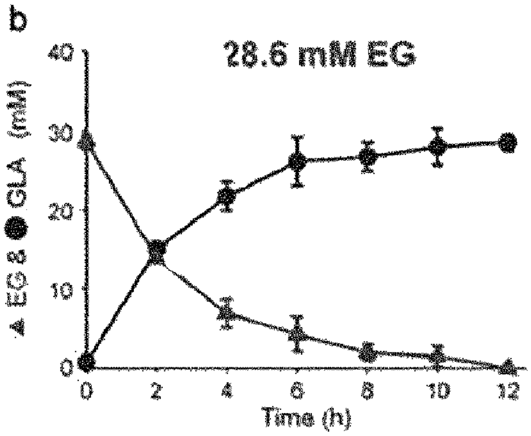
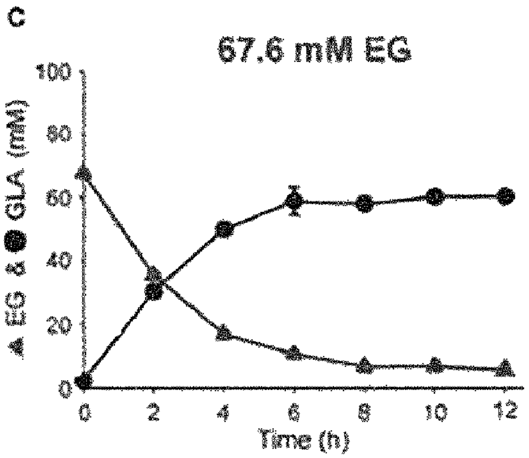
FIG. 20B
FIG. 20C

METHOD FOR PRODUCING HIGH VALUE-ADDED COMPOUNDS FROM POLYETHYLENE TEREPHTHALATE

CROSS REFERENCE TO RELATED APPLICATIONS

This application is a National Stage of International Application No. PCT/KR2020/004769 filed Apr. 8, 2020, claiming priority based on Korean Patent Application No. 10-2019-0040992 filed Apr. 8, 2019, the entire disclosures of which are incorporated herein by reference.

BACKGROUND

1. Field of the Invention

The present invention relates to a method of producing a high value-added compound from polyethylene terephthalate.

2. Discussion of Related Art

Polyethylene terephthalate (PET) is polyester of terephthalic acid (TPA) and ethylene glycol (EG). Because of its excellent physical properties, PET has been widely used in synthetic fibers and packaging materials. In 2015, annual global PET production reached 33 million tons, making PET the most commonly produced polyester in the world. Since PET does not completely decompose naturally, it causes serious environmental problems, such as the prevalence of microplastics in terrestrial ecosystems and the accumulation of waste plastics in the ocean. However, biodegradable plastics having similar physical properties and economic efficiency to PET are not yet available. Reducing PET production in the near future is unlikely, necessitating stricter PET recycling to reduce waste PET released in nature.

Among various plastics, PET and polyethylene (PE) are the only ones that are physically recyclable, and recycled plastics are produced from these waste plastics. Mechanical PET recycling has been performed for decades, but the rate of this traditional recycling is lower than approximately 21% in the United States. This low rate seems to be mainly due to the lower quality and higher costs of recycled PET (e.g., \$1.3 to 1.5/kg PET) compared to virgin PET (\$1.1 to 1.3/kg PET). To improve the high costs and low economic feasibility of mechanical recycling functioning as downcycling, for example, blending mechanically recycled PET with lignin for producing carbon fibers has been studied as an alternative application of mechanically recycled PET.

To overcome the problem of downcycling PET via mechanical recycling, chemical recycling in which PET is depolymerized into monomers and the monomers are repolymerized to PET was developed. However, PET production by the depolymerization and chemical recycling of PET also has no economic advantages. Therefore, it is necessary to improve the economic efficiency of PET recycling through upcycling by converting monomers to higher-value products than PET.

Recently, a method of chemically upcycling waste PET into high value-added plastics by the chemical modification of PET and reinforcement with glass fibers has been developed. In this case, the PET is biologically converted to plastic monomers such as polyhydroxyalkanoate (PHA). However, the economic sustainability of the bioconversion to PHA is still questionable.

Therefore, in the present invention, the biological valorization of PET monomers was verified for the first time to improve the economic efficiency of waste PET recycling and develop effective PET upcycling strategies. For the biological valorization of PET, PET was depolymerized by chemical hydrolysis and TPA and EG monomers were converted to various high value-added compounds using various metabolically engineered whole-cell microbial catalysts. In particular, by introducing a TPA degradation pathway into microbes, TPA is converted to high value-added aromatic compounds or aromatic-derived compounds, that is, protocatechuic acid (PCA), gallic acid (GA), pyrogallol, catechol, muconic acid (MA), and vanillic acid (VA), which are used for manufacturing pharmaceuticals, cosmetics, sanitizers, animal feeds, bioplastic monomers, and the like. Specifically, the present invention was completed by identifying key enzymes capable of catalyzing reactions required to convert TPA and microbes capable of fermenting EG into glycolic acid (GLA), and investigating their potential as key components of PET valorization.

SUMMARY OF THE INVENTION

The present invention is directed to providing a method of producing a high value-added compound from waste PET.

One aspect of the present invention provides a method of producing a high value-added compound from polyethylene terephthalate, comprising:

producing terephthalic acid and ethylene glycol through hydrolysis of polyethylene terephthalate; and producing one or more compounds selected from the group consisting of gallic acid, pyrogallol, catechol, muconic acid, and vanillic acid through bioconversion of the terephthalic acid in the presence of a biocatalyst, wherein protocatechuic acid is an intermediate produced by the bioconversion, or producing glycolic acid through fermentation of the ethylene glycol.

According to the present invention, by using one or a combination of the hydroxylation, decarboxylation, oxidation ring cleavage, and methylation reactions of TPA which is a PET hydrolysate, and using PCA as an intermediate, it is possible to convert PET to a variety of higher value-added compounds such as GA, pyrogallol, catechol, MA, and VA. In addition, since another PET monomer, EG, is converted to GLA using microbes capable of fermenting the same, the possibility of recycling waste PET is provided.

BRIEF DESCRIPTION OF THE DRAWINGS

FIG. 1A illustrates EG and TPA production by the chemical hydrolysis of PET and the separation of EG and TPA from the PET hydrolysate; FIG. 1B illustrates the bioconversion of TPA to PCA by *Escherichia coli* (*E. coli*) strain PCA-1; FIG. 1C illustrates the production of PCA from TPA in the PET hydrolysate by strain PCA-1; FIG. 1D is a gas chromatography-mass spectrometry (GC/MS) spectrum of PCA produced by strain PCA-1; FIG. 1E illustrates the production of GLA from EG in the PET hydrolysate by *Gluconobacter oxydans* (*G. oxydans*) KCCM 40109; FIG. 1F illustrates the time course of the whole-cell conversion of EG to GLA, wherein data is presented as the mean±standard deviation of triplicate experiments; and FIG. 1G is a GC/MS spectrum of GLA produced by *G. oxydans* KCCM 40109.

FIG. 2A illustrates EG and TPA production routes by the chemical hydrolysis of PET and the separation of TPA and EG from PET hydrolysate using NaOH and HCl; FIGS. 2B and 2C are $^1$H NMR and $^{13}$C NMR spectra of TPA from the PET hydrolysate, wherein reagent-grade TPA is used as a reference; and FIGS. 2D and 2E are $^1$H NMR and $^{13}$C NMR spectra of EG from the PET hydrolysate, wherein reagent-grade EG is used as a reference.

FIG. 5A illustrates biosynthesis routes and whole-cell catalysts for the conversion of TPA to GA; FIG. 5B illustrates the comparison of the highest GA yields from TPA in systems GA-1, GA-2a, and GA-2b, wherein data is presented as the mean±standard deviation of triplicate experiments; and FIG. 5C is a GC/MS spectrum of GA produced from TPA by the GA-2b system.

FIG. 6A illustrates the comparison of *E. coli* strain HBH-1 expressing PobA and *E. coli* strain HBH-2 strain expressing PobA$^{Mut}$ for the whole-cell conversion of PCA to GA in TG-2 buffer containing 3.4 mM PCA in conical tubes; FIG. 6B illustrates the conversion of TPA to GA by the GA-1 system consisting of *E. coli* strain GA-1 expressing TphAabc, TphB, and PobA$^{Mut}$ at $OD_{600}$=30 in TG-2 buffer containing 2.8 mM TPA in conical tubes; FIG. 6C illustrates the conversion of TPA to GA by the GA-2a system consisting of *E. coli* strain PCA-1 expressing TphAabc and TphB at $OD_{600}$=20 and strain HBH-2 expressing PobA$^{Mut}$ at $OD_{600}$=20 in TG-2 buffer containing 3.1 mM TPA in baffled flasks; and FIG. 6D illustrates the conversion of TPA to GA by a modified GA-2b system in which the cell densities of strains PCA-1 and HBH-2 of the GA-2b system were adjusted to $OD_{600}$=10 and 30, respectively, in TG-2 buffer containing 2.9 mM TPA, wherein all the conversions were performed at 30 °C and 250 rpm, and data is presented as the mean±standard deviation of triplicate experiments.

FIGS. 8A to 8D illustrate the bioconversion of TPA to pyrogallol: FIG. 8A illustrates biosynthesis routes and whole-cell catalysts for TPA conversion to pyrogallol by systems PG-1a and PG-1b; FIG. 8B illustrates biosynthesis routes and whole-cell catalysts for TPA conversion to pyrogallol by PG-2a and PG-2b; FIG. 8C illustrates the comparison of the highest pyrogallol yields from TPA of strains PG-1a and PG-1b and systems CTL-1, PG-2a, and PG-2b, wherein data is presented as the mean±standard deviation of triplicate experiments; and FIG. 8D is a GC/MS spectrum of pyrogallol produced from TPA by strain PG-1a.

FIG. 9A illustrates the conversion of TPA to pyrogallol by the PG-1a system consisting of *E. coli* strain PG-1a expressing TphAabc, TphB, PobA$^{Mut}$, and LpdC at $OD_{600}$=30; FIG. 9B illustrates the conversion of TPA to pyrogallol by the PG-1b system consisting of *E. coli* strain PG-1b expressing TphAabc, TphB, PobA$^{Mut}$, LpdC, and PhKLMNOPQ at $OD_{600}$=30; FIG. 9C illustrates the conversion of TPA to catechol by *E. coli* strain CTL-1 expressing TphAabc, TphB, and AroY at $OD_{600}$=30 in conical tubes at 30 °C and 250 rpm; FIG. 9D illustrates the conversion of TPA to pyrogallol by the PG-2a system consisting of *E. coli* strain PCA-1 expressing TphAabc and TphB at $OD_{600}$=10 and *E. coli* strain PDC-CH-1 expressing AroY and PhKLMNOPQ at $OD_{600}$=30; and FIG. 9E illustrates the conversion of TPA to pyrogallol by the PG-2b system including strain CTL-1 expressing TphAabc, TphB, and AroY at $OD_{600}$=10 and *E. coli* strain CH-1 expressing PhKLMNOPQ at $OD_{600}$=30, wherein the conversion was performed in TG-2 buffer containing 3.0 mM TPA for systems CTL-1, PG-1a, and PG-1b and 3.5 mM TPA for strains PG-1 and PG-2 in baffled flasks at 30 °C and 250 rpm, and data is presented as the mean±standard deviation of triplicate experiments.

FIG. 10A illustrates the conversion of PCA to catechol by *E. coli* strain GDC-1 expressing LpdC; and FIG. 10B illustrates the conversion of GA to catechol by strain GDC-1 expressing LpdC, wherein the conversion was performed in TG-2 buffer containing 3.0 mM PCA or 3.0 mM GA in baffled flasks at 30 °C and 250 rpm, and data is presented as the mean±standard deviation of triplicate experiments.

FIG. 11A illustrates catechol hydroxylase PhKLMNOPQ expressed in *E. coli* strain CH-1 and the production of pyrogallol from catechol; FIG. 11B illustrates PCA decarboxylase AroY expressed in *E. coli* strain PDC-1 and the production of catechol from PCA; and FIG. 11C illustrates PCA decarboxylase AroY and catechol hydroxylase PhKLMNOPQ coexpressed in *E. coli* strain PDC-CH-1 and the production of pyrogallol from PCA, wherein all the conversions were performed in TG-2 buffer in baffled flasks at 30 °C and 250 rpm, and data is presented as the mean±standard deviation of triplicate experiments.

FIG. 12A illustrates the ring cleavage of catechol by *E. coli* strain CDO-1 expressing CatA; and FIG. 12B illustrates the conversion of TPA to MA by an MA-1 system consisting of *E. coli* strain MA-1 expressing TphAabc, TphB, AroY, and CatA, wherein all the conversions were performed in TG-2 buffer at $OD_{600}$ =30 and 30 °C and 250 rpm in conical tubes, and data is presented as the mean±standard deviation of triplicate experiments.

FIGS. 13A to 13C illustrate the bioconversion of TPA to MA: FIG. 13A illustrates biosynthesis routes and whole-cell catalysts for TPA conversion to MA by *E. coli* strain MA-1 expressing TphAabc, TphB, AroY, and CatA; FIG. 13B illustrates the highest MA yields from TPA obtained in TG-2 buffer containing TPA in conical tubes at 30 °C and 250 rpm, wherein data is presented as the mean±standard deviation of triplicate experiments; and FIG. 13C is a GC/MS spectrum of MA produced from TPA by *E. coli* MA-1 strain.

FIGS. 14A to 14C illustrate the protein expression of O-methyltransferases (OMTs) from three eukaryotic sources and their whole-cell conversion of PCA to VA: FIG. 14A illustrates the results of SDS-PAGE of OMTs overexpressed in *E. coli* BL21 (DE3); FIG. 14B illustrates whole-cell conversion by *E. coli* OMT-1a expressing HsOMT at $OD_{600}$=20; and FIG. 14C illustrates whole-cell conversion by *E. coli* strain OMT-1b expressing SlOMT at $OD_{600}$=20, wherein the conversion was performed in 0.1 M sodium phosphate (pH 7.0) buffer containing 3.2 mM PCA, 10 g/L yeast extract, and 20 g/L peptone in conical tubes at 30 °C and 250 rpm, and data is presented as the mean±standard deviations of duplicate experiments. In the drawings: HsOMT, OMT from *H. sapiens;* SlOMT, OMT from *Solanum lycopersicum* (*S. lycopersicum*); MsOMT, OMT from *Medicago sativa* (*M. sativa*); pET28a, empty vector; T, total protein; S, soluble fraction; I, insoluble fraction; and M, marker.

FIG. 15A illustrates the bioconversion of TPA to VA in a VA-1 system in which *E. coli* strain VA-1 expressing TphAabc, TphB, and HsOMT at $OD_{600}$=30 was used in TG-1/YP buffer in conical tubes at 30 °C and 250 rpm; FIG. 15B illustrates the bioconversion of TPA to VA in a VA-2a system in which *E. coli* strain PCA-1 expressing TphAabc and TphB at $OD_{600}$=10 and *E. coli* strain OMT-$2^{His}$ at $OD_{600}$=30 were simultaneously added to TG-2/YPM buffer in conical tubes at 30 °C and 250 rpm; FIG. 15C illustrates the bioconversion of TPA to VA in a modified VA-2b system in which baffled flasks were used in place of the conical tubes used in the VA-2a system; and FIG. 15D illustrates the bioconversion of TPA to VA in a modified VA-2c system in which the $OD_{600}$ values for strains PCA-1 and OMT-$2^{His}$ of the VA-2b system were changed to $OD_{600}$=20 and $OD_{600}$=20, respectively, wherein data is presented as the mean±standard deviation of triplicate experiments.

FIGS. 16A to 16D illustrate glycerol and methionine consumption by various whole-cell conversion systems converting TPA to VA: FIG. 16A illustrates the comparison of glycerol consumption by systems VA-1, VA-2a, VA-2b, and VA-2c after 24 hours; FIG. 16B illustrates the comparison of methionine consumption by systems VA-1, VA-2a, VA-2b, and VA-2c after 24 hours; FIG. 16C illustrates the time course of glycerol consumption by the VA-2b system; and FIG. 16D illustrates the time course of methionine consumption by the VA-2b system, wherein glycerol and methionine were analyzed by high-performance liquid chromatography (HPLC) and GC/MS, respectively, and data is presented as the mean±standard deviation of duplicate experiments.

FIG. 17A illustrates *E. coli* strain OMT-2 expressing HsOMT in TG-1/YP buffer; and FIG. 17B illustrates *E. coli* strain OMT-$2^{His}$ expressing $HsOMT^{His}$ in TG-1/YP buffer, wherein the TG-1/YP buffer refers to 50 mM Tris-HCl buffer containing 100 g/L glycerol, 10 g/L yeast extract, and 20 g/L peptone, and whole-cell conversion was performed at $OD_{600}$=30 in 50 mL conical tubes at 30 °C and 250 rpm, and data is presented as the mean±standard deviation of triplicate experiments.

FIG. 18A illustrates *E. coli* strain OMT-$2^{His}$ in TG-2/YP buffer containing 20 g/L glycerol; and FIG. 18B illustrates strain OMT-$2^{His}$ in TG-2/YPM buffer containing 20 g/L glycerol and 2.5 mM methionine, wherein the TG-2/YP buffer refers to 50 mM Tris-HCl buffer containing 20 g/L glycerol, 10 g/L yeast extract, and 20 g/L peptone, and the TG-2/YPM buffer was modified from the TG-2/YP buffer by supplementing 2.5 mM methionine, and the conversion was performed at $OD_{600}$=30 in 50 mL conical tubes at 30 °C and 250 rpm, and data is presented as the mean±standard deviation of triplicate experiments.

FIGS. 19A to 19C illustrate the bioconversion of TPA to VA: FIG. 19A illustrates biosynthesis routes and whole-cell catalysts for the conversion of TPA to VA; FIG. 19B illustrates the comparison of the highest VA yields from TPA, wherein data is presented as the mean±standard deviation of duplicate experiments for the VA-2a system and triplicate experiments for systems VA-1, VA-2b, and VA-2c; and FIG. 19C is a GC/MS spectrum of VA produced from TPA by the VA-2b system.

FIGS. 20A to 20C illustrate the bioconversion of EG to GLA by *G. oxydans* KCCM 40109: FIG. 20A illustrates the biosynthesis route of GLA from EG; and FIGS. 20B and 20C illustrate time courses of the whole-cell conversion of EG to GLA at the initial EG of 28.6 mM (FIG. 20B) and 67.6 mM (FIG. 20C), wherein in the case of FIGS. 20B and 20C, the whole-cell conversion was performed at $OD_{600}$=30 at 30 °C and 250 rpm in conical tubes containing 40 g/L sorbitol, 10 g/L yeast extract, 2.5 g/L $(NH_4)_2SO_4$, 1 g/L $KH_2PO_4$, and 2.5 g/L $MgSO_4.7H_2O$, and data is presented as the mean±standard deviation of triplicate experiments.

DETAILED DESCRIPTION OF EXEMPLARY EMBODIMENTS

Figure 1A:
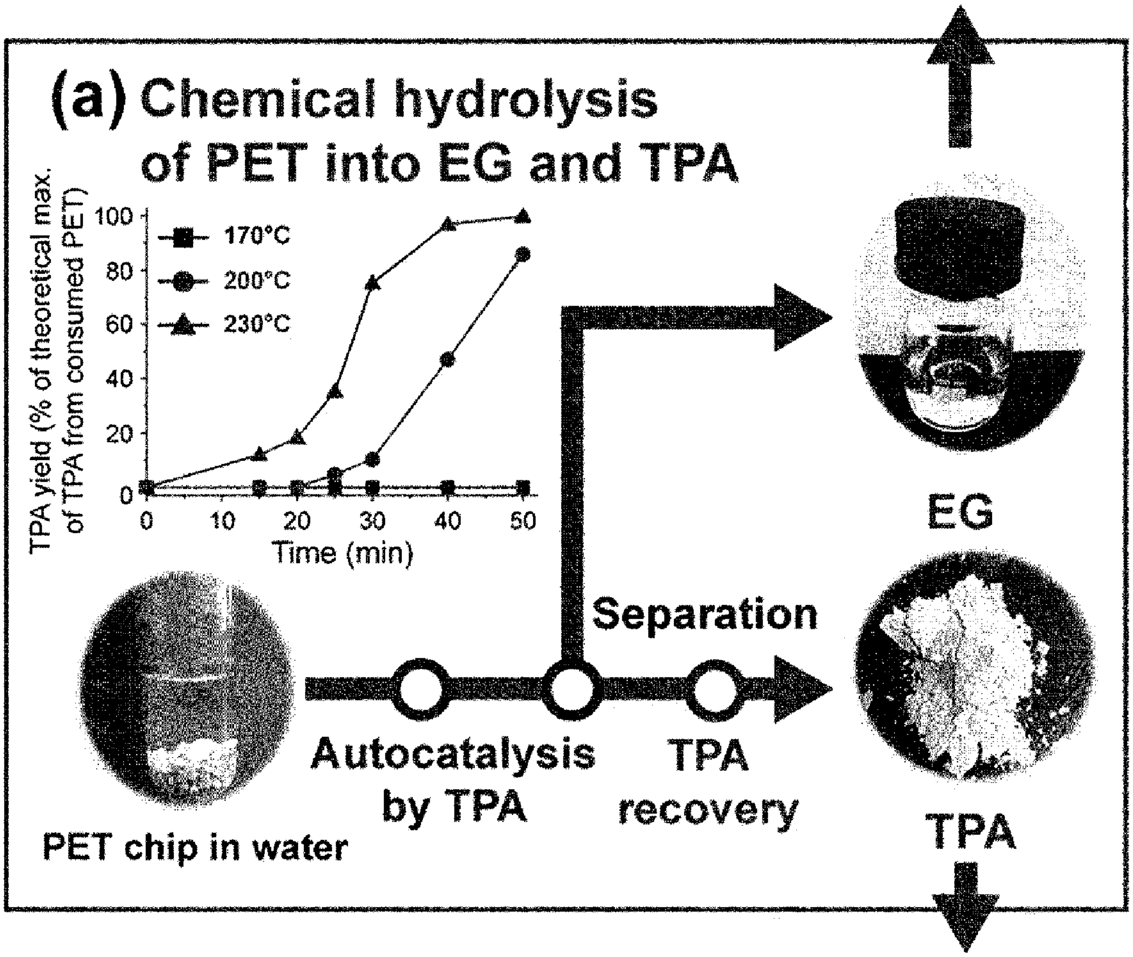
FIGS. 1A to 1G illustrate the depolymerization of PET into TPA and EG caused by the chemical hydrolysis of PET, and the bioconversion of TPA and EG in PET hydrolysate to PCA and GLA, respectively.

Hereinafter, the composition of the present invention will be described in detail.

One aspect of the present invention provides a method of producing a high value-added compound from polyethylene terephthalate, comprising:

producing terephthalic acid and ethylene glycol through hydrolysis of polyethylene terephthalate; and producing one or more compounds selected from the group consisting of gallic acid, pyrogallol, catechol, muconic acid, and vanillic acid through bioconversion of the terephthalic acid in the presence of a biocatalyst, wherein protocatechuic acid is an intermediate produced by the bioconversion, or producing glycolic acid through fermentation of the ethylene glycol.

In the method of producing a high value-added compound from polyethylene terephthalate according to the present invention, monomers terephthalic acid and ethylene glycol are produced through the chemical hydrolysis of polyethylene terephthalate, various high value-added aromatic compounds or aromatic-derived compounds such as GA, pyrogallol, catechol, MA, and VA are produced through the bioconversion of TPA which is a PET hydrolysate, and glycolic acid is produced through the fermentation of ethylene glycol.

The chemical hydrolysis of PET may be carried out through the application of microwaves at a temperature of 170 to 230 °C for 15 to 50 minutes. The PET hydrolysate may be separated into TPA solids and an EG-containing solution by filtration.

For the bioconversion of TPA, PCA is selected as a first product and a key intermediate. PCA can be a precursor compound for producing various high value-added aromatic compounds or aromatic-derived compounds such as GA, pyrogallol, catechol, MA, and VA.

As an efficient biocatalyst capable of converting TPA to PCA, TPA 1,2-dioxygenase and 1,2-dihydroxy-3,5-cyclohexadiene-1,4-dicarboxylate (DCD) dehydrogenase are used, wherein TPA 1,2-dioxygenase converts TPA to DCD, and DCD dehydrogenase converts DCD to PCA. TPA 1,2-dioxygenase and DCD dehydrogenase may be derived from *Comamonas* sp. E6, and their respective coding gene names are TphAabc and TphB. These enzymes may utilize NADH and NADPH as cofactors. According to one embodiment of the present invention, to obtain PCA from TPA, a PET hydrolysate, microbes expressing TphAabc and TphB may be used as a biocatalyst.

Next, the bioconversion of TPA to GA may be implemented by inducing hydroxylation at the meta-position of PCA, in which case, the PCA is converted to GA. The hydroxylation may be achieved using p-hydroxybenzoate hydroxylase. The p-hydroxybenzoate hydroxylase may be derived from *Pseudomonas putida* (*P. putida*) KT2440, and its coding gene name is PobA. In addition, according to one embodiment of the present invention, a PobA mutant, that is, $PobA^{Mut}$ (T294A/Y385F), may be constructed to increase GA production yield, and microbes expressing $PobA^{Mut}$ may be used as a biocatalyst. Preferably, to produce GA from TPA, microbes expressing TphAabc, TphB, and $PobA^{Mut}$ or a combination of microbes expressing TphAabc and TphB and microbes expressing $PobA^{Mut}$ may be used as a biocatalyst.

According to one embodiment of the present invention, to improve GA production yield from TPA, microbes expressing TphAabc, TphB, and $PobA^{Mut}$ (strain GA-1) and having an $OD_{600}$ value of 30 may be reacted with TPA, or microbes expressing TphAabc and TphB (strain PCA-1) and microbes expressing $PobA^{Mut}$ (strain HBH-2) and having $OD_{600}$ values of 10 and 30, respectively, may be reacted with TPA, so that the GA production yield can be improved without the accumulation of PCA.

Next, the bioconversion of TPA to pyrogallol via GA may be implemented through two routes: via the decarboxylation of GA synthesized by PCA hydroxylation (first route), and via the hydroxylation of catechol that can be synthesized by PCA decarboxylation (second route).

In the case of the first route, microbes expressing TphAabc, TphB, and $PobA^{Mut}$ due to including GA decarboxylase (coding gene name: LpdC) for the decarboxylation of GA synthesized by PCA hydroxylation may be used as a biocatalyst. According to one embodiment of the present invention, microbes expressing TphAabc, TphB, $PobA^{Mut}$, and LpdC (strain PG-1a) may be reacted with TPA to produce pyrogallol.

In the case of the second route, PCA decarboxylase (coding gene name: AroY) and a phenol hydroxylase (coding gene name: PhKLMNOPQ) for catechol hydroxylation may be used as a biocatalyst. According to one embodiment of the present invention, a combination of microbes expressing TphAabc, TphB, and AroY (strain CTL-1) and microbes expressing PhKLMNOPQ (strain CH-1), whose $OD_{600}$ values are 10 and 30, respectively, may be used and reacted with TPA, so that pyrogallol can be produced while minimizing the accumulation of catechol.

Next, the bioconversion from TPA to MA may be implemented by the ring cleavage of catechol synthesized from TPA via PCA, in which case, catechol is converted to MA. The ring cleavage of catechol may be implemented using catechol 1,2-dioxygenase (coding gene name: CatA) derived from *P. putida* KT2440. According to one embodiment of the present invention, microbes expressing TphAabc, TphB, AroY, and CatA (strain MA-1) may be reacted with TPA to produce MA.

Next, the bioconversion of TPA to VA may be implemented by converting PCA to VA by an OMT. In an O-methylation reaction catalyzed by an OMT, since adenosyl and methyl groups are supplied from ATP and methionine, S-adenosyl methionine (SAM) may be used as a co-substrate.

As the OMT, one derived from eukaryotes may be used. For example, HsOMT from *H. sapiens,* SlOMT from *S. lycopersicum,* MsOMT from *M. sativa,* and the like may be used. To increase VA production yield, HsOMT from *H. sapiens* is preferred. In addition, to increase the protein solubility of HsOMT, HsOMT may be modified to have hexameric histidine at the N-terminus.

In addition, to improve VA production yield, aeration may be increased during the reaction of TPA and a biocatalyst. Increased aeration is correlated with the increased consumption of glycerol and methionine. That is, aeration is critical for increasing VA production from PCA because glycerol is efficiently metabolized to generate adenosine triphosphate (ATP), thus accelerating S-adenosyl methionine (SAM) synthesis from methionine by supplying S-adenosyl groups.

According to one embodiment of the present invention, to produce VA from TPA via PCA, microbes expressing TphAabc and TphB (strain PCA-1) and microbes expressing $HsOMT^{His}$ (strain OMT-$2^{His}$) and having $OD_{600}$ values of 10 and 30, respectively, may be reacted with TPA in the presence of glycerol and methionine while increasing aeration to increase ATP production, and thereby VA production yield can be improved.

The method of the present invention is capable of producing GLA from EG, which is a PET hydrolysate, through fermentation. The fermentation may be performed using EG-fermenting microbes such as *G. oxydans* KCCM 40109, *Clostridium glycolicum, P. putida,* and the like.

The bioconversion of the present invention may be carried out in various reaction buffer systems. For example, the following may be used: TG-1 buffer, 50 mM Tris buffer (pH 7.0) containing 10% (w/v) glycerol; TG-2 buffer, 50 mM Tris buffer (pH 7.0) containing 2% (w/v) glycerol; TG-1/YP buffer, 50 mM Tris buffer (pH 7.0) containing 10% (w/v) glycerol, 10 g/L yeast extract, and 20 g/L peptone; TG-2/YP buffer, 50 mM Tris buffer (pH 7.0) containing 2% (w/v) glycerol, 10 g/L yeast extract, and 20 g/L peptone; TG-1/YPM buffer, TG-1/YP buffer supplemented with 2.5 mM L-methionine (Sigma-Aldrich); and TG-2/YPM buffer, TG-2/YP buffer supplemented with 2.5 mM L-methionine.

As used herein, the term "biocatalyst" refers to an enzyme involved in the bioconversion of TPA and is also used to refer to a microbe expressing the enzyme. The enzyme can be introduced into a host cell in the form of a recombinant vector containing a coding gene and expressed.

The term "recombinant vector" refers to a vector capable of expressing a target protein in an appropriate host cell and means a genetic construct including essential regulatory elements operably linked to express a gene insert in vivo or in vitro. In this specification, the terms "plasmid," "vector," and "expression vector" are used interchangeably.

Examples of the above-described vector include, but are not limited to, plasmid vectors, cosmid vectors, bacteriophage vectors, or viral vectors. Suitable expression vectors include expression control elements such as promoters, operators, start codons, stop codons, polyadenylation signals, and enhancers and additionally include signal sequences or leader sequences for membrane targeting or secretion, and they can be variously prepared according to the purpose. A promoter in a vector may be constitutive or inducible. In addition, the expression vector includes a selection marker for selecting a host cell including a vector, and in the case of a replicable expression vector, an origin of replication.

The term "operably linked" means that an appropriate nucleic acid molecule is linked to a regulatory sequence in such a way as to enable gene expression.

As used herein, the term "nucleic acid molecule" means any single or double-stranded nucleic acid molecule of cDNA, genomic DNA, synthetic DNA or RNA, PNAS or LNA origin, or a combination thereof. "Nucleic acid" and "polynucleotide" may be used interchangeably herein.

The recombinant vector of the present invention is preferably prepared by inserting the above-described gene into a general vector for expressing an *E. coli* strain. As the vector for expressing an *E. coli* strain, any commonly available *E. coli* expression vector can be used without limitation.

A host cell transformed by the recombinant vector can express an enzyme involved in the bioconversion of TPA. A method of achieving the transformation includes any method capable of introducing a nucleic acid into an organism, cell, tissue, or organ, and the transformation can be performed by selecting a standard technique suitable for the host cell, as is known in the art. Examples of such a method include, but are not limited to, electroporation, protoplast fusion, calcium phosphate ($CaPO_4$) precipitation, calcium chloride ($CaCl_2$) precipitation, agitation using silicon carbide fibers, agrobacterium-mediated transformation, and use of PEG, dextran sulfate, Lipofectamine, and the like.

In addition, since the expression level and modification of the protein are different according to the host cell, it is recommended to select and use the most suitable host cell for the purpose.

Examples of the host cell include, but are not limited to, prokaryotes such as *E. coli, Zymomonas mobilis, Bacillus subtilis, Streptomyces, Pseudomonas, Proteus mirabilis,* or *Staphylococcus*. In addition, eukaryotes such as fungi (e.g., *Aspergillus*) or yeast (e.g., *Pichiapastoris, Saccharomyces cerevisiae, Schizosaccharomyces, Neurosporacrassa*) may be used, but the present invention is not limited thereto.

Various culture methods can be applied for the (large-scale) culture of transformants, and for example, the large-scale production of expressed or overexpressed gene products from recombinant microbes can be achieved by batch or continuous culture methods. Batch and fed-batch culture methods are conventional and known in the art. Methods for controlling nutrients and growth factors for continuous culture processes and techniques for maximizing product formation rates are known in the microbial industry. In addition, as a culture medium, a medium formed of a carbon source, a nitrogen source, vitamins, and minerals may be used, and the composition of the culture medium may be configured as known in the art.

Hereinafter, the present invention will be described in more detail through Examples according to the present invention, but the scope of the present invention is not limited by the Examples presented below.

<Example 1> Bioconversion of Polyethylene Terephthalate (PET) Monomers

(1) Chemical Hydrolysis of PET

Granular PET chips (Sigma-Aldrich) were used for chemical hydrolysis experiments. PET hydrolysis reaction mixtures included 1 g granular PET in 13 mL deionized water and were input in a microwave reactor (Monowave 300, Anton Paar, Graz, Austria). PET hydrolysis was performed under microwave irradiation at various temperatures and durations: 170, 200, and 230 °C and 15, 20, 25, 30, 40, and 50 minutes. The TPA yield from hydrolysis of PET was calculated as TPA yield (% of theoretical maximum TPA=TPA produced (g)/theoretical maximum TPA produced from consumed PET (g)×100). The theoretical maximum mass of TPA to be produced from PET was calculated by multiplying PET mass by 0.864, a TPA yield coefficient for PET. Due to the high degree of polymerization of PET, the total number of cleaved ester bonds by hydrolysis was assumed to be the same as the total number of TPA and EG monomers. Therefore, the TPA yield coefficient of TPA from PET was calculated while assuming a TPA:EG:$H_2O$ molar ratio of 1:1:2. The TPA yield coefficient was 166.13/(166.13+62.06−2×18.01)=0.864, wherein 166.13, 62.06, and 18.01 are molecular weights (MWs) of TPA, EG, and $H_2O$, respectively.

(2) Separation of Monomers from PET Hydrolysate

After the chemical hydrolysis of PET, TPA solids in the hydrolysate were separated from an EG-containing solution by filtration. The TPA solids in the residue were dissolved in 1 M NaOH and thereby converted to Na-TPA. After adding 2 M HCl to the Na-TPA solution, the formed TPA solids were filtered and dried in a vacuum oven at 80 °C. The EG-containing solution was concentrated by evaporation and distilled to obtain purified EG. The TPA and EG purified from the PET hydrolysate were analyzed by nuclear magnetic resonance spectroscopy (NMR; Bruker 400 MHz, Billerica, Mass.) with $^{1}H$ NMR and $^{13}C$ NMR and compared with authentic TPA (Alfa Aesar, Haverhill, Mass.) and EG (Junsei Chemical, Tokyo, Japan) standard materials.

(3) Bacterial Strains and Plasmids

*E. coli* DH5α was used as a host strain for plasmid construction and maintenance. *E. coli* BL21 (DE3) was used as a host strain for OMT enzyme screening. *E. coli* XL1-Blue (Stratagene, San Diego, Calif.) and *E. coli* MG1655 (DE3) were used as host strains for whole-cell conversion. Recombinant *E. coli* strains were grown in lysogeny broth (LB) or on LB agar plates (2.0% w/v) containing 10 g/L tryptone, 5 g/L NaCl, and 5 g/L yeast extract. Appropriate antibiotics (50 μg/mL ampicillin, 40 μg/mL kanamycin, or 34 μg/mL chloramphenicol) were prepared and supplemented to the medium. Plasmids pKM212, pKE112, and pKA312 were constructed as described above. All plasmids and bacterial strains used in this experiment are listed in Table 1. *G. oxydans* KCCM 40109 (Korean Culture Center of Microorganisms, Seoul, Korea) was used as a whole-cell biocatalyst for the bioconversion of EG to GLA.

(4) Plasmids Construction

DNA cloning was performed per standard procedures. All genes except for pobA and catA genes were synthesized by IDT or GeneArt and extracted from *P. putida* KT2440 by polymerase chain reactions (PCR). PCR was performed using a C1000 Thermal Cycler (Bio-Rad, Hercules, Calif.). Primers and genes used for changing restriction enzyme sites are listed in Table 2 and Table 3, respectively.

For constructing plasmids pKE112TphAabc and pKM212TphB (PCA synthesis modules), plasmids pKE112 and pKM212 were digested using restriction enzymes KpnI/HindIII and EcoRI/KpnI, respectively. Corresponding TphAabc and TphB genes were digested using KpnI/HindIII and EcoRI/KpnI, respectively, and ligated into the plasmids pKE112 and pKM212.

For constructing pET28a-based plasmids for expressing genes Sl10OMT, HsOMT, MsOMT, and HsOMT$^{His}$, pET28a was digested with NdeI/XhoI, and corresponding genes were ligated. Plasmids used to directly convert TPA to PCA were constructed by ligating HsOMT and HsOMT$^{His}$ into plasmid pKE112TphB using KpnI/BamHI. To investigate the PCA hydroxylation capabilities of PobA and PobA$^{Mut}$, these genes were ligated into plasmid pET28a using NdeI/XhoI for the construction of plasmids pET28aPobA and pET28aPobA$^{Mut}$, respectively. For the direct conversion of TPA to GA, the ligation of pobA$^{Mut}$ into plasmid pKE112TphB was performed using SbfI/HindIII. For the direct conversion of TPA to PG, an lpdC gene was introduced into plasmid pKE112TphBPobA$^{Mut}$ using BamHI/SbfI. To construct catechol hydroxylation module pKA312PhKLMNOPQ, a phKLMNOPQ gene fragment was ligated into plasmids pKA312, pKA312PhKLM, pKA312PhKLMNOP, and pKA312PhKLMNOPQ using EcoRI/KpnI, KpnI/BamHI, BamHI/SbfI, and SbfI/HindII, respectively.

A plasmid for catechol synthesis was constructed by the ligation of aroY into pKE112TphB using KpnI/BamHI. For experiments related to evaluating preferred substrates of enzymes LpdC and AroY, corresponding plasmids pET28aLpdC and pET28aAroY were generated by the ligation of a corresponding enzyme into pET28a using NdeI/XhoI sites. For constructing a plasmid for MA synthesis, catA was introduced into plasmids pKE112 and pKE112TphBAroY using KpnI/BamHI sites.

(5) Whole-Cell Bioconversion

Whole-cell conversion using engineered *E. coli* strains was performed as follows. Seed cultures were prepared overnight in 5 mL LB media using appropriate antibiotics. Subsequently, seed cultures were used to inoculate 1 L LB media in 2.8 L flasks and were incubated at 37 °C and 220 rpm. When cell densities reached an optical density of 0.4 at 600 nm ($OD_{600}$), 0.1 mM isopropyl-p-D-thiogalactopyranoside (IPTG; Sigma-Aldrich, St. Louis, Mo.) was added to the cultures. Subsequently, an incubation temperature was adjusted to 16 °C for 16 hours to facilitate the soluble expression of the introduced genes. The engineered *E. coli* strains were harvested by centrifugation at 4300×g for five minutes at 10 °C. The harvested cells were washed and resuspended with 50 mM Tris buffer (pH 7.0) containing 2% (w/v) glycerol.

For whole-cell conversion, microbial cell pellets were resuspended in 4 mL or 20 mL of reaction buffer with appropriate concentrations of substrates and incubated at 250 rpm and 30 °C The compositions of reaction buffers used for bioconversion in this experiment were as follows: TG-1 buffer, 50 mM Tris buffer (pH 7.0) containing 10% (w/v) glycerol; TG-2 buffer, 50 mM Tris buffer (pH 7.0) containing 2% (w/v) glycerol; TG-1/YP buffer, 50 mM Tris buffer (pH 7.0) containing 10% (w/v) glycerol, 10 g/L yeast extract, and 20 g/L peptone; TG-2/YP buffer, 50 mM Tris buffer (pH 7.0) containing 2% (w/v) glycerol, 10 g/L yeast extract, and 20 g/L peptone; TG-1/YPM buffer, TG-1/YP buffer supplemented with 2.5 mM L-methionine (Sigma-Aldrich); and TG-2/YPM buffer, TG-2/YP buffer supplemented with 2.5 mM L-methionine. All experiments were performed in triplicate unless otherwise indicated. The whole-cell conversion using the VA-2a system was performed in duplicate. TPA, PCA, GA, pyrogallol, catechol, MA, and VA standard materials were purchased from Sigma-Aldrich.

Whole-cell bioconversion by *G. oxydans* KCCM 40109 was performed as follows. Seed cultures were prepared overnight in 5 mL media in 50 mL conical tubes. The media contained 80 g/L sorbitol, 20 g/L yeast extract, 5 g/L $(NH_4)_2SO_4$, 2 g/L $KH_2PO_4$, and 5 g/L $MgSO_4.7H_2$. The seed cultures were inoculated 1 L media in 2.8 L flasks and were incubated at 30 °C and 220 rpm. The cells were collected by centrifugation at 6500×g for eight minutes at 10 °C and were washed and resuspended in phosphate buffer (pH 7.0). Whole-cell bioconversion mixtures were prepared by appropriate resuspending concentrations of whole-cell catalysts in 4 or 20 mL buffers and were incubated at 30 °C and 250 rpm for 12 hours. Bioconversion buffers were composed of 40 g/L sorbitol, 10 g/L yeast extract, 2.5 g/L $(NH_4)_2SO_4$, 1 g/L $KH_2PO_4$, and 2.5 g/L $MgSO_4.7H_2O$. The bioconversion buffers were supplemented with EG at different concentrations: 11.3, 28.6, and 67.6 mM.

(6) SDS-PAGE Analysis

The expression of eukaryotic OMT enzymes SlOMT, HsOMT, and MsOMT in *E. coli* BL21 (DE3) cells was verified using sodium dodecyl sulfate-polyacrylamide gel electrophoresis (SDS-PAGE). Recombinant *E. coli* BL21 (DE3) cells harboring the respective plasmids were cultivated in 100 mL LB media in 500 mL flasks at 37 °C and 220 rpm. The cultures were supplemented with 0.1 mM IPTG upon reaching an $OD_{600}$ of 0.4 and were cultivated for 16 hours at 16 °C and 180 rpm. Cell pellets were collected by centrifugation at 6,500×g for 10 minutes at 4 °C and washed with 16 mL of 100 mM sodium phosphate buffer (pH 7.0).

Aliquots were prepared from the cell suspension and were used as total protein samples for SDS-PAGE. Cell lysates of recombinant *E. coli* were obtained by sonication (Branson 450, Marshall Scientific, Hampton, NH). Solid and liquid fractions containing insoluble and soluble proteins, respectively, were separated by centrifugation at 16,000×g for 20 minutes at 4 °C The separated solid fraction was resuspended in 16 mL of 100 mM sodium phosphate buffer (pH 7.0). The aliquoted cell suspension and the liquid and solid fractions were mixed with 5×SDS buffer (Biosesang, Seongnam, Korea) and boiled at 100 °C for 10 minutes. Protein samples were separated by 12% (w/v) SDS-PAGE with a pre-stained SDS standard marker (Bio-Rad).

(7) Analytical Methods

The $OD_{600}$ was measured using a spectrophotometer (xMark™, Bio-Rad). TPA and products converted from TPA were analyzed using HPLC (Agilent 1100, Agilent Technologies, Santa Clara, CA) equipped with an OptimaPak C18 column (RS tech, Daejeon, Korea) at a flow rate of 1.0 mL/min while maintaining a column temperature at 30 °C A mobile phase was composed of 10% (v/v) acetonitrile in 0.1% (v/v) trifluoroacetic acid (Sigma-Aldrich) in deionized water. The injection volume was 5 μL, and UV detection was performed at 254 nm. Concentrations of EG, GLA, and glycerol were measured by HPLC (Agilent 1100) equipped with a refractive index (RI) detector and an Aminex HPX-87H column (Bio-Rad) at 65 °C with a 0.01 N $H_2SO_4$ mobile phase at a flow rate of 0.5 mL/min.

GC/MS analysis was used to verify the conversion of TPA to PCA, GA, pyrogallol, catechol, MA, and VA and the conversion of EG to GLA and quantify L-methionine. The GC/MS analysis was performed using Agilent 7890A GC/5975C MSD (Agilent Technologies) equipped with an RTX-5Sil MS capillary column (30 m×0.25 mm, 0.25 μm film thickness; Restek, Bellefonte, PA) with an additional 10 m integrated guard column. One microliter of a sample was injected in a splitless mode with an inlet temperature of 250 °C. The oven temperature was initially maintained at 50°C for one minute and then increased to 320 °C at a rate of 20 °C/min and then maintained for 25 minutes. Helium was used as a carrier gas at a 1 mL/min flow rate, and mass spectra were recorded by scanning from 50 to 700 m/z. Temperatures of a transfer line and an ion source were set at 280 and 230 °C, respectively.

(8) Computer Docking Simulation

The computational modeling of a protein structure PobA derived from *P. putida* KT2440 was performed using the Discovery Studio software (BIOVIA, San Diego, CA). The FAD-bound structure of PobA (PDB code: 6DLL) was used in computational docking simulations. A wild-type PobA structure does not have 4-hydroxybenzoic acid (4-HBA) in its active site, indicating that the crystal structure of wild-type PobA may not represent the complex conformation of 4-HBA and FAD. For the docking simulations, the binding conformation of FAD in the active site of *P. putida* KT2440 PobA was modeled using MODELER by comparing its active site with that of *Pseudomonas fluorescence* PobA complexed with 4-HBA and FAD (PDB codes: 1PBE and 1BGN). The structure of PobA$^{Mut}$ (T294A/Y385F) was constructed by MODELER. The flexible docking of substrate PCA was performed using AutodockFR, and nine residues (Y386, Y201, T294, L210, S212, R220, W185, Y222, and I43) were selected as flexible residues. All parameters were set at default values for docking simulations, and the resulting binding mode was analyzed using the PyMOL software (PyMOL Molecular Graphics System, ver. 1.4.1; Schrodinger, New York, NY).

TABLE 1

Strains, strategies, and plasmids used in present invention

| Strain, strategy, or plasmid | Relevant characteristics | Reference |
|---|---|---|
| Strains | | |
| *E. coli* XL1-Blue | recA1 endA1 gyrA96 thi-1 hsdR17 supE44 relA1 lac [F′proAB lacI$^q$ZΔM15 Tn10 (Tet$^R$)] | Stratagene |
| *E. coli* MG1655 (DE3) | K-12 F$^-$ λ$^-$ ilvG$^-$ rfb-50 rph$^{-1}$ (DE3) | Korea Research Institute of Bioscience & Biotechnology |
| *G. oxydans* KCCM 40109 | GLA produced from EG | KCCM |
| | Recombinant strain for PCA synthesis | |
| PCA-1 (TPA→PCA) | *E. coli* XL1-Blue with pKM212TphAabc and pKE112TphB | Present invention |
| | Recombinant strains for GA synthesis | |
| HBH-1 (PCA→GA) | *E. coli* MG1655 (DE3) with pET28aPobA | Present invention |
| HBH-29 (PCA→GA) | *E. coli* MG1655 (DE3) with pET28aPobA$^{Mut}$ | Present invention |
| GA-1 (TPA→GA) | *E. coli* XL1-Blue with pKM212TphAabc and pKE112TphBPobA$^{Mut}$ | Present invention |
| | Recombinant strains for pyrogallol synthesis | |
| GDC-1 (GA→pyrogallol) | *E. coli* MG1655 (DE3) with pET28aLpdC | Present invention |
| CH-1 (catechol→pyrogallol) | *E. coli* MG1655 (DE3) with pKA312PhKLMNOPQ | Present invention |
| PDC-CH-1 (PCA→pyrogallol) | *E. coli* MG1655 (DE3) with pET28aAroY and pKA312PhKLMNOPQ | Present invention |
| PG-1 (TPA→pyrogallol) | *E. coli* XL1-Blue with pKM212TphAabc and pKE112TphBLpdCPobA$^{Mut}$ | Present invention |
| PG-2 (TPA→pyrogallol) | *E. coli* XL1-Blue with pKM212TphAabc, pKE112TphBLpdCPobA$^{Mut}$ and pKA312PhKLMNOPQ | Present invention |
| | Recombinant strains for catechol synthesis | |
| PDC-1 (PCA→catechol) | *E. coli* MG1655 (DE3) with pET28aAroY | Present invention |
| CTL-1 (TPA→catechol) | *E. coli* XL1-Blue with pKM212TphAabc and pKE112TphBaroY | Present invention |
| | Recombinant strains for MA synthesis | |
| CDO-1 (catechol→MA) | *E. coli* XL1-Blue with pKE112CatA | Present invention |
| MA-1 (TPA→MA) | *E. coli* XL1-Blue with pKM212TphAabc and pKE112TphBAroYCatA | Present invention |
| | Recombinant strains for VA synthesis | |
| OMT-1a (PCA→VA) | *E. coli* BL21 (DE3) with pET28aHsOMT | Present invention |
| OMT-1b (PCA→VA) | *E. coli* BL21 (DE3) with pET28aSlOMT | Present invention |
| OMT-2 (PCA→VA) | *E. coli* MG1655 (DE3) with pET28aHsOMT | Present invention |
| OMT-2$^{His}$ (PCA→VA) | *E. coli* MG1655 (DE3) with pET28aHsOMT$^{His}$ | Present invention |
| VA-1 (TPA→VA) | *E. coli* XL1-Blue with pKM212TphAabc and pKE112TphBHsOMT | Present invention |
| Whole-cell conversion systems | | |
| GA-1 system | Strain GA-1 as a single catalyst under increased aeration ($OD_{600}$ of strain GA-1 = 30) | Present invention |
| GA-2a system | Simultaneous addition of strains PCA-1 and HBH-2 under increased aeration ($OD_{600}$ of strain PCA-1 = 20, $OD_{600}$ of strain HBH-2 = 20) | Present invention |

TABLE 1-continued

Strains, strategies, and plasmids used in present invention

| Strain, strategy, or plasmid | Relevant characteristics | Reference |
|---|---|---|
| GA-2b system | Simultaneous addition of strains PCA-1 and HBH-2 under increased aeration ($OD_{600}$ of PCA-1 strain = 10, $OD_{600}$ of HBH-2 strain = 30) | Present invention |
| PG-1a system | Strain PG-1a as a single catalyst under increased aeration ($OD_{600}$ of strain PG-1a strain = 30) | Present invention |
| PG-1b system | Strain PG-1b as a single catalyst under increased aeration ($OD_{600}$ of strain PG-1b = 30) | Present invention |
| PG-2a system | Simultaneous addition of strains PCA-1 and PDC-CH-1 under increased aeration ($OD_{600}$ of strain PCA-1 = 10, $OD_{600}$ of strain PDC-CH-1 = 30) | Present invention |
| PG-2b system | Simultaneous addition of strains CTL-1 and CH-1 under increased aeration ($OD_{600}$ of strain CTL-1 = 10, $OD_{600}$ of strain CH-1 = 30) | Present invention |
| MA-1 system | Strain MA-1 as a single catalyst ($OD_{600}$ of strain MA-1 = 30) | Present invention |
| VA-1 system | Strain VA-1 as a single catalyst ($OD_{600}$ of strain VA-1 = 30) | Present invention |
| VA-2a system | Simultaneous addition of strains PCA-1 and OMT-$2^{His}$ ($OD_{600}$ of strain PCA-1 = 10, $OD_{600}$ of strain OMT-$2^{His}$ = 30) | Present invention |
| VA-2b system | Simultaneous addition of strains PCA-1 and OMT-$2^{His}$ under increased aeration ($OD_{600}$ of strain PCA-1 = 10, $OD_{600}$ of strain OMT-2 = 30) | Present invention |
| VA-2c system | Simultaneous addition of strains PCA-1 and OMT-$2^{His}$ under increased aeration ($OD_{600}$ of strain PCA-1 = 20, $OD_{600}$ of strain OMT-$2^{His}$ = 20) | Present invention |
| Plasmids | | |
| pKM212TphAabc | pKM212; $P_{tac}$ promoter, *Comamonas* sp. strain E6 tphAIIabc genes, $Km^R$ | Present invention |
| pKE112TphB | pKE112; $P_{tac}$ promoter, *Comamonas* sp. strain E6 tphB gene, $Amp^R$ | Present invention |
| pET28aHsOMT | pET28a; T7 promoter, *H. sapiens* OMT gene, $Km^R$ | Present invention |
| pET28aSlOMT | pET28a; T7 promoter, *S. lycopersicum* OMT gene, $Km^R$ | Present invention |
| pET28aMsOMT | pET28a; T7 promoter, *M. sativa* OMT gene, $Km^R$ | Present invention |
| pET28aHsOMT$^{His}$ | pET28a; T7 promoter, H. sapiens OMT' gene, $Km^R$ | Present invention |
| pKE112TphBHsOMT | pKE112; $P_{tac}$ promoter, OMT gene of *H. sapiens* inserted into pKE112TphB, $Amp^R$ | Present invention |
| pKE112TphBPobA$^{Mut}$ | pKE112; $P_{tac}$ promoter, pobA$^{Mut}$ gene of *P. putida* KT2440 inserted into pKE112TphB, $Amp^R$ | Present invention |
| pET28aPobA | pET28a; T7 promoter, *P. putida* KT2440pobA gene, $Km^R$ | Present invention |
| pET28aPobAm' | pET28a; T7 promoter, *P. putida* KT2440pobA$^{Mut}$ gene, $Km^R$ | Present invention |
| pET28aAroY | pET28a; T7 promoter, *E. cloacae* aroY gene, $Km^R$ | Present invention |
| pET28aLpdC | pET28a; T7 promoter, *L. plantarum* lpdC gene, $Km^R$ | Present invention |
| pKE112TphBaroY | pKE112; $P_{tac}$ promoter, aroY gene of *E. cloacae* inserted into pKE112TphB, $Amp^R$ | Present invention |
| pKE112TphBAroYCatA | pKE112; $P_{tac}$ promoter, catA gene of *P. putida* KT2440 inserted into pKE112TphBAroY, $Amp^R$ | Present invention |
| pKE112TphBPobA$^{Mut}$LpdC | pKE112; $P_{tac}$ promoter, lpdC gene of *L. plantarum* inserted into pKE112TphBPobA$^{Mut}$, $Amp^R$ | Present invention |
| pKA312PhKLMNOPQ | pKE112; $P_{tac}$ promoter, PhKLMNOPQ gene of *P. stutzeri* OX1, $Cm^R$ | Present invention |
| pKE112CatA | pKE112; $P_{tac}$ promoter, catA gene of *P. putida* KT2440, $Amp^R$ | Present invention |

TABLE 2

Primers used in present invention

| Primer name | Sequence (5'-3') | SEQ ID NO: | Gene source |
|---|---|---|---|
| pKM212-TphAabc-F/R | Gene synthesis at IDT | | *Comamonas* sp. strain E6 |
| pKE112-TphB-F/R | Gene synthesis at IDT | | *Comamonas* sp. strain E6 |
| pET28a-HsOMT | Gene synthesis at IDT | | *H. sapiens* |
| pET28a-SlOMT | Gene synthesis at IDT | | *S. lycopersicum* |
| pET28a-MsOMT | Gene synthesis at IDT | | *M. sativa* |
| pKE112-HsOMT-F | GGTACCTTTCACACAGGAAACAGACCATGGGCGATACCAAAG AACAG | 20 | pET28a-HsOMT |

TABLE 2-continued

| Primer name | Sequence (5'-3') | SEQ ID NO: | Gene source |
|---|---|---|---|
| Primers used in present invention | | | |
| pKE112-HsOMT-R | GGATCC TTAAGTTACGGACCTGCTTCG | 21 | |
| pKE112-HsOMT$^{His}$-F | GGTACC TTTCACACAGGAAACAGACCATGCATCACCATCACCATCATGG CGATACCAAAGAACAGCG | 22 | pET28a-HsOMT |
| pKE112-HsOMT$^{His}$-R | Same as that of HsOMT-R (GGATCC TTAAGTTACGGACCTGCTTCG) | 23 | |
| pET28a- HsOMT$^{His}$-F | CATATG CATCACCATCACCATCATGGCGATACCAAAGAACAGCG | 24 | pET28a-HsOMT |
| pET28a-HsOMT$^{His}$-R | CTCGAG TTAAGTTACGGACCTGCTTCG | 25 | |
| pET28a-PobA-F | CATATG AAAACTCAGGTTGCAATTATTG | 26 | *P. putida* KT2440 |
| pET28a-PobA-R | CTCGAG TCAGGCAACTTCCTCGAACG | 27 | |
| pKE112-PobA-F | CCTGCAGG TTTCACACAGGAAACAGACC ATGAAAACTCAGGTTGCAATTATTG | 28 | *P. putida* KT2440 |
| pKE112-PobA-R | AAGCTT TCAGGCAACTTCCTCGAACG | 29 | |
| pKE112-PobA$^{Mut}$-F/R | Gene synthesis at IDT | | Mutant of *P. putida* KT2440 pobA gene |
| pET28a-PobA$^{Mut}$-F | Same as that of pET28a-PobA-F | 26 | pKE112-PobA$^{Mut}$-F/R |
| pET28a-PobA$^{Mut}$-R | Same as that of pET28a-PobA-R | 27 | |
| pKE112-LpdC-F/R | Gene synthesis at Gene Art | | *P. putida* KT2440 |
| pET28a-LpdC-F | CATATG GCAGAACAACCATGGGATT | 30 | pKE112-LpdC-FIR |
| pET28a-LpdC-R | CTCGAG TTACTTCAAATACTTCTCCCAGTC | 31 | |
| pKE112-AroY-F/R | Gene synthesis at Gene Art | | *L. plantarum* WCFS1 |
| pET28a-AroY-F | CATATG CAGAACCCGATCAACGAC | 32 | pKE112-AroY-F/R |
| pET28a-AroY-R | CTCGAG TTACTTCTTGTCGCTGAACAGC | 33 | |
| pKA312-PhKLMOPQ-F/R | Gene synthesis at Gene Art | | *P. stutzeri* OX1 |
| pKE112-CatA-F | GGTACCTTTCACACAGGAAACAGACC ATGACCGTGAAAATTTCCCACAC | 34 | *P. putida* KT2440 |
| pKE112-CatA-R | GGATCC TCAGCCCTCCTGCAACGC | 35 | |

TABLE 3

| Gene | UniProtKB Accession Number | Sequence (5'-3') | SEQ ID NO: |
|---|---|---|---|
| Nucleic acid sequences of genes used in present invention | | | |
| tphAa | Q3C1D2 | ATGAACCACCAGATCCATATCCACGACTCCGATATCGCGTTCCCCTGCGC GCCCGGGCAATCCGTACTGGATGCAGCTCTGCAGGCCGGCATCGAGCTG CCCTATTCCTGCCGCAAAGGTAGCTGTGGCAACTGTGCGAGTACGCTGC TCGACGGAAATATTGCCTCCTTCAATGGCATGGCCGTGCGAAACGAACT CTGCGCCTCGGAACAAGTGCTGCTGTGCGGCTGCACTGCAGCCAGCGAT ATACGTATCCACCCGAGCTCCTTTCGCCGTCTCGACCCGGAAGCCCGAA AACGTTTTACGGCCAAGGTGTACAGCAATACACTGGCGGCACCCGATGT CTCGCTGCTGCGCCTGCGCCTGCCTGTGGGCAAGCGCGCCAAATTTGAA GCCGGCCAATACCTGCTGATTCACCTCGACGACGGGGAAAGCCGCAGCT ACTCTATGGCCAATCCACCCCATGAGAGCGATGGCATCACATTGCATGTC AGGCATGTACCTGGTGGTCGCTTCAGCACTATCGTTCAGCAGTTGAAGT CTGGTGACACATTGGATATCGAACTGCCATTCGGCAGCATCGCACTGAA | 1 |

TABLE 3-continued

| Gene | UniProtKB Accession Number | Sequence (5'-3') | SEQ ID NO: |
|---|---|---|---|
| | | Nucleic acid sequences of genes used in present invention | |
| | | GCCTGATGACGCAAGGCCCCTGATTTGCGTTGCGGGTGGCACGGGATTT GCGCCCATTAAATCCGTTCTTGATGACTTAGCCAAACGCAAGGTTCAGC GCGACATCACGCTGATCTGGGGGCTCGCAACCCCTCGGGCCTGTATCT TCCTAGCGCCATCGACAAGTGGCGCAAAGTCTGGCCACAGTTTCGCTAC ATTGCAGCCATCACCGACCTAGGCGATATGCCTGCGGATGCTCACGCAG GTCGGGTGGATGACGCGCTACGCACTCACTTTGGCAACCTGCACGATCA TGTGGTGCACTGCTGTGGCTCACCAGCTCTGGTTCAATCAGTGCGCACA GCCGCTTCCGATATGGGCCTGCTTGCACAGGACTTCCACGCGGATGTTTT TGCGACAGGCCCGACTGGTCACCACTAG | |
| tphAb | Q3C1D5 | AACAGGCCAACCTTATCGGCCCGGCCGGATTCATTTCCATGGAAGACG GAGCTGTCGGTGGATTCGTGCAGCGTGGCATCGCAGGCGCTGCCAACC TTGATGCAGTCATCGAGATGGGCGGAGACCACGAAGGCTCTAGCGAGG GCCGCGCCACGGAAACCTCGGTACGCGGCTTTTGGAAGGCCTACCGCA AGCATATGGGACAGGAGATGCAAGCATGA | 2 |
| tphAc | Q3C1D4 | ATGATCAATGAAATTCAAATCGCGGCCTTCAATGCCGCCTACGCGAAG ACCATAGACAGTGATGCAATGGAGCAATGGCCAACCTTTTTCACCAAG GATTGCCACTATTGCGTCACCAATGTCGACAACCATGATGAGGGACTT GCTGCCGGCATTGTCTGGGCGGATTCGCAGGACATGCTCACCGACCGA ATTTCTGCGCTGCGCGAAGCCAATATCTACGAGCGCCACCGCTATCGCC ATATCCTGGGTCTGCCTTCGATCCAGTCAGGCGATGCAACACAGGCCA GCGCTTCCACTCCGTTCATGGTGCTGCGCATCATGCATACAGGGGAAA CAGAGGTCTTTGCCAGCGGTGAGTACCTCGACAAATTCACCACGATCG ATGGCAAGTTACGTCTGCAAGAACGCATCGCGGTTTGCGACAGCACGG TGACGGACACGCTGATGGCATTGCCGCTATGA | 3 |
| tphB | Q3C1D3 | ATGACAATAGTGCACCGTAGATTGGCTTTGGCCATCGGCGATCCCCAC GGTATTGGCCCAGAAATCGCACTGAAAGCTCTCCAGCAGCTGTCTGTC ACCGAAAGGTCTCTTATCAAGGTCTATGGACCTTGGAGCGCTCTCGAG CAAGCCGCACGGGTTTGCGAAATGGAGCCGCTTCTTCAAGACATCGTT CACGAGGAAGCCGGCACACTTACACAACCAGTTCAATGGGGAGAAATC ACCCCGCAGGCTGGTCTATCTACGGTGCAATCCGCAACAGCGGCTATC CGAGCGTGCGAAAACGGCGAAGTCGATGCCGTCATTGCCTGCCCTCAC CATGAAACGGCCATTCACCGCGCAGGCATAGCGTTCAGCGGCTACCCA TCTTTGCTCGCCAATGTTCTTGGCATGAACGAAGACCAGGTATTCCTGA TGCTGGTGGGGGCTGGCCTGCGCATAGTGCATGTCACTTTGCATGAAA GCGTGCGCAGCGCATTGGAGCGGCTCTCTCCTCAGTTGGTGGTCAACG CGGCGCAGGCTGCCGTGCAGACATGCACCTTACTCGGAGTGCCTAAAC CAAAAGTCGCTGTATTCGGGATCAACCCTCATGCATCTGAAGGACAGT TGTTCGGCCTGGAGGACTCCCAGATCACCGTTCCCGCTGTCGAGACACT GCGCAAGCGCGGCCTAGCAGTAGACGGCCCCATGGGAGCTGACATGGT TCTGGCACAGCGCAAGCACGACCTGTATGTAGCCATGCTGCACGATCA GGGCCATATCCCCATCAAGCTGCTGGCACCTAACGGAGCCAGCGCACT ATCTATCGGTGGCAGGGTGGTGCTTTCCAGCGTGGGCCATGGCAGCGC CATGGACATTGCCGGCCGTGGCGTGGCTGACGCCACGGCCCTCCTACG CACAATAGCCCTACTCGGAGCCCAACCGGTCTGA | 4 |
| SlOMT | K4CX40 | GTGAAGCTGGATTCAAAGGTGTTAACCTAATATGTTGTGTCTGTAATTT TTGGGTCATGGAATTTTACAAGTAG | 5 |
| HsOMT | P21964 | ATGGGCGATACCAAAGAACAGCGTATTCTGAATCATGTTCTGCAGCAT GCCGAACCGGGTAATGCACAGAGCGTTCTGGAAGCAATTGATACCTAT TGTGAACAGAAAGAATGGGCCATGAATGTGGGTGATAAAAAAGGCAA AATTGTGGATGCCGTGATCCAAGAACATCAGCCGAGCGTGCTGCTGGA ACTGGGTGCATATTGTGGTTATAGCGCAGTTCGTATGGCACGTCTGCTG AGTCCGGGTGCACGTCTGATTACCATTGAAATTAACCCGGATTGTGCA GCAATTACCCAGCGTATGGTTGATTTTGCCGGTGTTAAAGATAAAGTTA CCCTGGTTGTTGGTGCAAGCCAGGATATTATTCCGCAGCTGAAAAAAA AATATGACGTGGATACCCTGGATATGGTGTTTCTGGATCATTGGAAAG ATCGTTATCTGCCGGATACCCTGCTGCTGGAAGAATGTGGTCTGCTGCG TAAAGGCACCGTTCTGCTGGCAGATAATGTTATTTGTCCTGGTGCACCG GATTTTCTGGCACATGTTCGTGGTAGCAGCTGTTTTGAATGTACCCATT ATCAGTCCTTTCTGGAATATCGTGAAGTTGTTGATGGTCTGGAAAAAGC CATCTATAAAGGTCCGGGTAGCGAAGCAGGTCCGTAACTTAA | 6 |
| MsOMT | P28002 | GTGCTGGATTCCAAGGTTTCAAAGTCCATTGTAATGCTTTCAACACATA CATCATGGAGTTTCTTAAGAAGGTTTAA | 7 |
| pobA | Q88H28 | GCTTCAGCTGGTTCATGACCCAACTGCTGCATGACTTCGGTAGCCACAA GGACGCCTGGGACCAGAAGATGCAGGAAGCTGACCGCGAGTACTTCCT GACCTCGCCGGCGGGCCTGGTGAACATTGCCGAGAACTATGTGGGGCT GCCGTTCGAGGAAGTTGCCTGA | 8 |

TABLE 3-continued

| Nucleic acid sequences of genes used in present invention | | | |
|---|---|---|---|
| Gene | UniProtKB Accession Number | Sequence (5'-3') | SEQ ID NO: |
| pobA$^{Mut}$ | | GCTTCAGCTGGTTCATGACCCAACTGCTGCATGACTTCGGTAGCCACAA<br>GGACGCCTGGGACCAGAAGATGCAGGAAGCTGACCGCGAGTACTTCCT<br>GACCTCGCCGGCGGGCCTGGTGAACATTGCCGAGAACTTTGTGGGGCT<br>GCCGTTCGAGGAAGTTGCCTGA | 9 |
| aroY | B2DCZ6 | ACGCCGTGGAAGAGGCGATCCCAGGCTTCCTGCAGAACGTGTACGCCC<br>ACACCGCCGGTGGCGGTAAGTTCCTGGGCATCCTGCAGGTCAAGAAGC<br>GCCAGCCGAGCGACGAAGGCCGTCAGGGCCAAGCCGCCCTGATCGCCC<br>TGGCCACCTACAGCGAGCTGAAGAACATCATCCTGGTGGACGAGGACG<br>TGGACATCTTCGACAGCGACGACATCCTGTGGGCCATGACCACCCGCA<br>TGCAGGGCGACGTGAGCATCACCACCCTGCCAGGCATCCGTGGCCATC<br>AGCTGGACCCGAGCCAGAGCCCAGACTACAGCACCAGCATCCGTGGCA<br>ACGGCATCAGCTGCAAGACCATCTTCGACTGCACCGTGCCGTGGGCCC<br>TGAAAGCCCGTTTCGAGCGTGCCCCATTCATGGAAGTGGACCCGACCC<br>CGTGGGCCCCAGAGCTGTTCAGCGACAAGAAGTAA | 10 |
| lpdC | F9US27 | AATTGGTTAACCGTGCCATTCCTGGTAAAGTGACGAATGTTTATAATCC<br>GCCGGCTGGTGGTGGTAAGTTGATGACCATCATGCAGATTCACAAGGA<br>TAATGAAGCGGATGAAGGCATTCAACGGCAAGCTGCCTTGCTTGCGTT<br>CTCAGCCTTTAAGGAATTGAAGACTGTTATCCTGGTTGATGAAGATGTT<br>GATATTTTTGATATGAATGATGTGATTTGGACGATGAATACCCGTTTCC<br>AAGCCGATCAGGACTTGATGGTCTTATCAGGCATGCGGAATCATCCGT<br>TGGACCCATCGGAACGCCCACAATATGATCCAAAGTCGATTCGTTTCC<br>GTGGGATGAGTTCTAAACTAGTGATTGATGGCACCGTACCATTCGATAT<br>GAAGGACCAATTTGAACGGGCCCAATTCATGAAAGTGGCTGACTGGGA<br>GAAGTATTTGAAGTAA | 11 |
| phK | A0A0S2UP50 | ATGACAACTCAACCGGAAACCAAATCCTTTGAAGAGCTGACCCGATAC<br>ATCCGAGTGCGCAGTGAGCCGGGCGACAAGTTCGTGGAATTCGACTTC<br>GCCATTGCTTACCCCGAGCTCTTCGTTGAGCTCGTGCTGCCTCACGAGG<br>CCTTCGAGATTTTCTGCAAACATAACAAAGTCGTCCACATGGACTCCAA<br>CATAATCCGCAAAATTGACGAAGACATGGTCAAGTGGCGGTTCGGAGA<br>GCATGGCAAGCGCTACTGA | 12 |
| phL | Q84AQ4 | ATGAGTATTGAAATCAAGACCAATTCGGTGGAACCTATCCGCCATACT<br>TATGGCCACATCGCCCGTCGCTTCGGTGATAAGCCGGCTACCCGTTATC<br>AGGAGGCCAGCTACGACATTGAGGCAAAGACCAATTTCCATTACCGGC<br>CCCAGTGGGATTCCGAGCACACCCTGAACGATCCCACGCGTACCGCCA<br>TCCGCATGGAAGACTGGTGCGCCGTTTCCGATCCCCGCCAGTTTTACTA<br>TGGCGCCTATGTCGGCAACCGGGCCAAGATGCAGGAGTCGGCCGAGAC<br>CAGCTTTGGCTTCTGCGAAAAGCGTAATCTGCTGACCCGCCTTTCCGAA<br>GAAACCCAGAAGCAATTGTTGCGGCTGCTGGTGCCCCTGCGTCATGTC<br>GAGCTTGGCGCCAACATGAACAACGCCAAGATCGCCGGTGATGCCACC<br>GCCACGACCGTCTCCCAGATGCACATCTACACTGGGATGGATCGCTTG<br>GGCATTGGCCAGTACCTGTCCCGTATTGCATTGATGATTGATGGCAGCA<br>CCGGTGCCGCTCTGGATGAGTCCAAGGCCTACTGGATGGATGACGAAA<br>TGTGGCAACCCATGCGCAAGCTGGTCGAAGACACGCTTGTGGTCGATG<br>ATTGGTTTGAGCTGACTCTGGTTCAGAACATTCTTATCGACGGAATGAT<br>GTACCCGCTGGTCTACGACAAGATGGACCAGTGGTTCGAAAGCCAGGG<br>TGCTGAAGATGTGTCCATGCTCACGGAGTTCATGCGTGACTGGTACAA<br>GGAATCCCTACGCTGGACTAATGCCATGATGAAAGCCGTGGCCGGTGA<br>AAGTGAGACTAACCGTGAGTTGCTTCAAAAATGGATCGATCACTGGGA<br>ACCGCAGGCCTACGAAGCCCTGAAACCTCTGGCCGAAGCCTCCGTTGG<br>CATCGACGGGCTGAATGAAGCCCGGGCGGAACTCTCTGCCCGCCTGAA<br>GAAATTCGAACTGCAGAGCCGGGGAGTCTCAGCATGA | 13 |
| phM | Q84AQ3 | ATGAGCCAGCTTGTATTTATTGTATTCCAGGACAACGACGACTCCCGCT<br>ACCTCGCGGAAGCCGTTATGGAAGATAACCCCGACGCCGAAATGCAGC<br>ACCAGCCGGCCATGATCCGGATCCAGGCGGAAAAACGTCTGGTGATCA<br>ACCGCGAAACCATGGAAGAAAAGCTGGGGCGAGACTGGGATGTTCAG<br>GAAATGCTCATAAATGTTATCAGCATCGCCGGCAACGTCGATGAAGAC<br>GATGATCACTTCATTCTTGAATGGAATTAA | 14 |
| phN | Q84AQ2 | AGTACTGCCAGGCCACCAACTTCCATACTTGGATTCCGGAGAAGGAAG<br>AGATGGACTGGATGTCCGAGAAGTATCCGGACACTTTCGACAAGTACT<br>ACCGTCCGCGTTACGAGTACCTGGCGAAAGAGGCTGCCGCTGGCCGTC<br>GCTTCTACAACAACACCCTGCCGCAGCTGTGCCAAGTGTGTCAGATCCC<br>GACCATTTTCACCGAGAAAGATGCCCCAACCATGCTCAGCCATCGGCA<br>GATAGAACATGAGGGCGAACGCTATCACTTCTGCTCTGACGGCTGCTG<br>CGACATCTTCAAACACGAGCCGGAGAAGTACATACAGGCCTGGCTGCC<br>GGTGCACCAGATCTACCAGGGCAACTGTGAAGGCGGGGATCTCGAGAC<br>CGTGGTGCAGAAGTATTACCACATCAATATCGGAGAGGACAATTTCGA<br>CTACGTTGGATCGCCCGACCAGAAACACTGGCTGTCGATCAAGGGCCG<br>GAAGCCTGCAGACAAGAACCAGGACGCCGCCTGA | 15 |

TABLE 3-continued

Nucleic acid sequences of genes used in present invention

| Gene | UniProtKB Accession Number | Sequence (5'-3') | SEQ ID NO: |
|---|---|---|---|
| phO | Q84AQ1 | ATGAGTGTAAACGCACTTTACGACTACAAGTTTGAACCTAAAGACAAG<br>GTCGAGAACTTCCACGGCATGCAGCTGCTGTATGTCTACTGGCCCGATC<br>ACCTGCTGTTCTGCGCGCCCTTCGCGCTGCTGGTGCAGCCGGGTATGAC<br>CTTCAGTGCCCTGGTGGACGAGATTCTCAAGCCGGCTACCGCCGCGCA<br>CCCGGACTCTGCCAAGGCGGACTTCCTGAATGCCGAGTGGTTGCTGAA<br>CGATGAACCGTTCACACCCAAGGCTGACGCCAGCCTGAAAGAGCAGGG<br>TATTGATCACAAGAGCATGCTGACGGTGACCACGCCGGGCCTGAAGGG<br>CATGGCGAACGCCGGTTACTGA | 16 |
| phP | Q84AQ0 | CTGAAGACACCCAGCGTTCGGCCCTGTTCAAGAAGATATAG | 17 |
| phQ | A0A0S2UPA7 | ATGGGCATGGGTTTCCTAGTGTTCAACCGCACAACGGGAGGTCACTTT<br>ACCTGCCAGGAGGGCCAGAGTGTGCTCAAGGCCATGGAGCAGAGGGG<br>CCTGAAGTGTGTCCCCGTGGGCTGCCGGGGTGGTGGTTGCGGATTTTGT<br>AAGATCCGGGTTCTGGAAGGGTATTTCGAGTGCGGCAAGATGAGCAAG<br>CGGCACGCCCCGCCTGAAGCCGTTGAAAAAGGGGAAGTTCTGGCCTGC<br>CGGATCTACCCACTGACTGATCTGATCATTGAGTGTCCGCCGCAACCGG<br>CGGCGGACTTTGCGAGCTAG | 18 |
| catA | Q88GK8 | ATGACCGTGAAAATTTCCCACACTGCCGACATTCAAGCCTTCTTCAACC<br>GGGTAGCTGGCCTGGACCATGCCGAAGGAAACCCGCGCTTCAAGCAGA<br>TCATTCTGCGCGTGCTGCAAGACACCGCCCGCCTGATCGAAGACCTGG<br>AGATTACCGAGGACGAGTTCTGGCACGCCGTCGACTACCTCAACCGCC<br>TGGGCGGCCGTAACGAGGCAGGCCTGCTGGCTGCTGGCCTGGGTATCG<br>AGCACTTCCTCGACCTGCTGCAGGATGCCAAGGATGCCGAAGCCGGCC<br>TTGGCGGCGGCACCCCGCGCACCATCGAAGGCCCGTTGTACGTTGCCG<br>GGGCGCCGCTGGCCCAGGGCGAAGCGCGCATGGACGACGGCACTGAC<br>CCAGGCGTGGTGATGTTCCTTCAGGGCCAGGTGTTCGATGCCGACGGC<br>AAGCCGTTGGCCGGTGCCACCGTCGACCTGTGGCACGCCAATACCCAG<br>GGCACCTATTCGTACTTCGATTCGACCCAGTCCGAGTTCAACCTGCGTC<br>GGCGTATCATCACCGATGCCGAGGGCCGCTACCGCGCGCGCTCGATCG<br>TGCCGTCCGGGTATGGCTGCGACCCGCAGGGCCCAACCCAGGAATGCC<br>TGGACCTGCTCGGCCGCCACGGCCAGCGCCCGGCGCACGTGCACTTCT<br>TCATCTCGGCACCGGGGCACCGCCACCTGACCACGCAGATCAACTTTG<br>CTGGCGACAAGTACCTGTGGGACGACTTTGCCTATGCCACCCGCGACG<br>GGCTGATCGGCGAACTGCGTTTTGTCGAGGATGCGGCGGCGGCGCGCG<br>ACCGCGGTGTGCAAGGCGAGCGCTTTGCCGAGCTGTCATTCGACTTCC<br>GCTTGCAGGGTGCCAAGTCGCCTGACGCCGAGGCGCGAAGCCATCGGC<br>CGCGGGCGTTGCAGGAGGGCTGA | 19 |

Experimental Example 1

For the depolymerization of PET into monomers TPA and EG, 1 g of PET in 13 mL of water was reacted, and thus the depolymerization of PET was carried out at various temperatures of 170, 200, and 230°C using microwaves for various reaction times of 15 to 50 minutes (FIG. 1A). During the initial hydrolysis periods, the amount of TPA slowly increased due to the random chain cleavage of PET into TPA and EG (FIG. 1A). After these periods, PET depolymerization rapidly increased by autocatalysis induced by the reaction product TPA. Among the various reaction conditions, the highest TPA yield was obtained after 50 minutes at 230°C (FIG. 1A). This highest yield was determined to be 99.9% of the theoretical maximum TPA yield calculated from the PET consumed during the reaction, in which 24.1% (w/w) of the initial input PET was consumed after 50 minutes at 230°C by the reaction. These results indicate that a large amount of TPA in monomeric form can be obtained from PET hydrolysis without overdegradation.

Figure 2A:
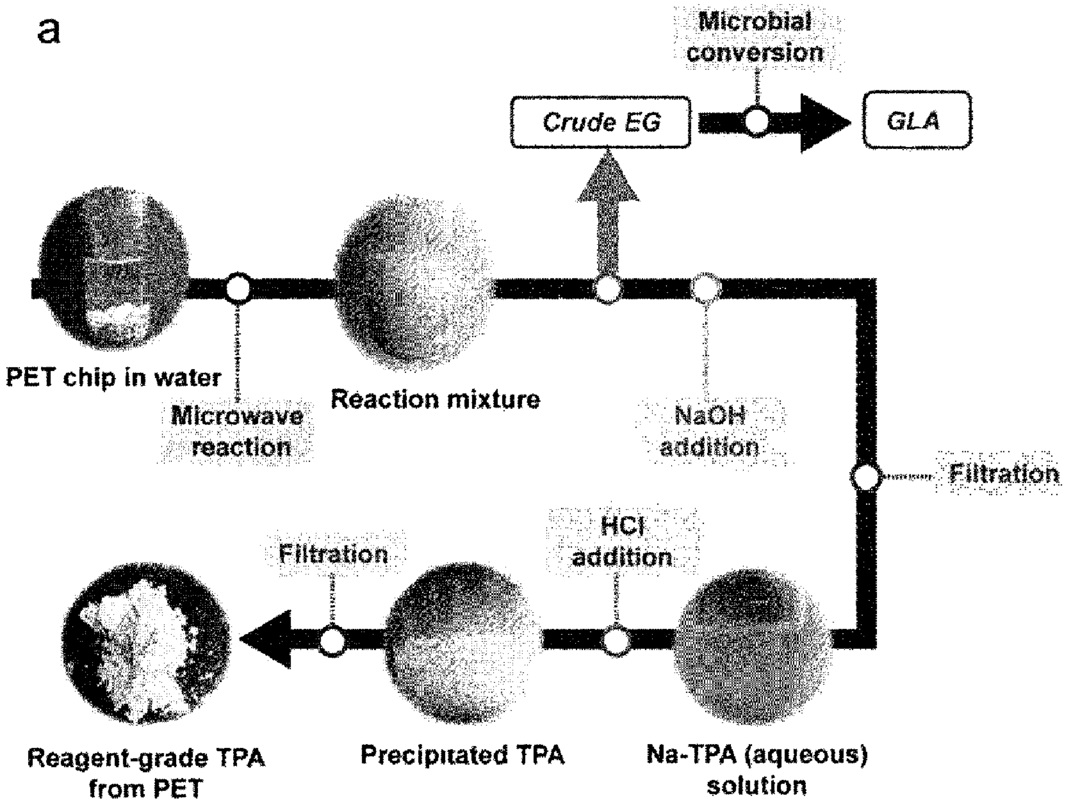
FIGS. 2A to 2E illustrate the production, separation, and identification of EG and TPA from PET.
Figure 2B:
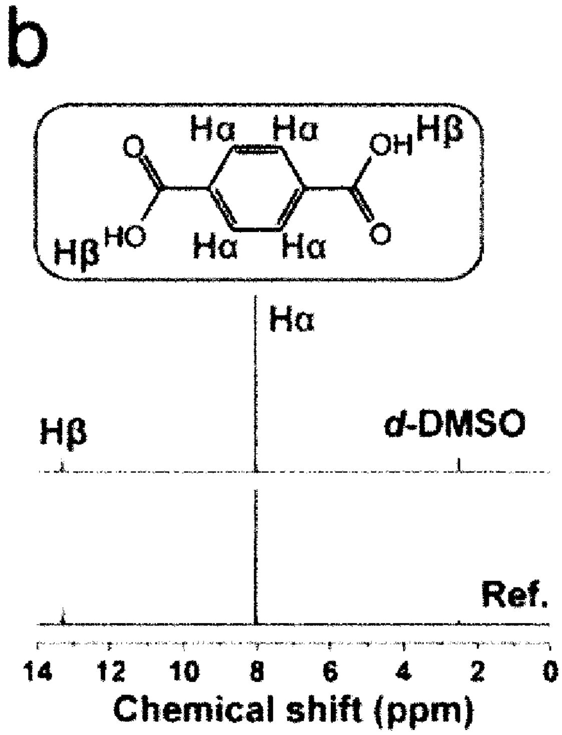
Figure 2C:
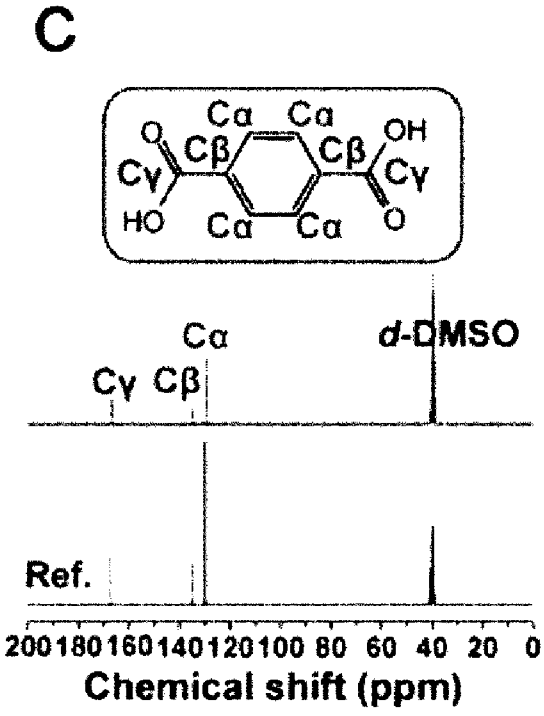

The PET hydrolysate was separated into solid and liquid fractions by filtration. First, to obtain TPA, the solid fraction containing TPA was dissolved in 1 M NaOH, and Na-TPA was then precipitated as TPA by 2 M HCl at room temperature. The precipitated TPA was filtered and vacuum-dried at 80°C (FIG. 2A). To confirm the identity of the TPA samples, $^{1}H$ and $^{13}C$ NMR analyses were performed (FIGS. 2B and 2C). Chemical shifts of the two spectra were identical to those of reagent-grade TPA.

Figure 2D:
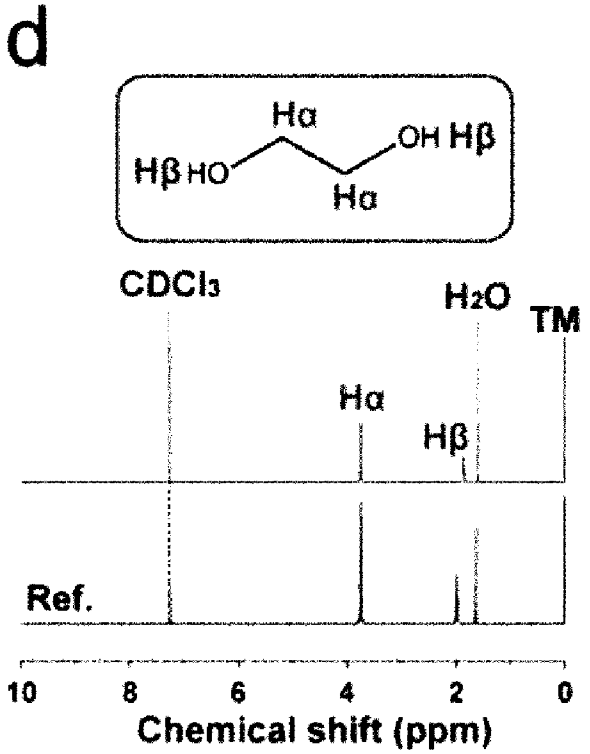
Figure 2E:
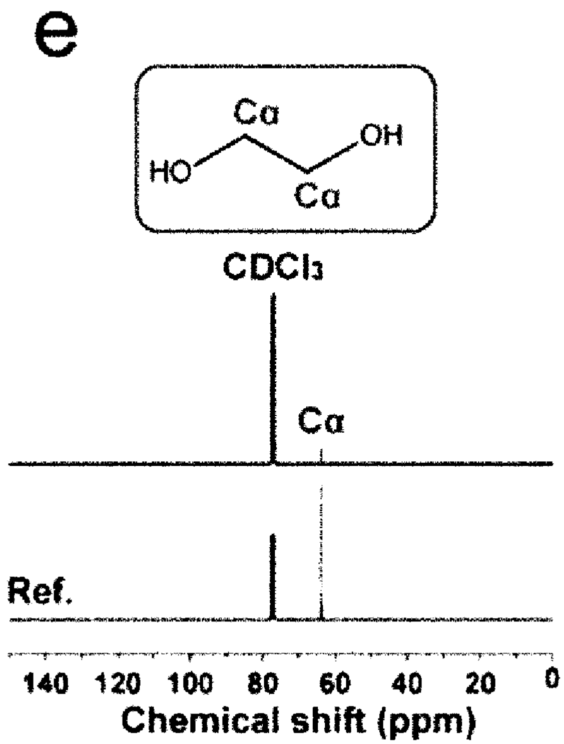

For the separation of EG from the PET hydrolysate obtained by chemical hydrolysis, the liquid fraction was distilled, and $^{1}H$ and $^{13}C$ NMR analyses were performed to confirm the identity of the EG samples (FIGS. 2D and 2E). In this case, chemical shifts were identical to those of reagent-grade EG.

<Experimental Example 2> Bioconversion of TPA to PCA

Figure 3:
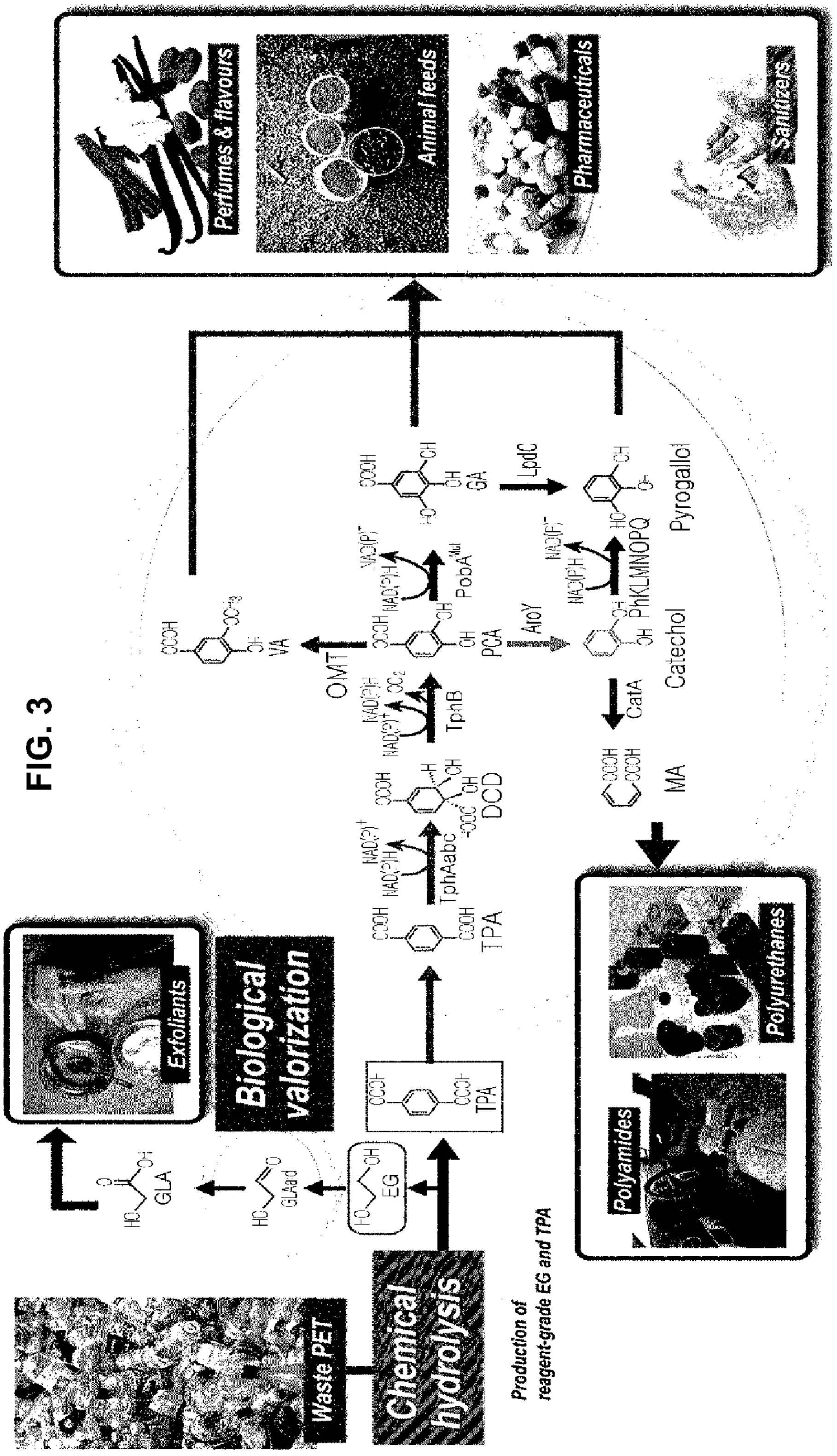
FIG. 3 illustrates an overall scheme for a waste PET biorefinery for PET upcycling.

To experimentally validate the applicability of TPA obtained from waste PET as a feedstock for producing higher-value compounds than PET, PCA was selected as a first product as well as a key intermediate. PCA can serve as a precursor compound for producing various high value-added aromatic compounds or aromatic-derived compounds such as GA, pyrogallol, catechol, MA, and VA (FIG. 3). Therefore, it is important to establish an efficient biocatalyst capable of converting TPA to PCA. The bioconversion of TPA to PCA via DCD has been revealed only in vitro from the TPA degradation pathway of several bacteria that metabolize TPA as a sole carbon source, such as *Comamonas* sp. E6, *Delftia tsuruhatensis* T7, and *Rhodococcus* sp. DK17. The TPA degradation pathway includes two enzymes, TPA 1,2-dioxygenase and DCD dehydrogenase, wherein TPA 1,2-dioxygenase converts TPA to DCD, and DCD dehydrogenase converts DCD to PCA.

Figure 1B:
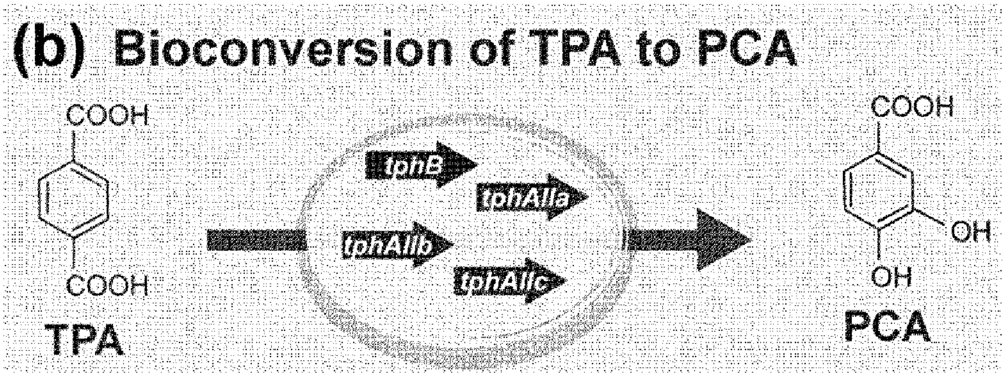
Figure 1C:
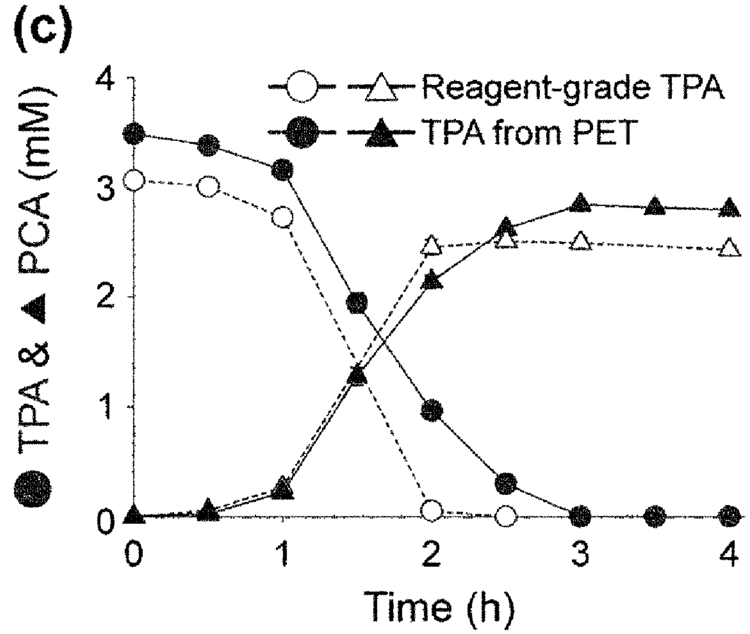
Figure 1D:
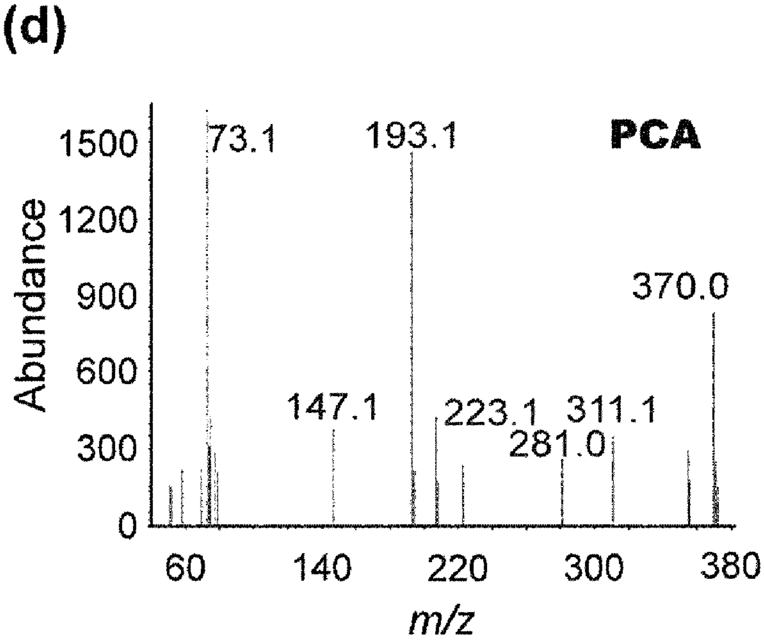
Figure 4A:
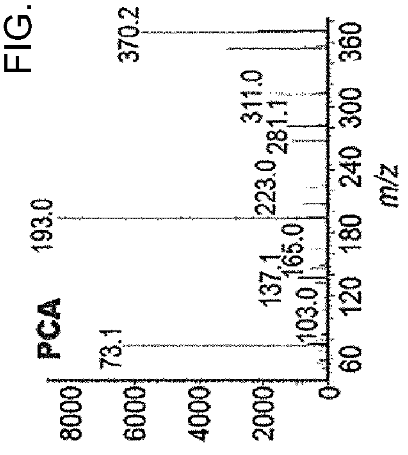
FIGS. 4A to 4F are GC/MS spectra of authentic standards for PCA (FIG. 4A), GA (FIG. 4B), pyrogallol (FIG. 4C), MA (FIG. 4D), VA (FIG. 4E), and GLA (FIG. 4F).

In this experiment, TphAabc which is TPA 1,2-dioxygenase and TphB which is DCD dehydrogenase, both derived from *Comamonas* sp. E6, were used for a biosynthesis route from TPA to PCA in *E. coli*. Unlike other corresponding enzymes of other microbes, these two enzymes have the advantage of possessing dual cofactor utilization capability for both NADH and NADPH. To dissolve TPA in a buffer solution, NaOH was added to adjust pH to 7, and then a 50 g/L TPA solution was prepared for further conversion reactions wherein TPA can be dissolved at a concentration of more than 0.5 g/L. When TPA from the PET hydrolysate was incubated with *E. coli* strain PCA-1 expressing TphAabc and TphB in TG-1 buffer (FIG. 1B), 2.8 mM PCA was produced at a molar yield of 81.4% after three hours, and this was similar to that from reagent-grade TPA (FIG. 1C). PCA production was confirmed by GC/MS (FIGS. 1D and 4A). Since the in vivo production of compounds from TPA has not been reported yet, this experiment is the first experimental demonstration of in vivo PCA production from TPA. TPA from the PET hydrolysate can be used as a feedstock for producing PCA, a key precursor for aromatic compounds or aromatic-derived compounds. Since PCA is a key intermediate compound in lignin refineries, PCA itself has value as a substrate in other bioconversions.

<Experimental Example 3> Bioconversion of TPA to GA

Figure 5A:
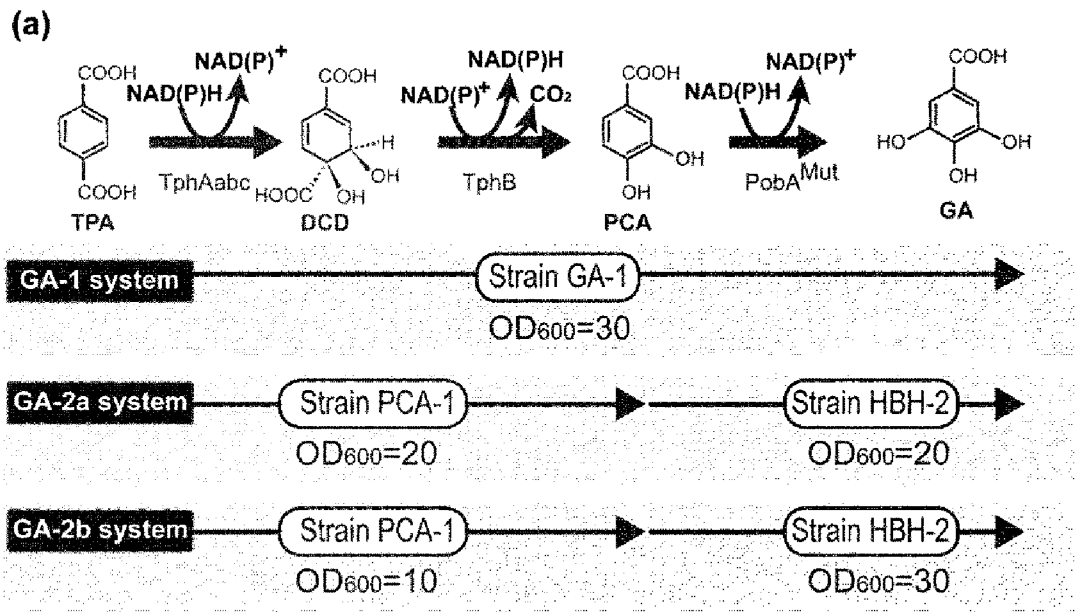
FIGS. 5A to 5C illustrate the bioconversion of TPA to GA.

GA is currently used in the pharmaceutical industry to produce trimethoprim, an antibacterial agent, and propyl gallate, an antioxidant. When a PCA hydroxylase having hydroxylating activity at the meta-position of PCA is identified, TPA can be converted to GA via PCA (FIG. 5A). Although a wild-type p-hydroxybenzoate hydroxylase (PobA from *Pseudomonas aeruginosa*) hydroxylated 4-HBA but not PCA (i.e., 3,4-dihydroxybenzoic acid), structure-based engineered PobA hydroxylated both 4-HBA and PCA to GA.

Figure 6A:
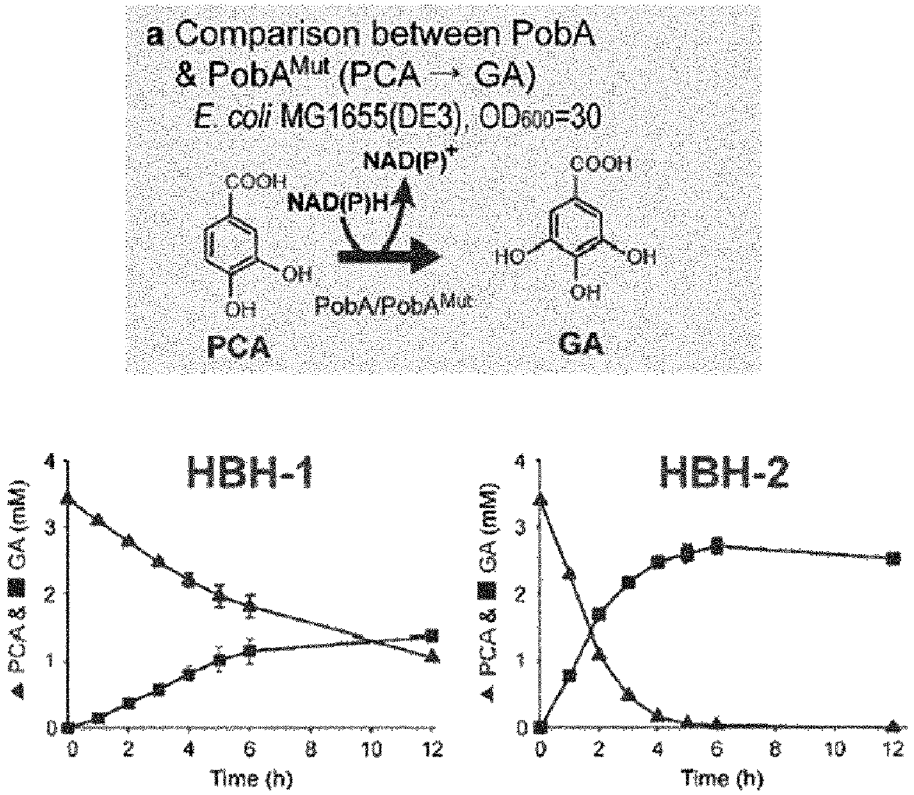
FIGS. 6A to 6D illustrate the bioconversion of TPA to GA using whole-cell catalysts.
Figure 7A:
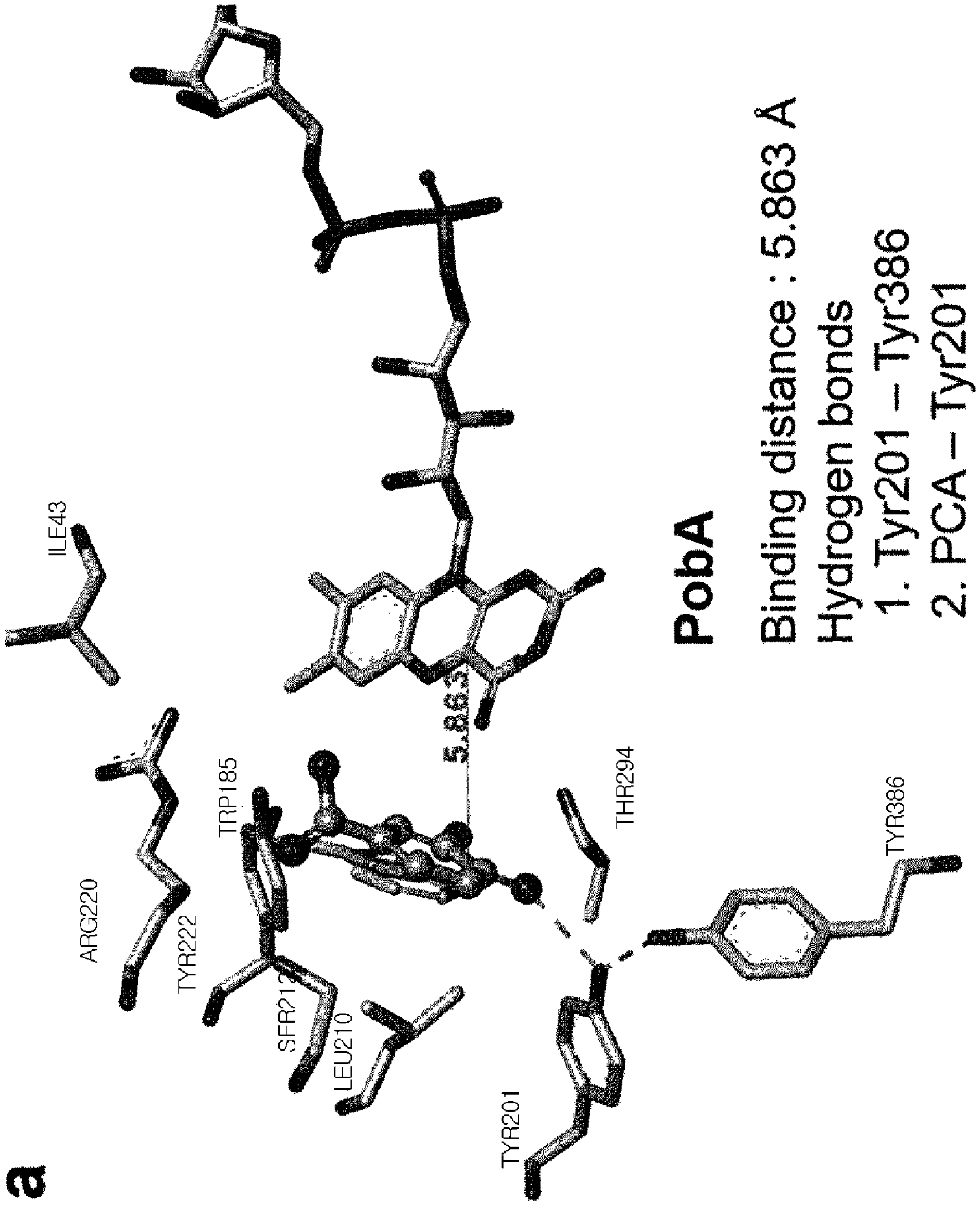
FIGS. 7A and 7B illustrate the docking simulation of the binding of PCA to active sites of PobAs: wild-type PobA (FIG. 7A) and PobA$^{Mut}$, which is a Y385F/T294A double mutant (FIG. 7B), wherein the flavin adenine dinucleotide (FAD)-bound structure of PobA (PDB code 6DLL) was used in the docking simulations, and the structure of PobA$^{Mut}$ was constructed using MODELLER software, and molecular docking simulations were performed using AutoDockFR software.
Figure 7B:
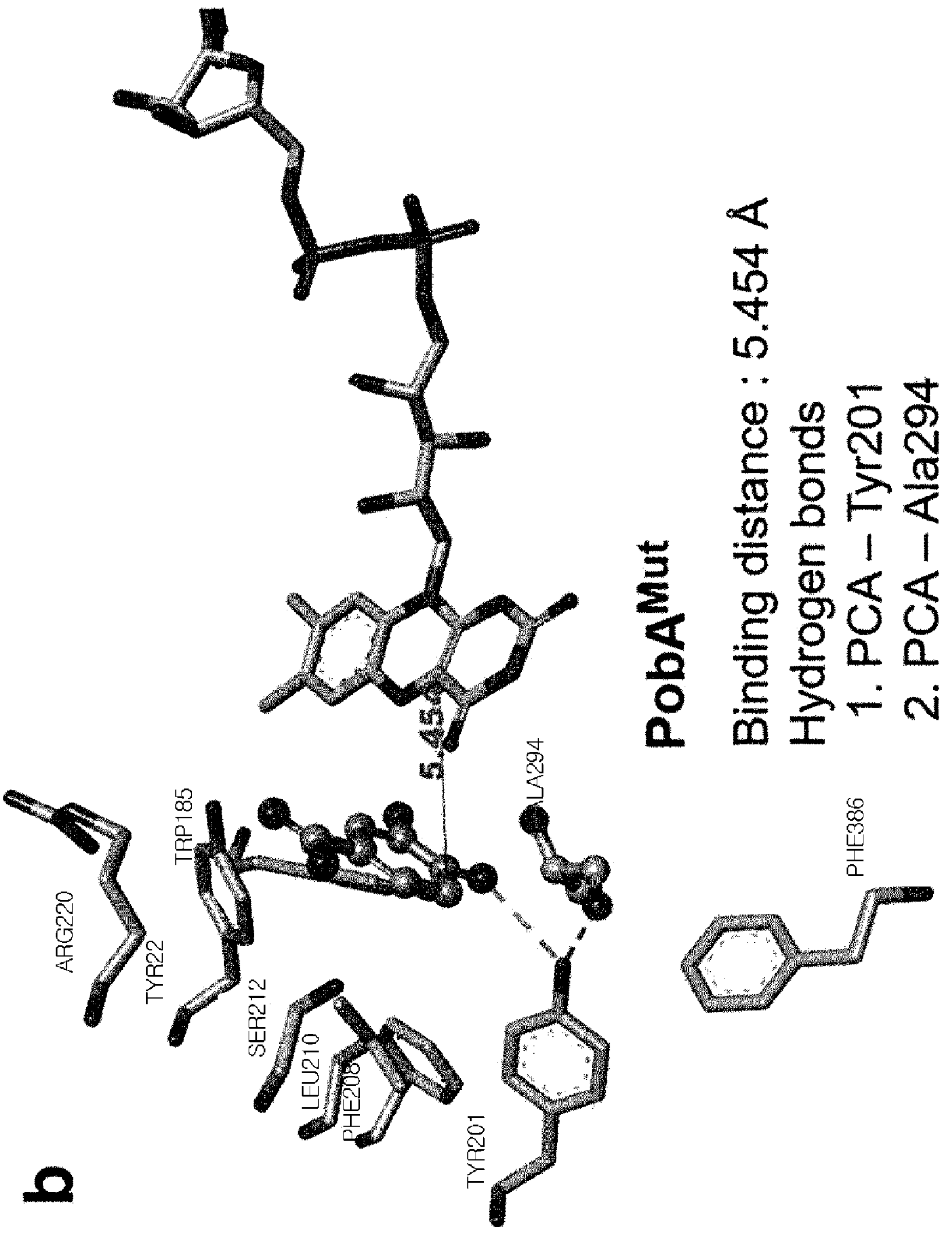

In this experiment, PobA from *P. putida* KT2440 was expressed in *E. coli* (Strain HBH-1) to test the ability of PobA from *P. putida* KT2440 to hydroxylate the meta-position of PCA. As a result, strain HBH-1 produced 1.4 mM GA from PCA at a molar yield of 40.1% after 12 hours in TG-2 buffer at 30°C and 250 rpm (FIG. 6A). To enhance the hydroxylation by PobA, structure-based enzyme engineering following a previous approach was performed. According to molecular docking simulations, Tyr201 formed two hydrogen bonds with Tyr386 and PCA in active sites of wild-type PobA (FIG. 7A). However, PCA formed two hydrogen bonds with Tyr201 and Ala294 at the active site of modeled double mutant $PobA^{Mut}$ (T294A/Y385F), thus leading to a shorter binding distance between a substrate and a FAD cofactor (FIG. 7B). To validate the modeling results, double mutant $PobA^{Mut}$ (T294A/Y385F) was constructed and was expressed in *E. coli* strain HBH-2. Using the HBH-2 strain expressing $PobA^{Mut}$, 2.5 mM GA was produced from PCA at a molar yield of 74.3% after 12 hours (FIG. 6A), which was an 83.7% increase compared to that of wild-type PobA.

Figure 4B:
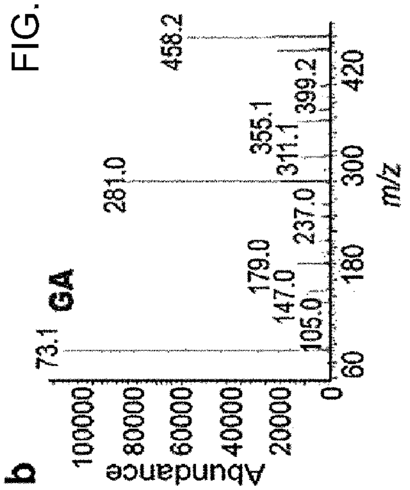
Figure 5B:
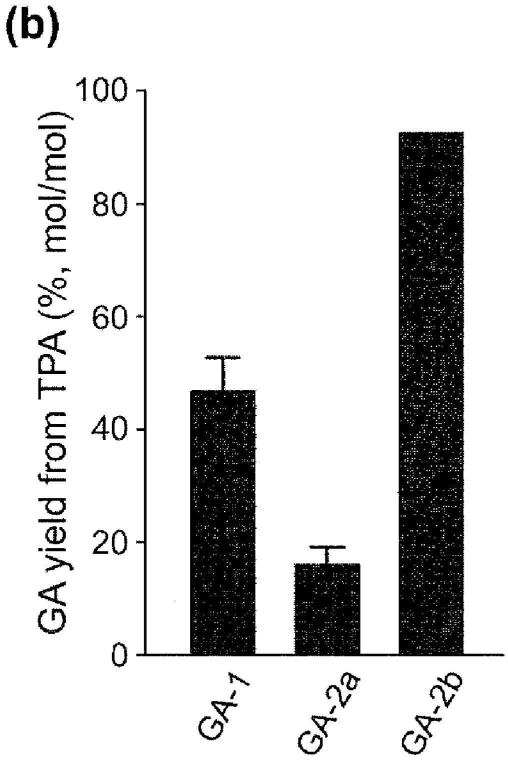
Figure 5C:
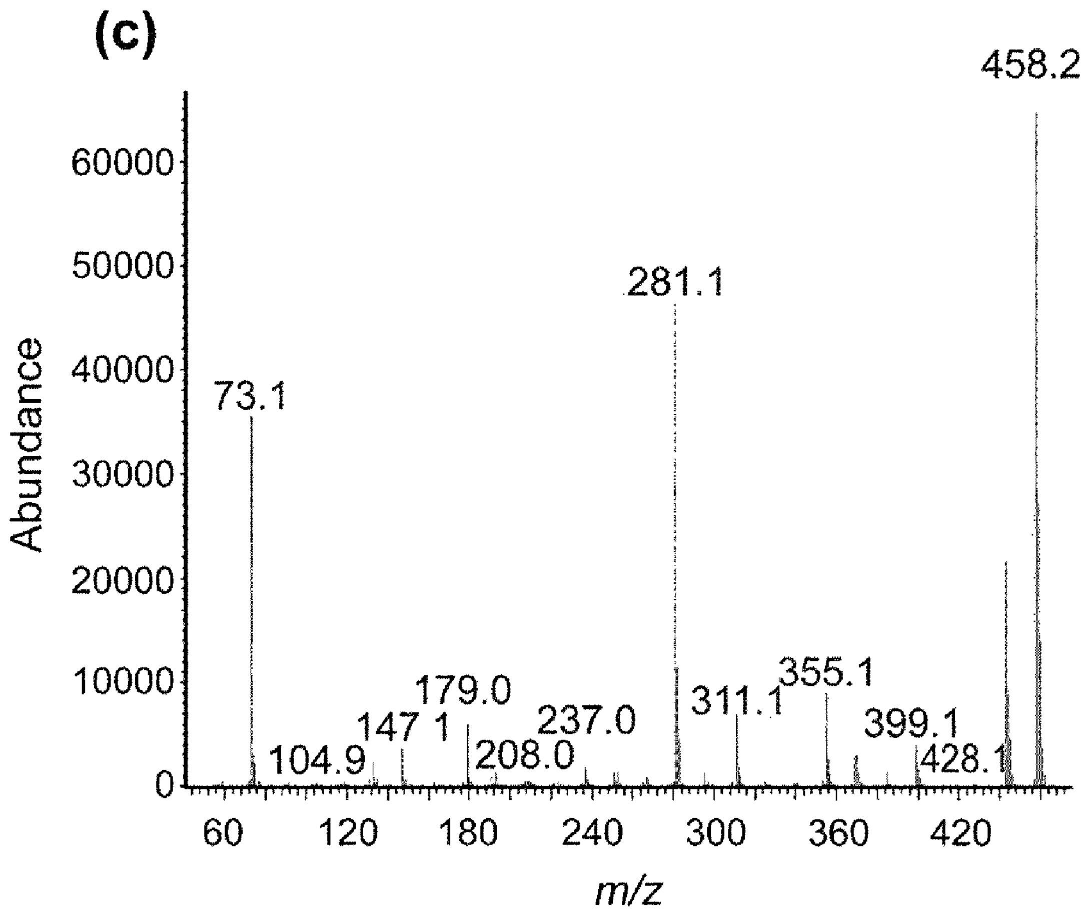
Figure 6B:
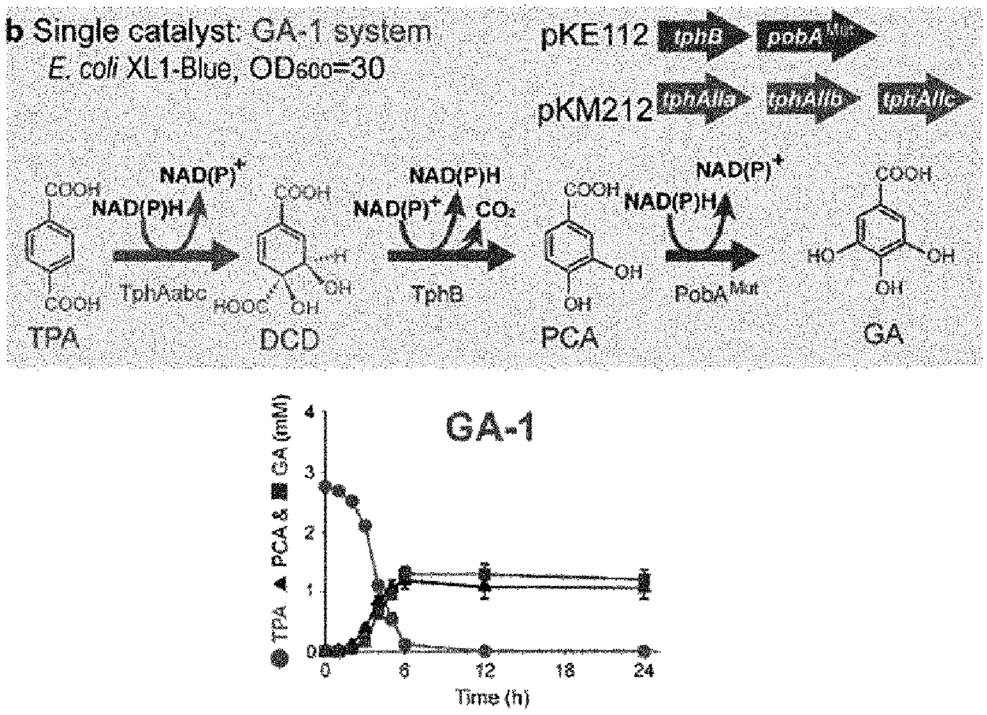
Figure 6C:
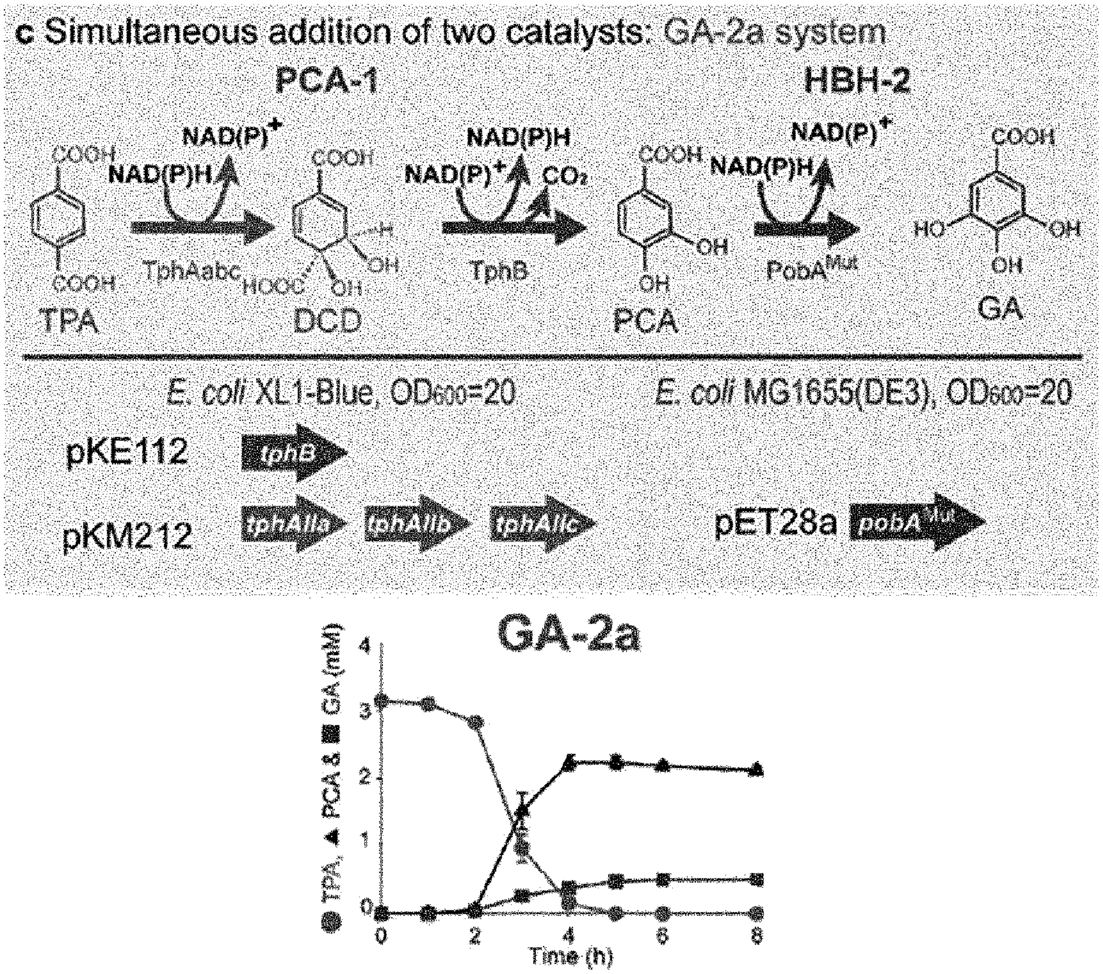
Figure 6D:
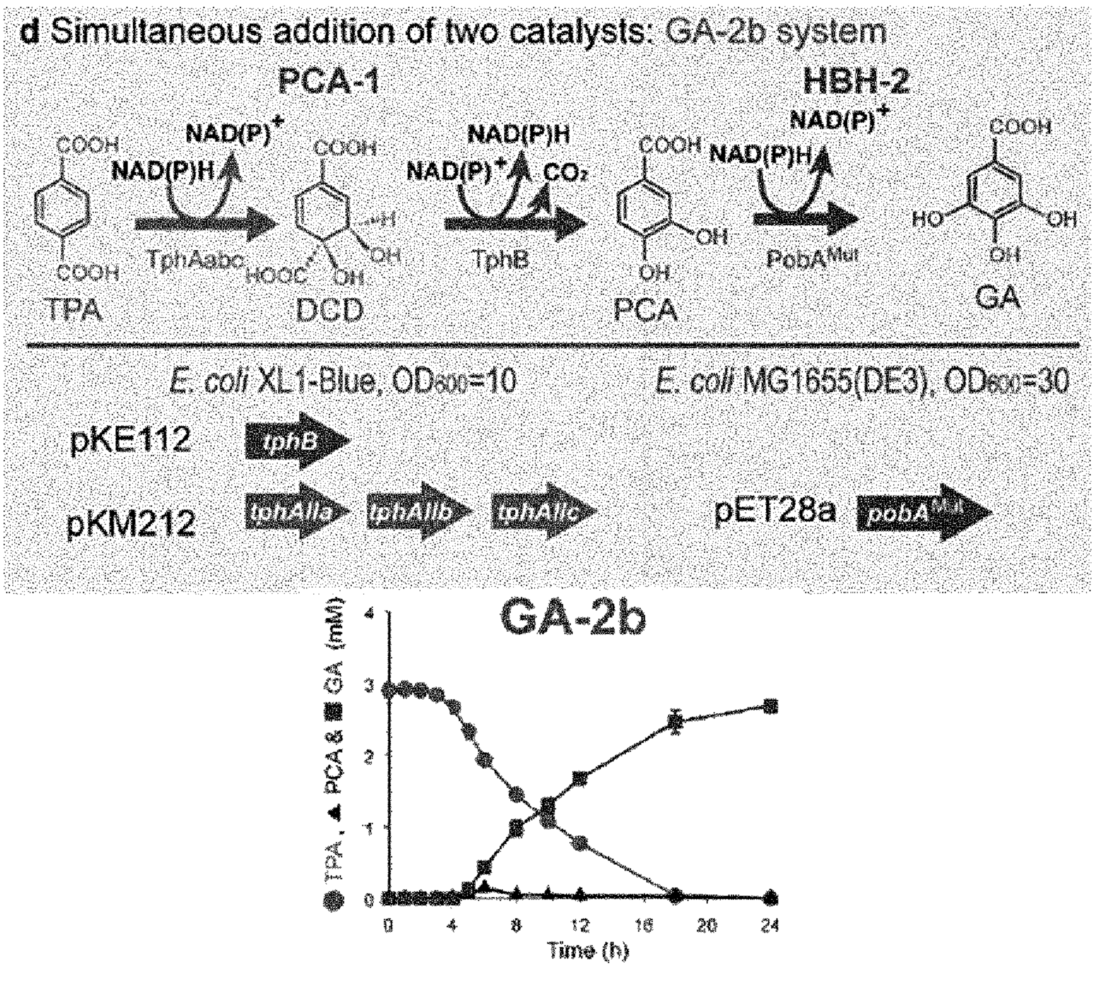

First, the single-catalyst GA-1 system consisting of *E. coli* strain GA-1 expressing TphAabc, TphB, and $PobA^{Mut}$ was tested to produce GA from TPA. The GA-1 system produced only 1.3 mM GA at a molar yield of 46.6% from TPA after 12 hours in TG-2 buffer, but 1.1 mM PCA remained (FIG. 6B). This may be due to the redox imbalance caused by the biosynthesis of GA from PCA by utilizing NAD(P)H in the single-strain system GA-1. To improve the GA yield from TPA, the GA-2a system was constructed in which strains PCA-1 and HBH-2 were simultaneously added to catalyze the synthesis of PCA from TPA and the synthesis of GA from PCA, respectively. However, the GA synthesis catalyst produced only 0.5 mM GA from 3.1 mM TPA with a molar yield of 15.9% (FIG. 6C). Since 2.1 mM of intermediate PCA was accumulated without being converted to GA, the second reaction by the GA synthesis catalyst was a rate-limiting reaction in the GA-2a system. To promote the second conversion step, the $OD_{600}$ values between PCA and GA synthesis catalysts were changed from 20 and 20 in the GA-2a system to 10 and 30 in the GA-2b system (FIG. 6D). As a result, the production and molar yield of GA from TPA increased to 2.7 mM GA and 92.5%, respectively, after 24 hours without accumulating PCA (FIGS. 5B and 6D). GA production by the GA-2b system was confirmed by GC/MS (FIGS. 5C and 4B).

Experimental Example 4> Bioconversion of TPA to Pyrogallol via GA

Pyrogallol is another high value-added compound that can be produced from TPA via PCA. Pyrogallol is currently used as an antioxidant in the oil industry. Pyrogallol can be biosynthesized through two routes: via the decarboxylation of GA synthesized by PCA hydroxylation (FIG. 8A), and via the hydroxylation of catechol that can be synthesized by PCA decarboxylation (FIG. 8B).

Figure 4C:
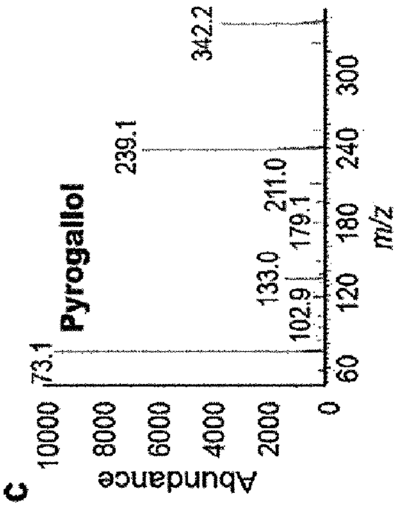
Figure 9A:
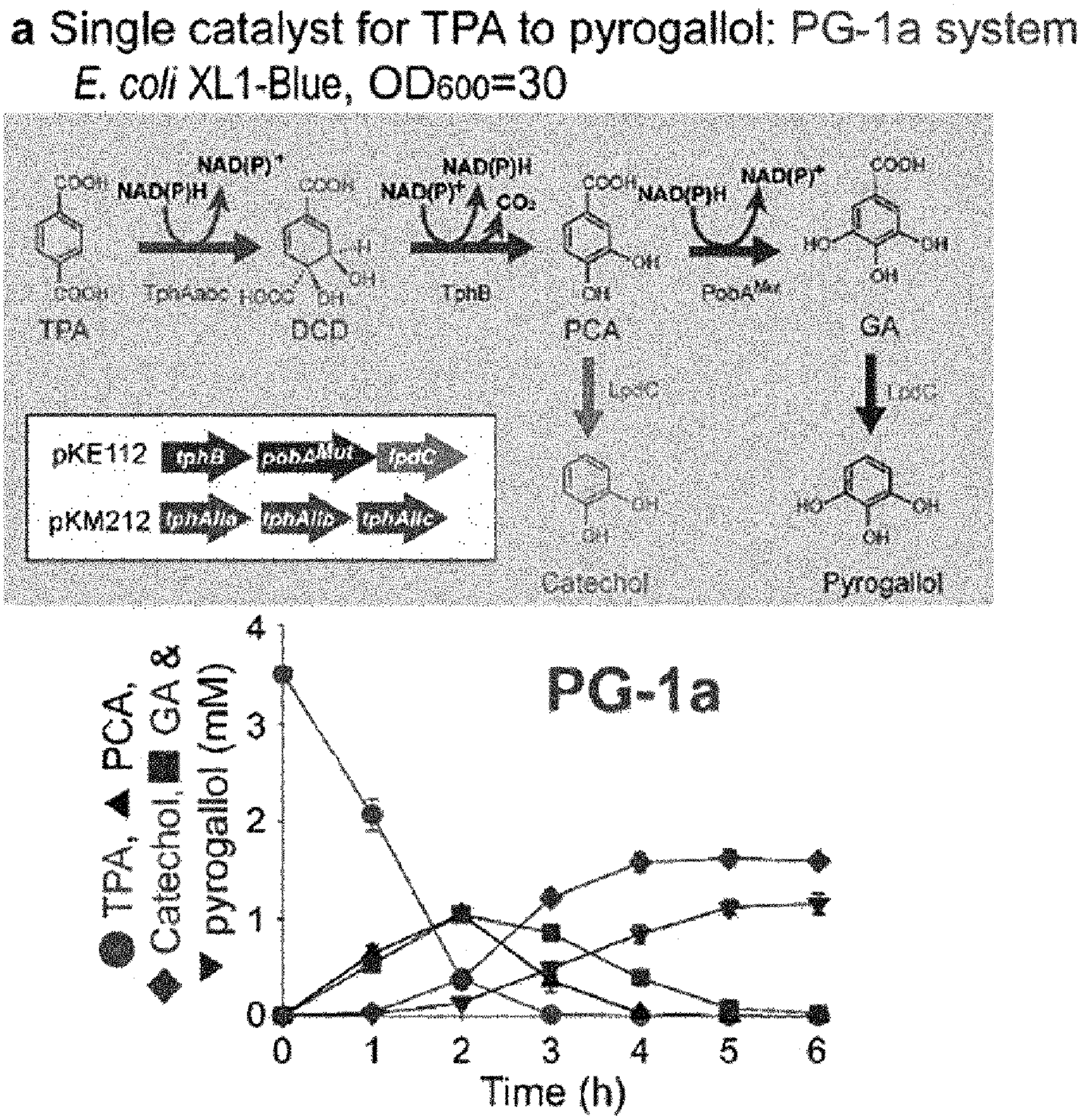
FIGS. 9A to 9E illustrate the bioconversion of TPA to pyrogallol using microbial catalysts.
Figure 10A:
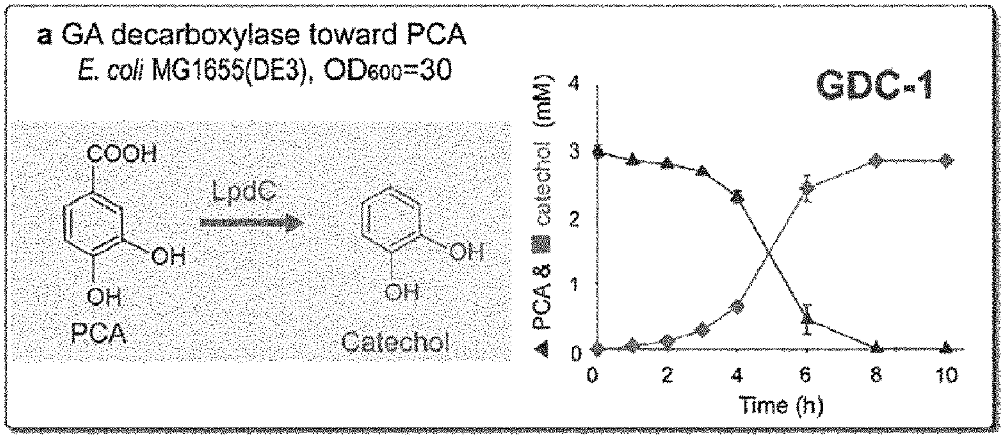
FIGS. 10A and 10B illustrate the promiscuity of GA decarboxylase LpdC toward GA.
Figure 10B:
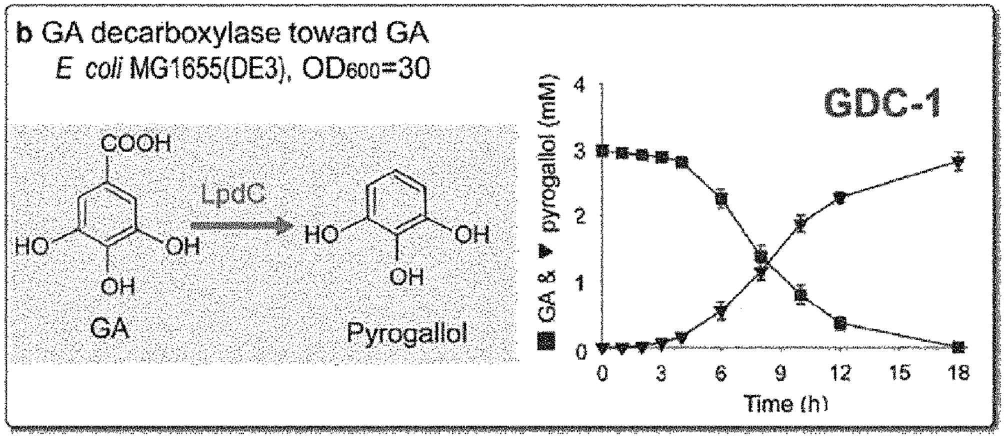

To develop biosynthesis routes for pyrogallol via GA, LpdC, which was found to be a GA decarboxylase in vitro, was introduced as a GA decarboxylation module into the GA biosynthesis route. As a result, *E. coli* strain PG-1a expressing TphAabc, TphB, $PobA^{Mut}$, and LpdC was constructed (FIG. 8A). The PG-1a strain produced 1.1 mM pyrogallol from TPA at a molar yield of 32.7% in TG-2 buffer at 30°C and 250 rpm after six hours (FIGS. 8C and 9A), and pyrogallol production was confirmed by GC/MS (FIGS. 8D and 4C). However, a substantial amount of catechol, 1.6 mM, was also produced as a byproduct after six hours; this was caused by the promiscuity of GA decarboxylase, LpdC, toward PCA. LpdC converted not only GA to pyrogallol but also PCA to catechol. For example, *E. coli* strain GDC-1 expressing LpdC converted 3.0 mM PCA to 2.9 mM catechol after eight hours and then converted 3.0 mM GA to 2.8 mM pyrogallol after 18 hours (FIGS. 10A and 10B). These results indicate that LpdC has promiscuous activity toward PCA because LpdC was previously reported as a GA decarboxylase. Therefore, catechol production was inevitable when using the GA biosynthesis route with PCA as an intermediate.

Figure 9B:
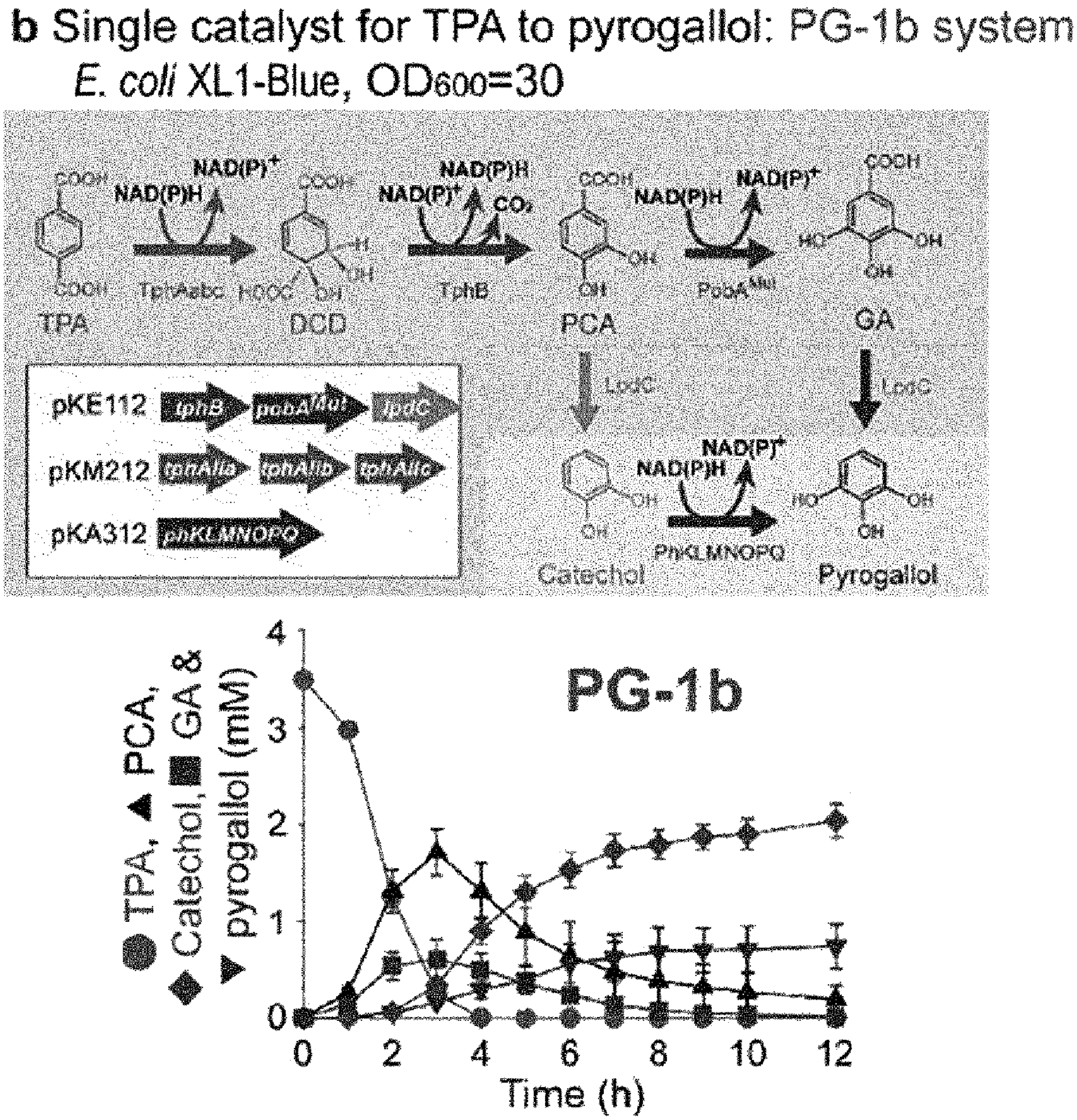
Figure 11A:
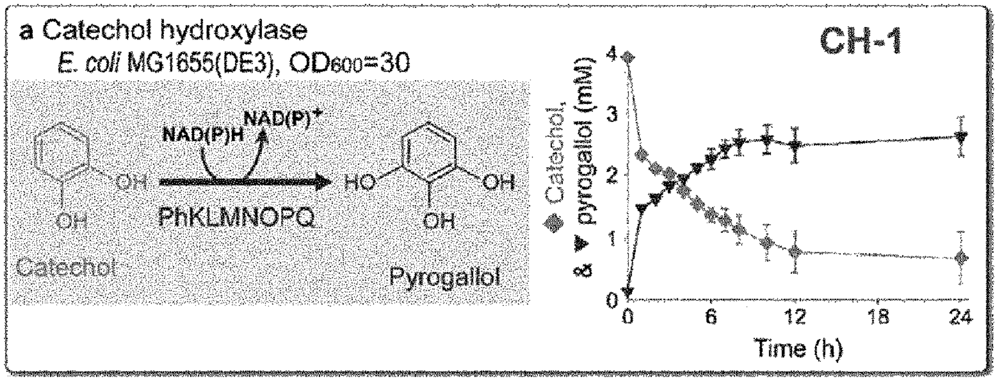
FIGS. 11A to 11C illustrate enzymes used to synthesize pyrogallol and catechol.

For relieving catechol accumulation due to LpdC promiscuity, it was necessary to convert accumulated catechol to pyrogallol. Although a catechol hydroxylase capable of converting catechol to pyrogallol has not yet been reported, a PhKLMNOPQ operon encoding a phenol hydroxylase from *Pseudomonas stutzeri* OX1 was recently found to exhibit promiscuous activity in converting catechol to pyrogallol. *E. coli* strain CH-1 expressing PhKLMNOPQ produced 2.6 mM pyrogallol from catechol at a molar yield of 67.1% after 24 hours (FIG. 11A). The catechol hydroxylation module of PhKLMNOPQ was added to *E. coli* strain PG-1a to construct *E. coli* strain PG-1b (FIG. 8A). However, even when the PG-1b system harboring the catechol hydroxylation module of PhKLMNOPQ was applied to pyrogallol production from TPA, catechol accumulation slightly increased, and the pyrogallol production of 0.7 mM after 12 hours was slightly lower (FIG. 9B) than 1.1 mM produced by the PG-1a system after six hours (FIG. 9B). Comparing GA accumulation and its conversion to pyrogallol between the PG-1a and PG-1b systems, PG-1b accumulated less GA but produced less pyrogallol (FIG. 9B) than PG-1a (FIG. 9A). In PG-1b, the catechol hydroxylation module seemed inactive without converting catechol but accumulated a larger amount of catechol (FIG. 9B) than in PG-1a (FIG. 9A). These results imply that pyrogallol synthesis via the two biosynthesis routes involving two different hydroxylation reactions may be inefficient. This may be because both hydroxylation modules require one or more NAD(P)H molecules.

<Experimental Example 5> Bioconversion of TPA to Pyrogallol via Catechol

Figure 9C:
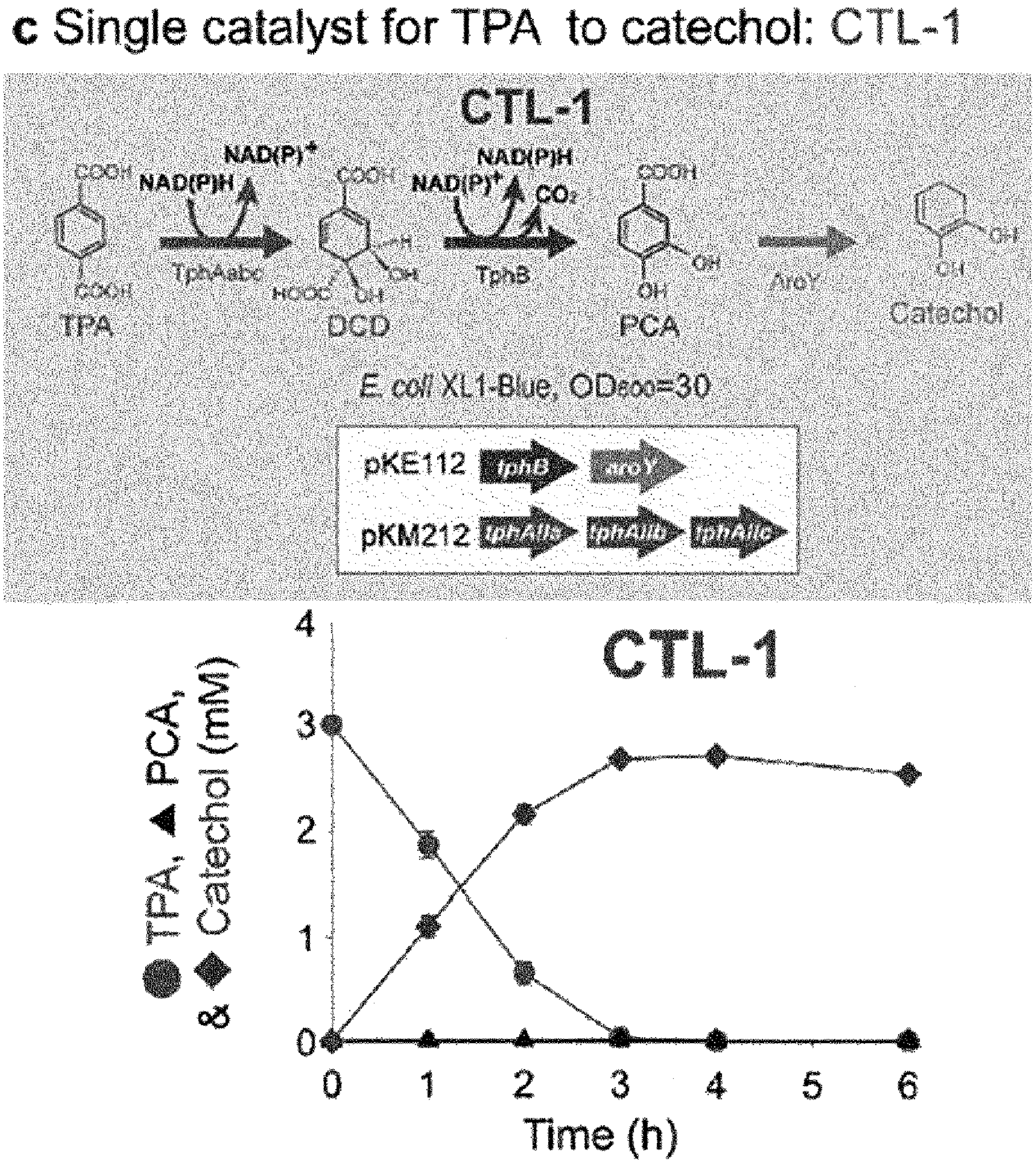
Figure 11B:
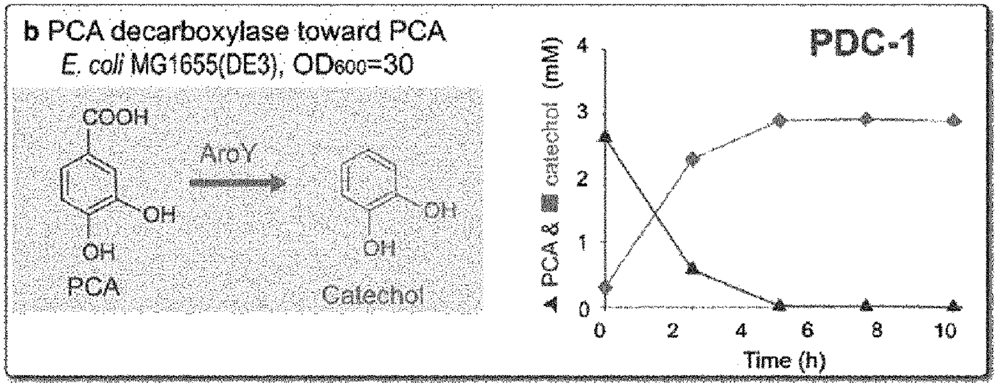

To synthesize pyrogallol without forming a catechol byproduct caused by the promiscuity of LpdC, an alternative pyrogallol synthesis route via catechol was adopted. Based on the PCA synthesis module for TPA conversion to PCA (i.e., the PCA-1 system), the pyrogallol synthesis route was constructed by integrating the PCA decarboxylation module for PCA conversion to catechol and the catechol hydroxylation module for catechol conversion by PhKLMNOPQ in either a single- or double-strain system (i.e., the PG-2a and PG-2b systems, respectively) (FIG. 8B). An AroY enzyme, which was identified as a PCA decarboxylase in several microbes, was adopted as the PCA decarboxylation module. First, the conversion of PCA to catechol by *E. coli* strain PDC-1 expressing AroY was verified, in which PCA was converted to 2.9 mM catechol at a molar yield of 97.8% in TG-2 buffer after five hours (FIG. 11B). The function of the catechol hydroxylation module for catechol conversion to pyrogallol by PhKLMNOPQ had been verified using the CH-1 strain (FIG. 11A). To further evaluate the capability of the PCA decarboxylation module to produce catechol and AroY in conjunction with the PCA synthesis module for TPA conversion to PCA, *E. coli* strain CTL-1 expressing TphAabc, TphB, and AroY was tested, and strain CTL-1 produced 2.7 mM catechol from TPA at a molar yield of 90.1% without PCA accumulation after four hours (FIG. 9C).

Figure 9D:
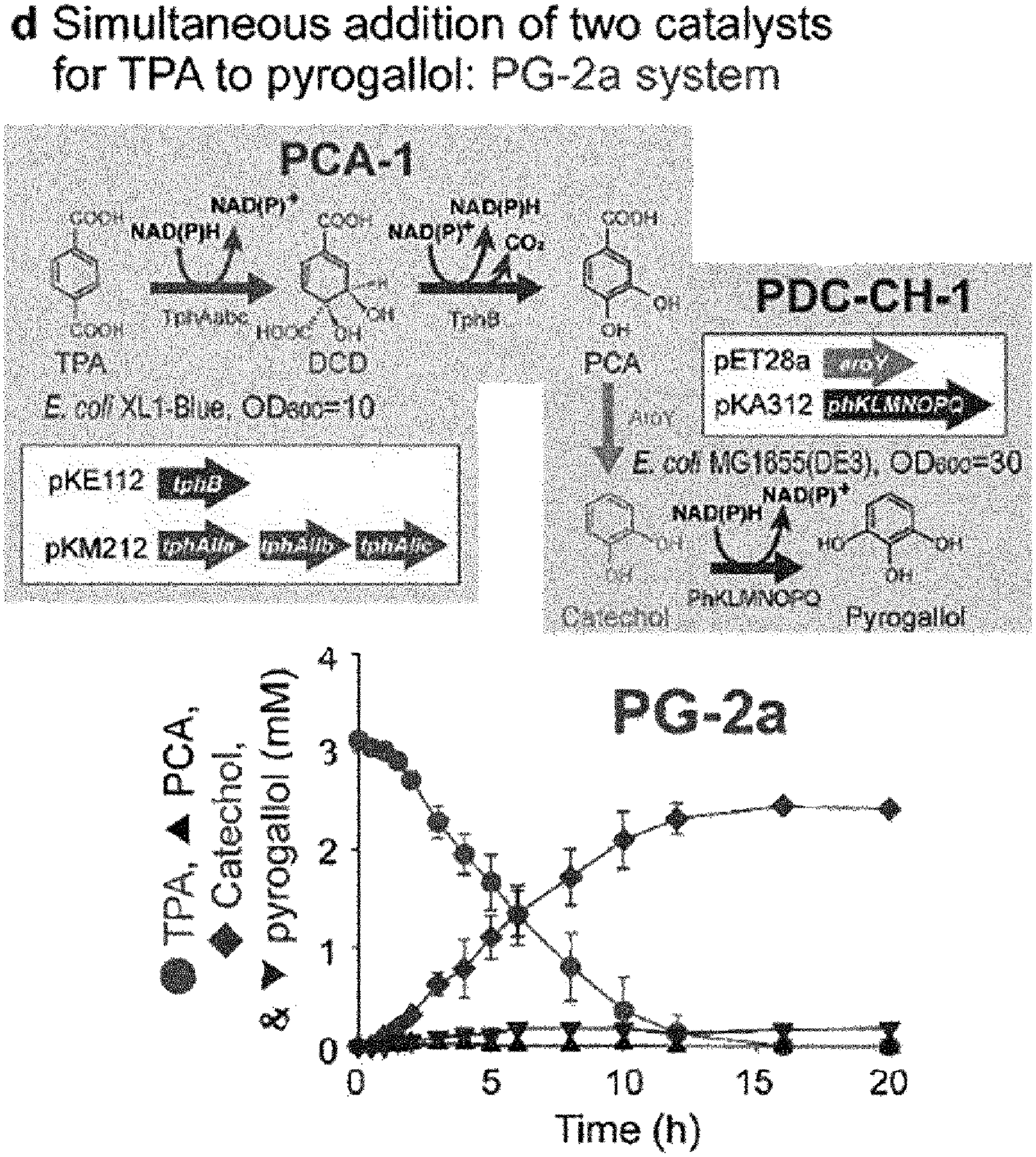
Figure 9E:
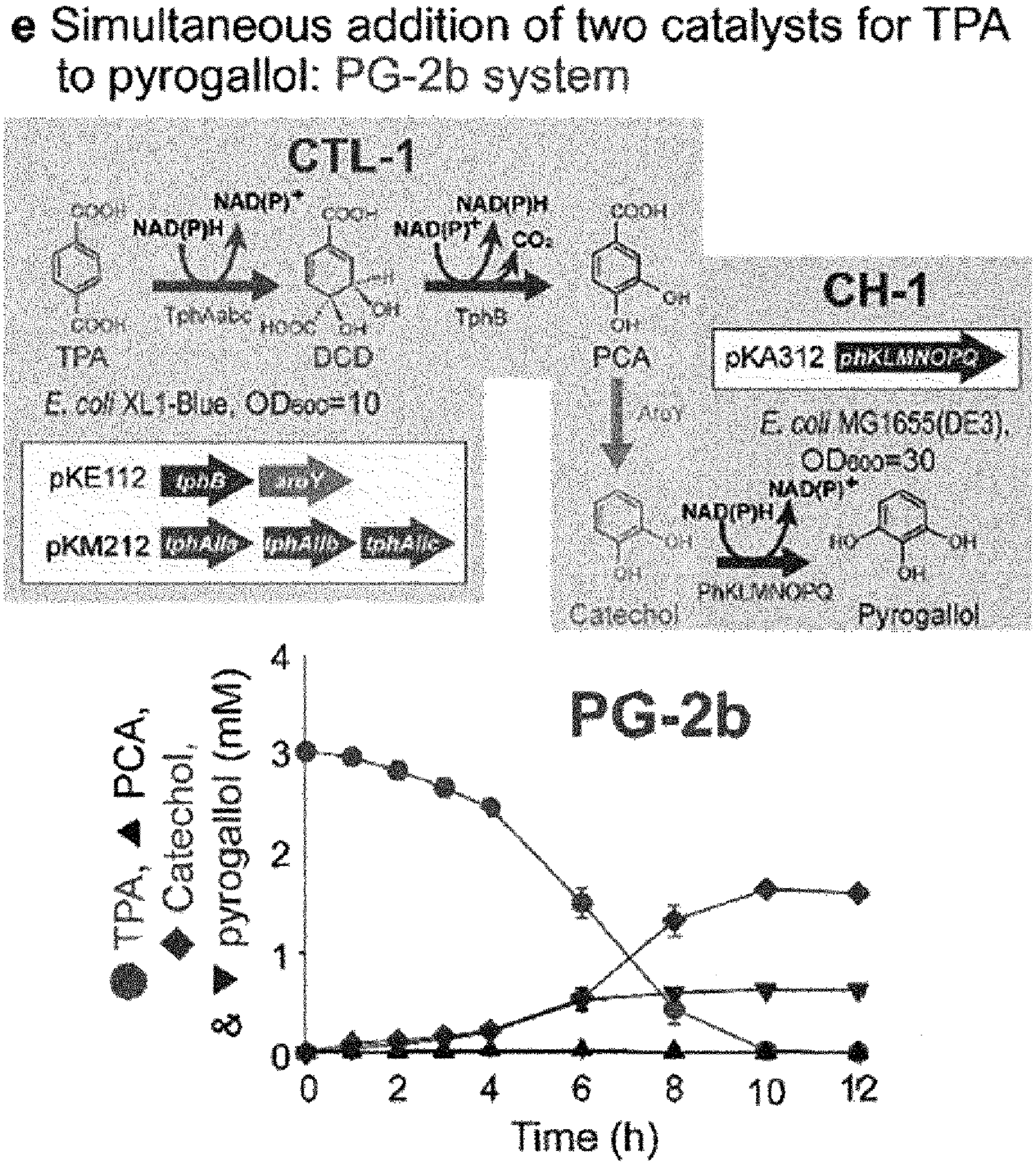
Figure 11C:
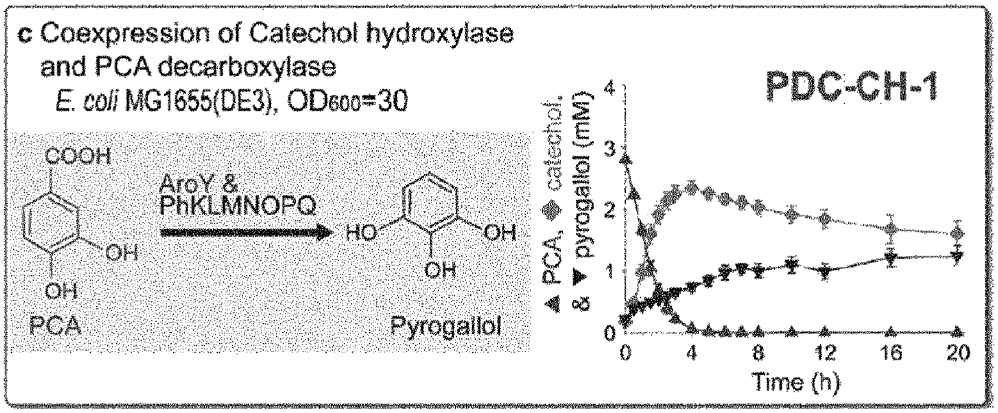

Next, in the PG-2a system, when the PCA synthesis strain PCA-1 and the PCA-to-pyrogallol conversion strain PDC-CH-1 expressing AroY and PhKLMNOPQ were simultaneously incubated with 3.1 mM TPA, only 0.2 mM pyrogallol was produced, but 2.4 mM catechol remained unconverted after 20 hours in TG-2 buffer (FIG. 9D). To troubleshoot the PG-2a system, when strain PDC-CH-1 was tested alone with 3.2 mM PCA as a substrate, PCA seemed to be completely converted to catechol after 20 hours, but only 1.2 mM pyrogallol was produced from catechol at a molar yield of approximately 39.0% (FIG. 11C). This pyrogallol yield from catechol by the PDC-CH-1 strain was 1.7 times lower than the 2.6 mM pyrogallol produced by *E. coli* strain CH-1 expressing only PhKLMNOPQ after 24 hours (FIGS. 11A and 11C). These results indicate that the expression of PhKLMNOPQ alone was advantageous for the conversion of catechol to pyrogallol. This may have been due to the uncertainty in generating the correct form of multiunit PhKLMNOPQ composed of PhK, $Ph(LNO)_2$, PhP, PhQ, and PhM subunits when co-expressed with AroY. Therefore, the PGA-2a system consisting of strains PCA-1 and PDC-CH-1 was replaced with the PG-2b system (FIG. 8B) consisting of *E. coli* strain CTL-1 expressing AroY, TphAabc, and TphB and *E. coli* strain CH-1 expressing PhKLMNOPQ alone (FIG. 9E). Pyrogallol production by the PG-2b system (i.e., 0.6 mM) was three times higher than that by the PG-2a system (i.e., 0.2 mM); this is likely attributed to the singular expression of PhKLMNOPQ. However, a substantial amount of catechol, 1.6 mM, remained unconverted (FIG. 9E).

<Experimental Example 6> Bioconversion of TPA to MA

Figure 4D:
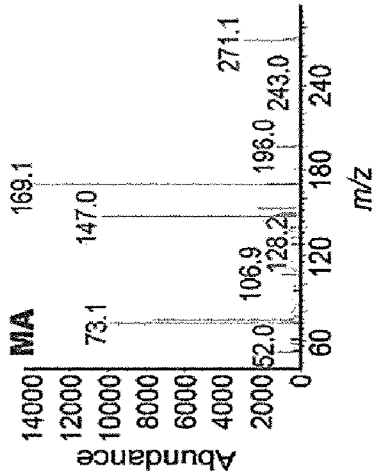
Figure 12A:
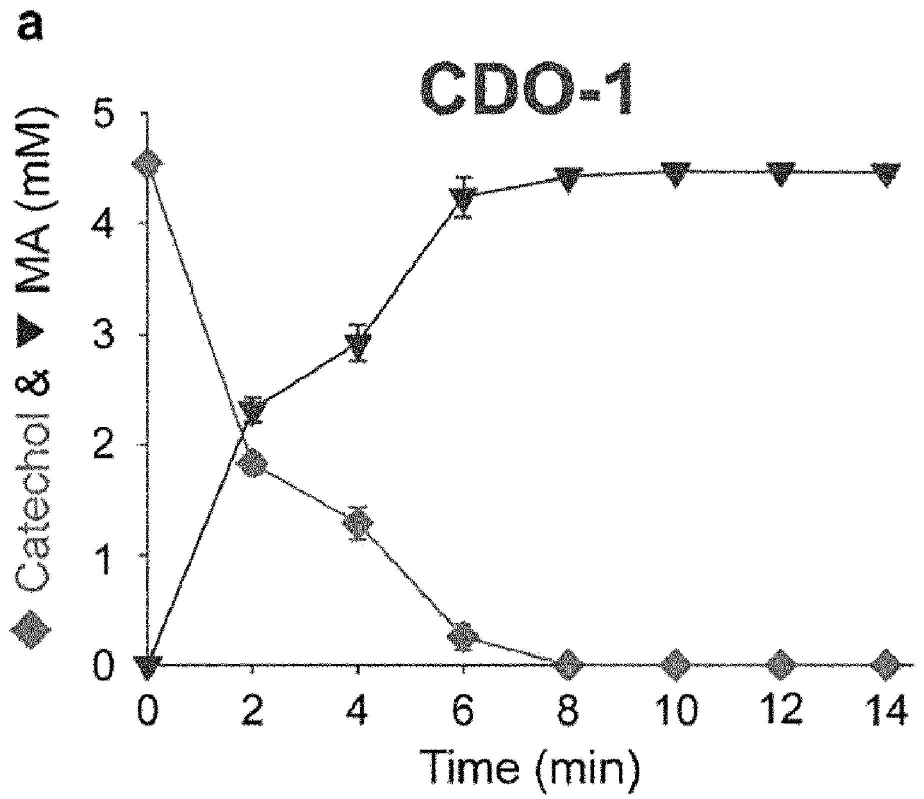
FIGS. 12A and 12B illustrate the bioconversion of TPA to MA by the ring cleavage of catechol.
Figure 12B:
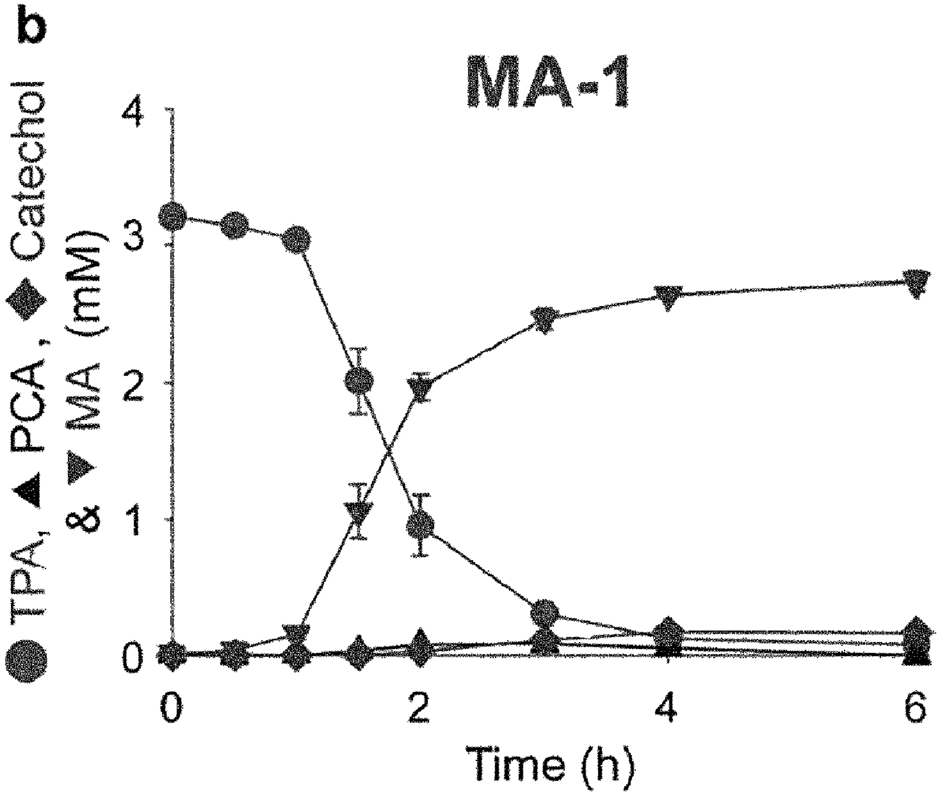

Catechol synthesized from TPA via PCA can be converted to MA by the ring cleavage of catechol. MA is currently used in the chemical industry to produce adipic acid, which is widely used to produce plastics. To develop an MA biosynthesis route from TPA, CatA, a catechol 1,2-dioxygenase originating from *P. putida* KT2440, was tested as the ring-cleavage module. When 4.5 mM catechol was incubated with *E. coli* strain CDO-1 expressing CatA, its complete conversion to MA occurred after 10 minutes (FIG. 12A). This MA synthesis module was combined with the catechol biosynthesis route of strain CTL-1 expressing TphAabc, TphB, and AroY (FIG. 9C) to construct *E. coli* strain MA-1 harboring the MA biosynthesis route beginning with TPA (FIG. 13C). The MA-1 system containing the MA-1 strain converted 3.2 mM TPA to 2.7 mM MA at a molar conversion yield of 85.4% after six hours without accumulating intermediates (FIGS. 12B and 13B). The biosynthesis route of TPA to PCA exhibited no redox imbalances (FIG. 13A). GC/MS confirmed that Ma was produced by strain MA-1 (FIGS. 4D and 13C).

<Experimental Example 7> Bioconversion of TPA to VA using Single-Catalyst Systems VA is used as the direct precursor of vanillin in the pharmaceutical industry. PCA is converted to VA by an OMT both in vitro and in vivo. To supply a methyl group to this O-methylation reaction catalyzed by an OMT, SAM is used as a co-substrate, and the adenosyl and methyl groups are supplied from ATP and methionine, respectively. Currently known OMTs are derived from eukaryotes; however, in the present invention, the expression of OMTs from various sources was tested in *E. coli* BL21 (DE3) to construct a VA synthesis module. Among the three OMTs examined in the present invention, HsOMT from *H. sapiens,* SlOMT from *Solanum lycopersicum,* and MsOMT from *M. sativa,* only HsOMT and SlOMT were expressed in active forms (FIG. 14A). Whole-cell conversions by *E. coli* strains OMT-1a and OMT-1b expressing HsOMT and SlOMT, respectively, were compared. By strain OMT-1a, 3.2 mM PCA was converted to 1.0 mM VA at a molar yield of 29.4% (FIG. 14B) in 0.1 M phosphate buffer supplemented with 20 and 10 g/L peptone containing 0.94 and 0.54 mM methionine, respectively; wherein a yield by strain OMT-1a was 1.4 times higher than that by strain OMT-1b (FIG. 14C). Therefore, HsOMT was selected for the synthesis module for PCA conversion to VA in further experiments.

Figure 15A:
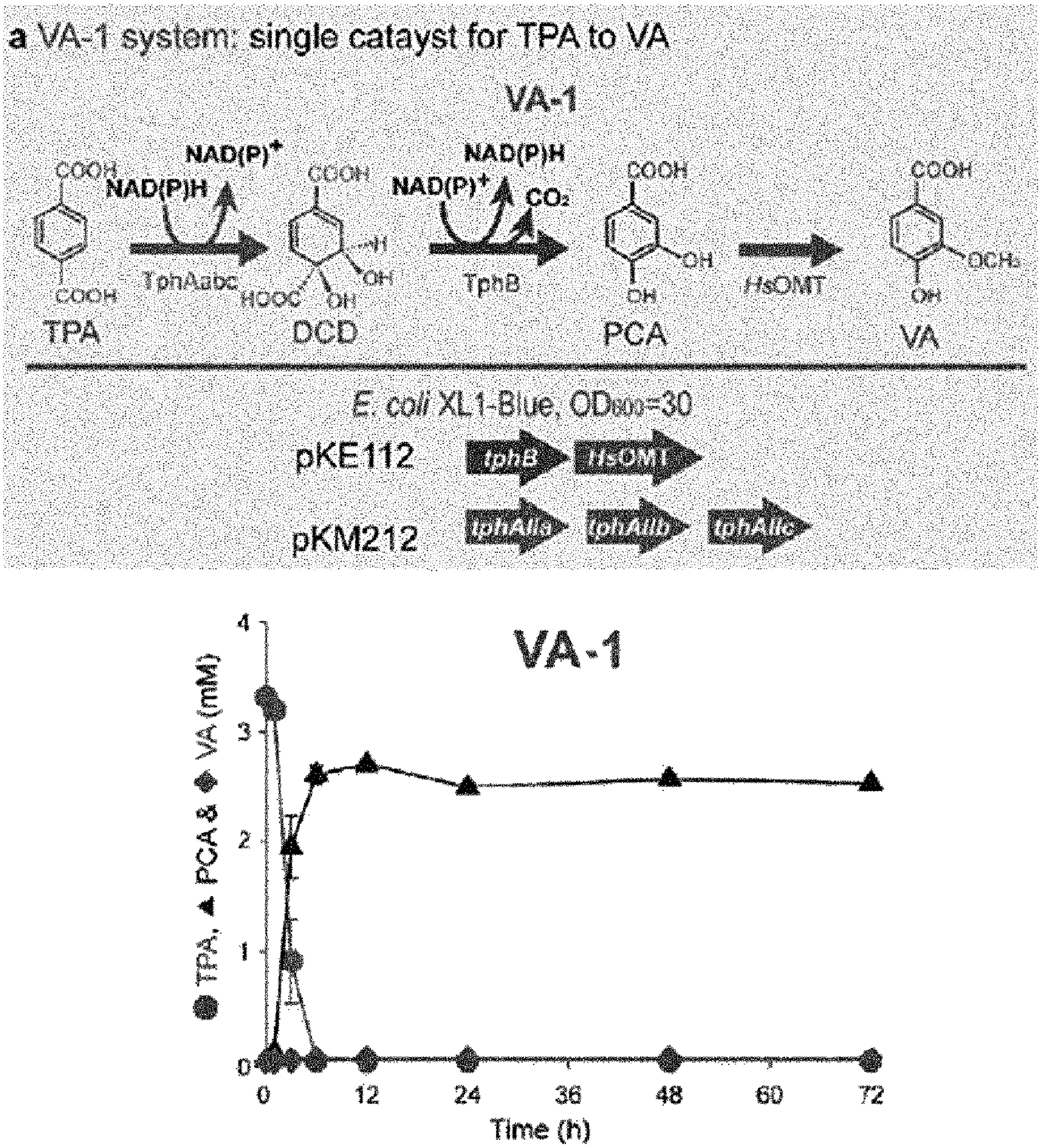
FIGS. 15A to 15D illustrate the bioconversion of TPA to VA.

To produce VA directly from TPA via PCA, the biosynthesis route of TPA to PCA was connected to the PCA to VA route using HPAOM by constructing *E. coli* strain VA-1 expressing TphAabc, TphB, and HsOMT (FIG. 19A). When 3.3 mM TPA was incubated with strain VA-1, TPA was completely consumed; however, only 0.02 mM VA was produced, and 2.3 mM PCA accumulated after 72 hours in TG-1/YP buffer (FIG. 15A). This low conversion of PCA to VA was confirmed by the poor consumption of glycerol (FIG. 16A) and methionine (FIG. 16B). This low conversion yield may be attributed to the low soluble expression of HsOMT (FIG. 14A).

Figure 17A:
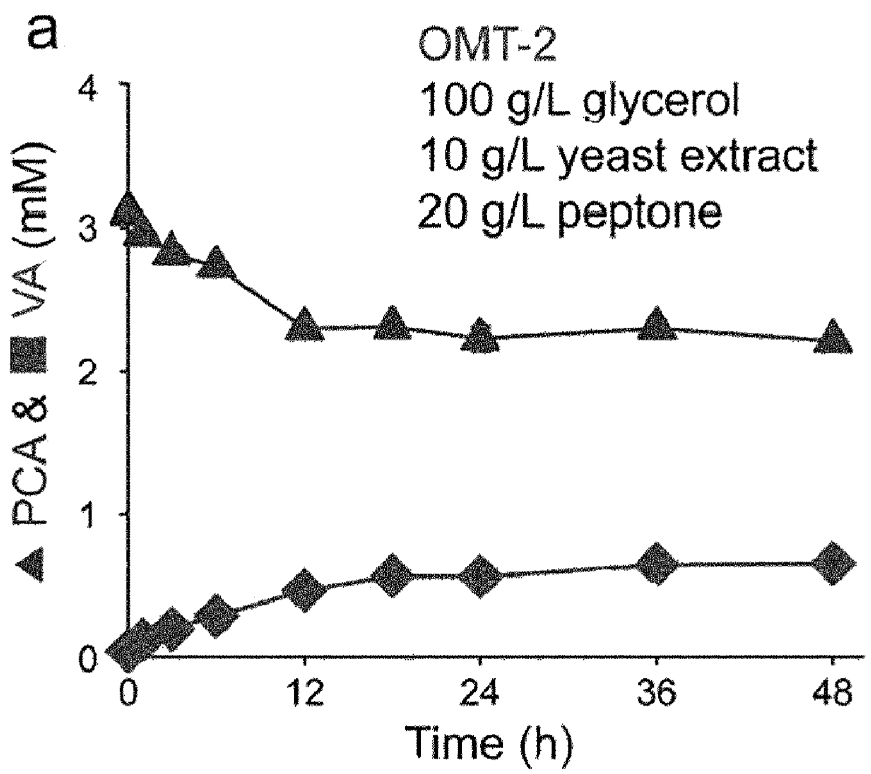
FIGS. 17A and 17B illustrate the effect of HsOMT protein engineering on the bioconversion of PCA to VA.
Figure 17B:
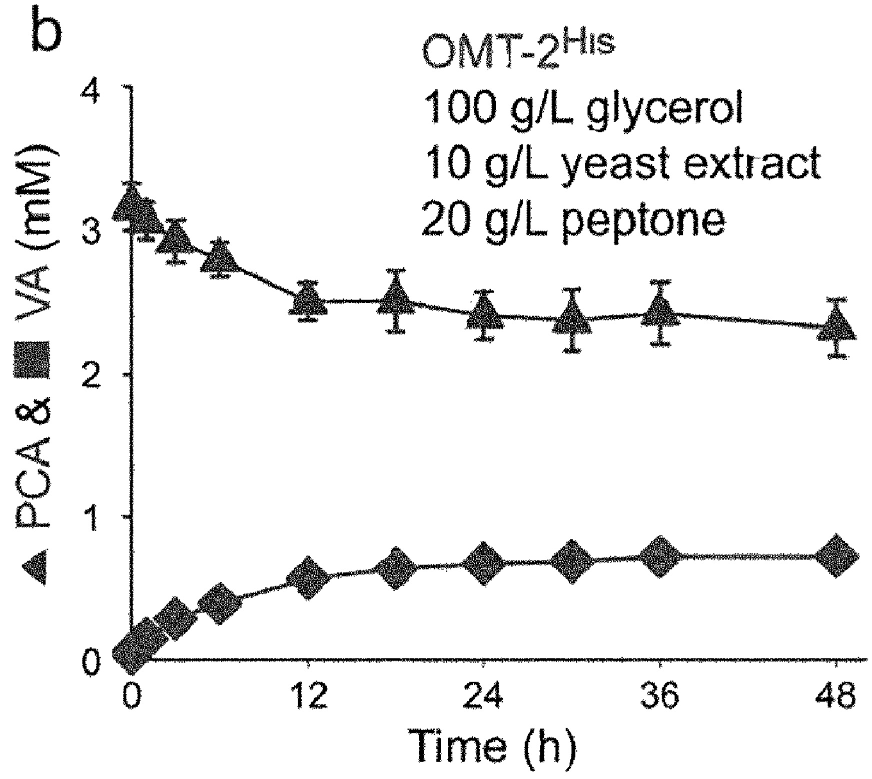

To improve the low PCA conversion to VA by strain VA-1 (FIG. 15A), the protein solubility of HsOMT was increased by the attachment of hexameric histidine to the N-terminus of HsOMT, which is known to increase protein solubility. Although strain OMT-2 expressing wild-type HsOMT produced 0.65 mM VA (FIG. 17A), strain OMT-2$^{His}$ expressing HsOMT$^{His}$ with the N-terminal hexameric histidine exhibited 10.7% higher VA production than the strain wild-type HsOMT (FIGS. 17A and 17B). Therefore, HsOMT$^{His}$ was used in further experiments.

Figure 18A:
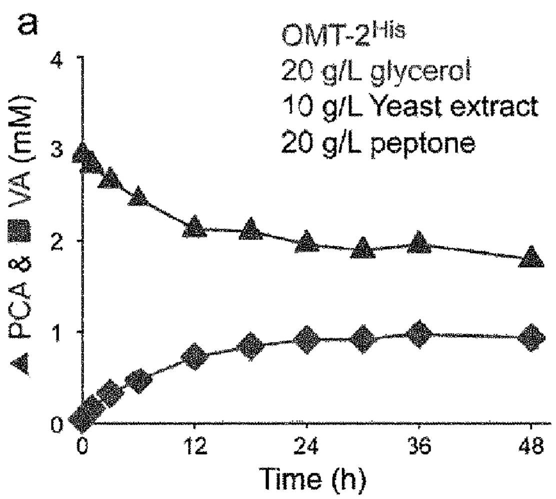
FIGS. 18A and 18B illustrate the effect of methionine supplementation on the bioconversion of PCA to VA.
Figure 18B:
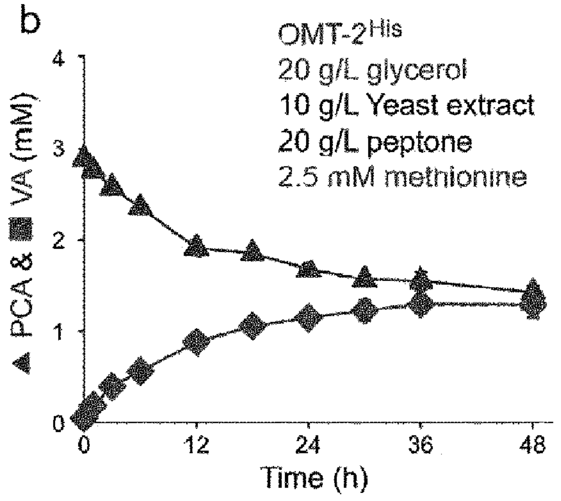

To further improve the low conversion of PCA to VA, conversion conditions were optimized using strain OMT-2$^{His}$. In particular, since endogenous SAM regeneration may be inefficient, it was promoted by supplementing methionine in TG-2/YPM buffer. When strain OMT-2$^{His}$ was incubated in TG-2/YP buffer lacking supplemented methionine, only 0.9 mM VA was produced from 2.9 mM PCA after 48 hours (FIG. 18A). Since TG-2/YP buffer contains only 0.8 mM free methionine from yeast extract and peptone, 2.5 mM methionine was added to the TG-2/YPM buffer to balance the methionine molar concentration with that of PCA. As a result, the molar yield of VA from 2.9 mM PCA by strain OMT-2$^{His}$ in TG-2/YPM buffer was 44.5%, which was 40.0% higher than that in TG-2/YP buffer (FIG. 18B).

Figure 4E:
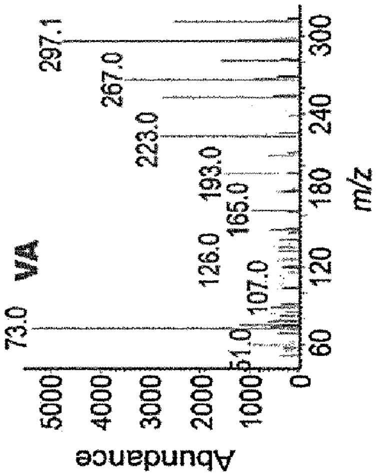
Figure 15B:
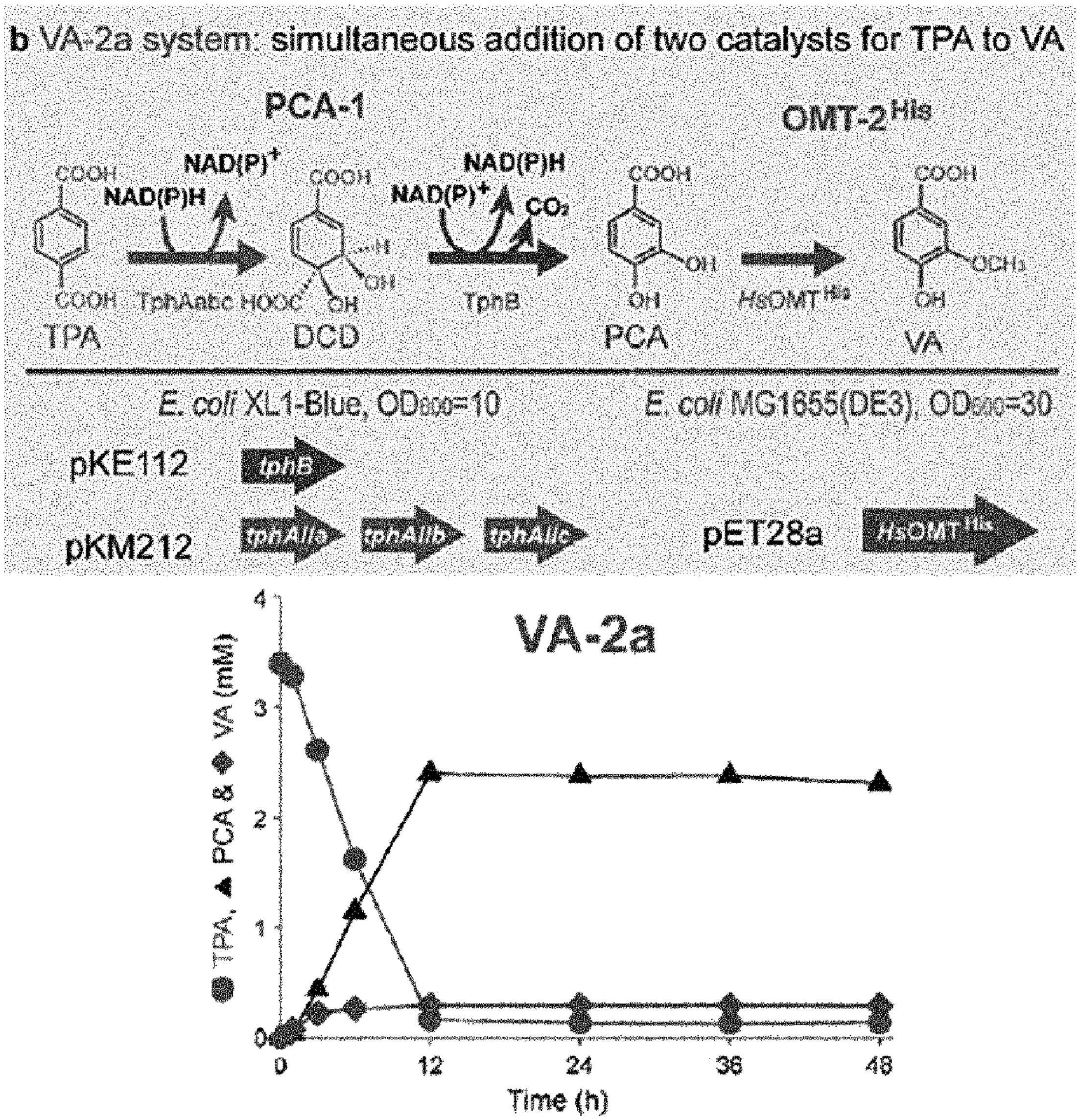
Figure 15C:
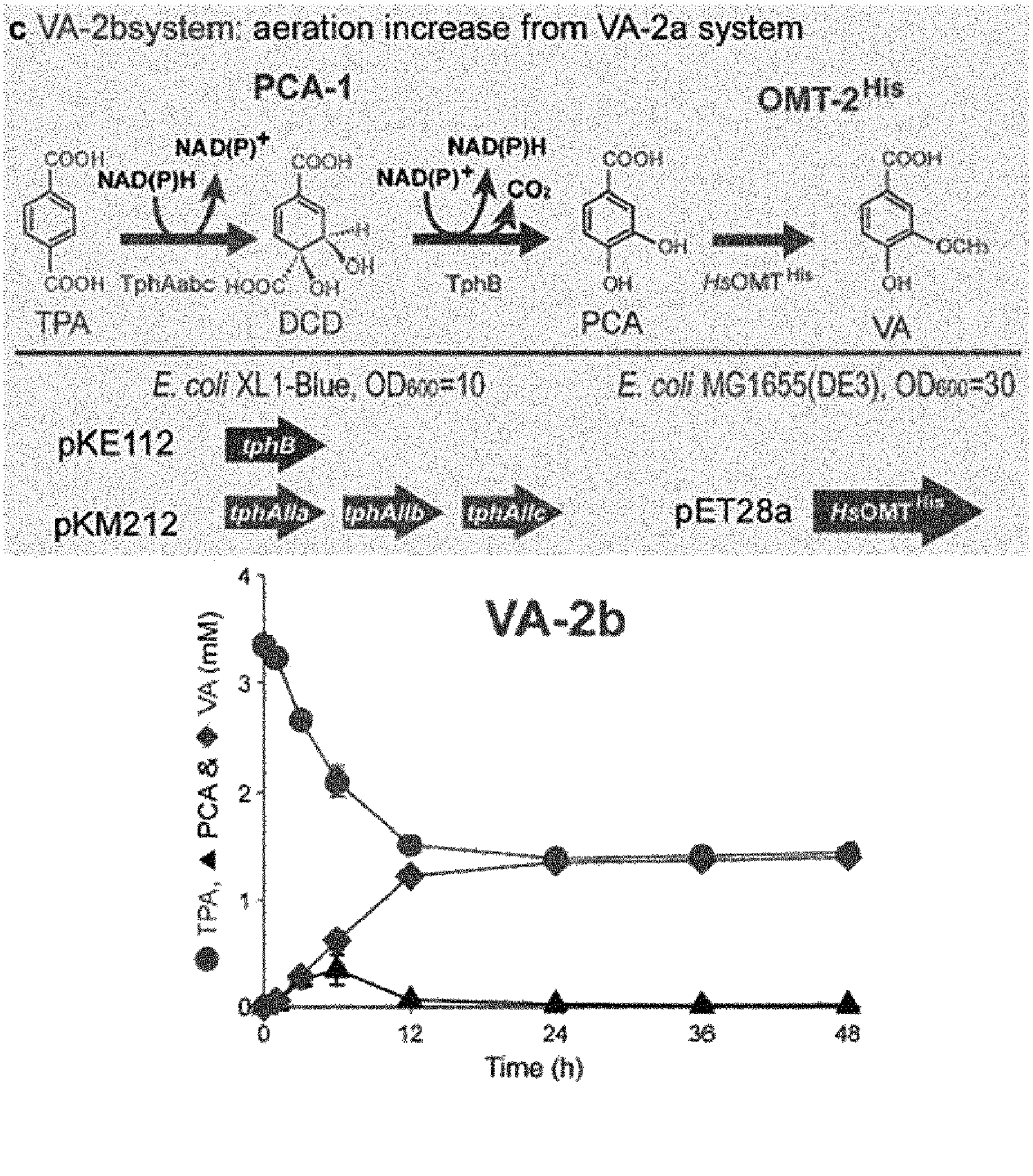

<Experimental Example 8> Bioconversion of TPA to VA using Double-Catalyst Systems In the single-catalyst system, PCA was accumulated due to the negligible conversion of PCA to VA. To bolster the conversion of PCA to VA, the present inventors developed the double-catalyst VA-2a system in which strain PCA-1 expressing TphAabc and TphB and strain OMT-2$^{His}$ expressing HsOMT$^{His}$ (FIG. 15B) and having different $OD_{600}$ values of 10 and 30, respectively, were simultaneously added into TG-2/YPM buffer containing TPA (FIG. 19A). As a result, VA produced from 3.4 mM TPA by the VA-2a system increased to 0.3 mM after 48 hours (FIGS. 15A and 15B), but the molar yield of VA from PCA converted from TPA remained at 6.4% (FIG. 19B). To further increase the conversion of PCA to VA, O-methylation catalyzed by HsOMT$^{His}$ was enhanced by increasing oxygen supply because adenosyl groups necessary for O-methylation may be supplied from ATP. To increase ATP generation by improving aeration, the VA-2b system used baffled flasks in place of the conical tubes used for the VA-2a system (FIG. 19A). As a result, VA produced by VA-2b after 48 hours increased to 1.4 mM VA at a molar yield of 41.6% (FIG. 15C), which was 4.7 times higher than that produced by the VA-2a system using conical tubes (FIGS. 15C and 15B). This enhanced VA production due to increased aeration was correlated with increased glycerol and methionine consumption (FIGS. 16A to 16D). Therefore, aeration is critical for increasing VA consumption from PCA because glycerol is efficiently metabolized to generate ATP, thus accelerating SAM synthesis from methionine by supplying S-adenosyl groups. VA production by the VA-2b system was confirmed by GC/MS (FIGS. 19C and 4E). These results imply that SAM regeneration by the improved supply of methionine and adenosyl groups from ATP is critical for O-methylation of PCA by an OMT.

Figure 15D:
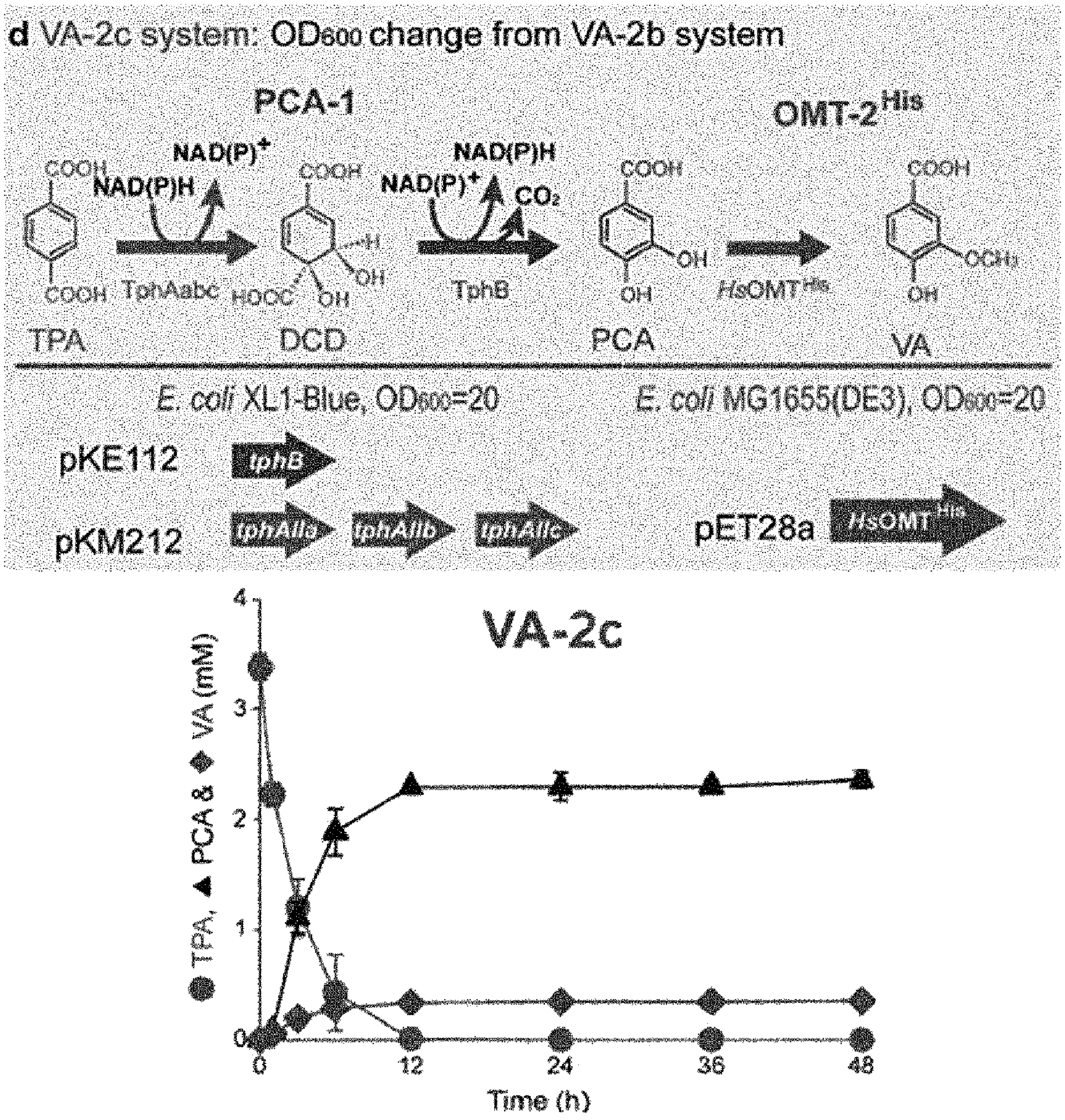

In the VA-2b system, however, 1.4 mM TPA remained unconverted (FIG. 15C). TPA conversion to PCA was increased to address this issue by adjusting the $OD_{600}$ values of strains PCA-1 and OMT-2$^{His}$ in the VA-2b system from 10 to 20 and 30 to 20, respectively. However, VA production after 48 hours decreased to 0.4 mM VA while TPA was completely consumed (FIG. 15D). To increase the conversion of TPA to VA, the flux of conversion of TPA to PCA and PCA to VA requires further optimization.

<Experimental Example 9> Bioconversion of EG to GLA

Figure 1E:
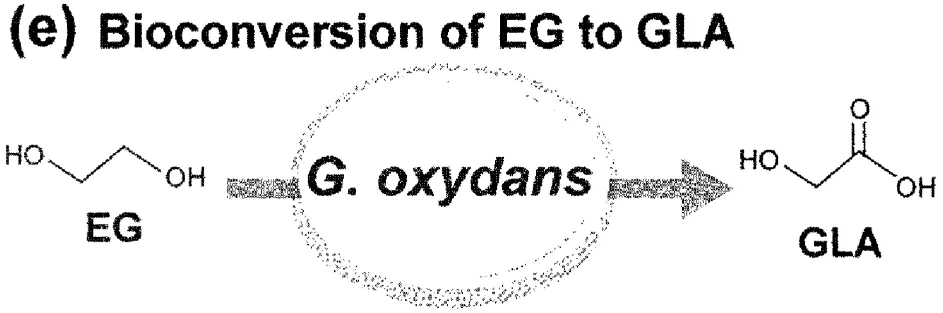
Figure 1F:
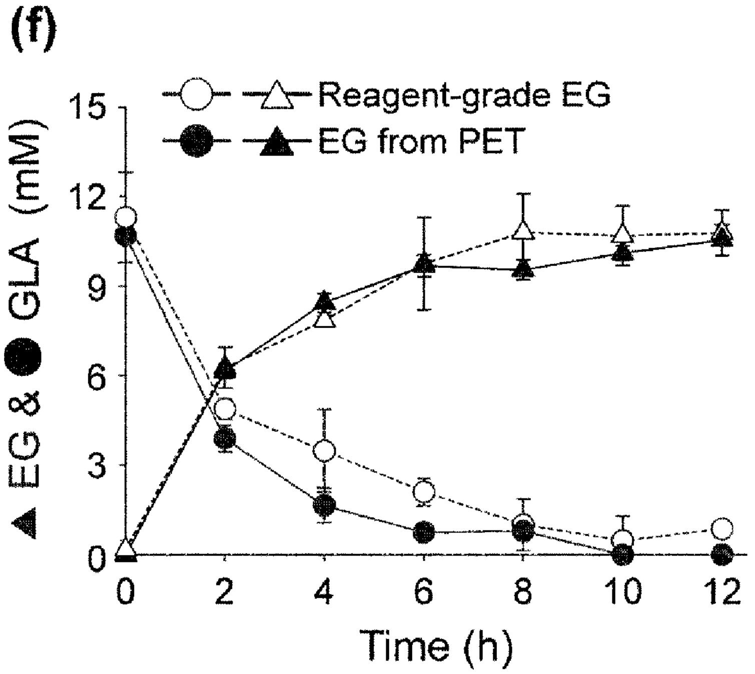
Figure 1G:
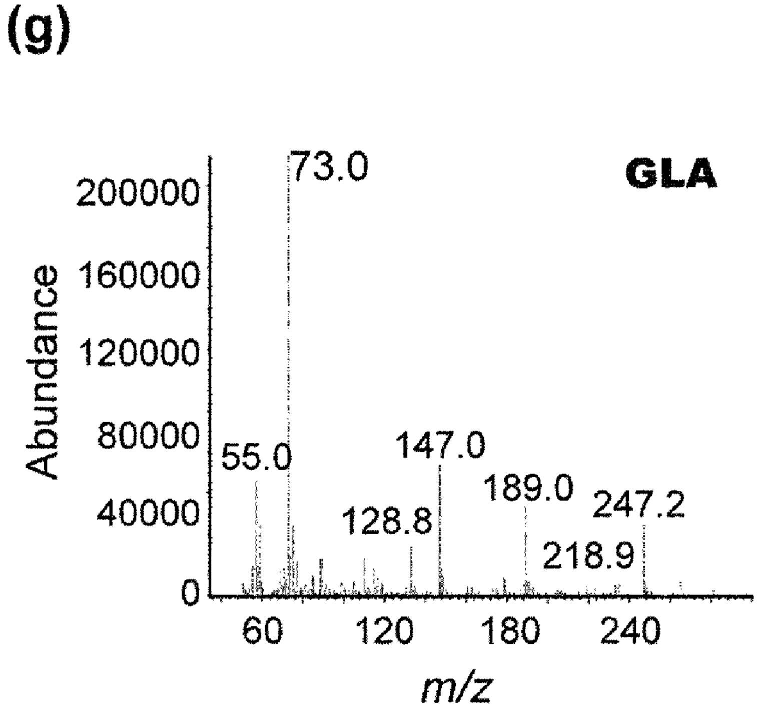
Figure 4F:
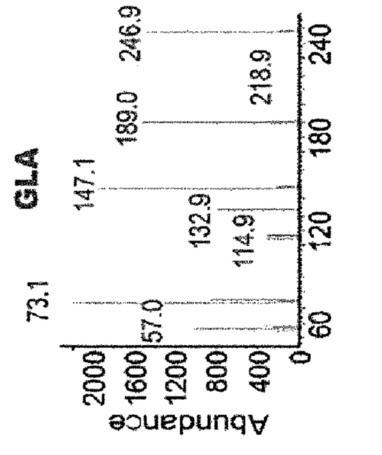

To experimentally validate the applicability of EG from waste PET as a feedstock, an EG sample obtained from the PET hydrolysate was tested using *G. oxydans* KCCM 40109 to produce GLA (FIGS. 1E and 20). GLA is used as an exfoliant in cosmetics. Reagent-grade samples containing 11.3, 28.6, and 67.6 mM EG were converted to GLA after 12 hours with molar yields of 95.3, 99.7, and 89.4%, respectively (FIGS. 20B and 20C). The sample containing 10.7 mM EG from the PET hydrolysate was converted to GLA with a molar yield of 98.6% after 12 hours (FIG. 1F). GLA production by *G. oxydans* was confirmed by GC/MS (FIGS. 1G and 4F).

The present invention is applicable to the field of PET upcycling.

What is claimed is:

1. A method of producing pyrogallol from polyethylene terephthalate, comprising:

producing terephthalic acid and ethylene glycol through hydrolysis of polyethylene terephthalate, wherein the hydrolysis of polyethylene terephthalate is performed by applying microwaves; and producing pyrogallol through sequential bioconversion of the terephthalic acid to 1,2-dihydroxy-3,5-cylcohexadiene-1,4-dicarboxylate, protocatechuic acid, catechol, and pyrogallol in the presence of a biocatalyst, wherein the terephthalic acid is bioconverted to catechol using a first microorganism expressing terephthalic acid 1,2-dioxygenase, 1,2-dihydroxy-3,5-cyclohexadiene-1,4-dicarboxylate dehydrogenase, and protocatechuic acid decarboxylase as a biocatalyst, and the catechol is bioconverted to pyrogallol using a second microorganism expressing phenol hydroxylase as a biocatalyst, wherein the second microorganism expresses phenol hydroxylase (PhKLMNOPQ) collectively encoded by the nucleic acid sequences of SEQ ID Nos: 12 to 18.

2. The method of claim 1, wherein the first microorganism expresses terephthalic acid 1,2-dioxygenase (TphAabc) collectively encoded by the nucleic acid sequences of SEQ ID NOs: 1 to 3, 1,2-dihydroxy-3,5-cyclohexadiene-1,4-dicarboxylate dehydrogenase (TphB) encoded by the nucleic acid sequence of SEQ ID NO: 4, and protocatechuic acid decarboxylase (AroY) encoded by a nucleic acid sequence of SEQ ID NO: 10.

* * * * *

SEQUENCE LISTING

```
<160> NUMBER OF SEQ ID NOS: 35

<210> SEQ ID NO 1
<211> LENGTH: 1011
<212> TYPE: DNA
<213> ORGANISM: Artificial Sequence
<220> FEATURE:
<223> OTHER INFORMATION: tphAa

<400> SEQUENCE: 1

atgaaccacc agatccatat ccacgactcc gatatcgcgt tcccctgcgc gcccgggcaa      60

tccgtactgg atgcagctct gcaggccggc atcgagctgc cctattcctg ccgcaaaggt     120

agctgtggca actgtgcgag tacgctgctc gacggaaata ttgcctcctt caatggcatg     180

gccgtgcgaa acgaactctg cgcctcggaa caagtgctgc tgtgcggctg cactgcagcc     240

agcgatatac gtatccaccc gagctccttt cgccgtctcg acccggaagc ccgaaaacgt     300
```

```
tttacggcca aggtgtacag caatacactg gcggcacccg atgtctcgct gctgcgcctg    360

cgcctgcctg tgggcaagcg cgccaaattt gaagccggcc aatacctgct gattcacctc    420

gacgacgggg aaagccgcag ctactctatg gccaatccac cccatgagag cgatggcatc    480

acattgcatg tcaggcatgt acctggtggt cgcttcagca ctatcgttca gcagttgaag    540

tctggtgaca cattggatat cgaactgcca ttcggcagca tcgcactgaa gcctgatgac    600

gcaaggcccc tgatttgcgt tgcgggtggc acgggatttg cgcccattaa atccgttctt    660

gatgacttag ccaaacgcaa ggttcagcgc gacatcacgc tgatctgggg ggctcgcaac    720

ccctcgggcc tgtatcttcc tagcgccatc gacaagtggc gcaaagtctg gccacagttt    780

cgctacattg cagccatcac cgacctaggc gatatgcctg cggatgctca cgcaggtcgg    840

gtggatgacg cgctacgcac tcactttggc aacctgcacg atcatgtggt gcactgctgt    900

ggctcaccag ctctggttca atcagtgcgc acagccgctt ccgatatggg cctgcttgca    960

caggacttcc acgcggatgt ttttgcgaca ggcccgactg gtcaccacta g            1011
```

```
<210> SEQ ID NO 2
<211> LENGTH: 1242
<212> TYPE: DNA
<213> ORGANISM: Artificial Sequence
<220> FEATURE:
<223> OTHER INFORMATION: tphAb

<400> SEQUENCE: 2
```

```
atgcaagaat ccatcatcca gtggcatggg gccactaata cgcgcgtgcc ttttggtatc     60

tataccgaca cagccaatgc tgatcaggaa cagcagcgca tctatcgcgg cgaggtctgg    120

aactacttgt gcctggaatc tgaaattccc ggggccggtg atttccgcac tacctttgcc    180

ggtgaaacac cgatagttgt cgtacgggat gccgaccagg aaatctacgc cttcgagaac    240

cgctgcgcgc atcgcggcgc tctcatcgct ctggagaaat cgggccgtac ggatagtttc    300

cagtgcgtct atcacgcctg gagctacaac cgacagggag atctgaccgg cgttgccttc    360

gagaaaggtg tcaagggcca gggtggcatg ccggcctcat tctgcaaaga agagcatggc    420

ccgcgcaagc tccgcgtggc tgtcttttgc ggtttggtct ttggcagttt ttccgaggac    480

gtgcccagca ttgaggatta ccttggccct gagatttgcg agcgcataga gcgcgtgctg    540

cacaagcccg tagaagtcat cggtcgcttc acgcaaaagc tgcctaacaa ctggaagctc    600

tacttcgaga acgtgaagga cagctatcac gccagcctcc tgcatatgtt cttcaccacc    660

ttcgagctga atcgcctctc acaaaaaggc ggtgtcatcg tcgacgagtc gggtggccac    720

catgtgagct attccatgat cgatcgcggc gccaaagacg actcgtacaa ggaccaggcc    780

atccgctccg acaacgagcg ttaccggctc aaagatccta gccttctaga gggctttgag    840

gagttcgagg acggcgtgac cctgcagatc ctttctgtgt tccctggctt tgtgctgcag    900

cagattcaga acagcatcgc cgtgcgtcag ttgctgccca agagcatctc cagctcggaa    960

ctcaactgga cctatcttgg ctatgcagat gacagtgccg agcaacgcaa ggtcagactc   1020

aaacaggcca accttatcgg cccggccgga ttcatttcca tggaagacgg agctgtcggt   1080

ggattcgtgc agcgtggcat cgcaggcgct gccaaccttg atgcagtcat cgagatgggc   1140

ggagaccacg aaggctctag cgagggccgc gccacggaaa cctcggtacg cggcttttgg   1200

aaggcctacc gcaagcatat gggacaggag atgcaagcat ga                      1242
```

```
<210> SEQ ID NO 3
```

<211> LENGTH: 465
<212> TYPE: DNA
<213> ORGANISM: Artificial Sequence
<220> FEATURE:
<223> OTHER INFORMATION: tphAc

<400> SEQUENCE: 3
atgatcaatg aaattcaaat cgcggccttc aatgccgcct acgcgaagac catagacagt 60
gatgcaatgg agcaatggcc aaccttttc accaaggatt gccactattg cgtcaccaat 120
gtcgacaacc atgatgaggg acttgctgcc ggcattgtct gggcggattc gcaggacatg 180
ctcaccgacc gaatttctgc gctgcgcgaa gccaatatct acgagcgcca ccgctatcgc 240
catatcctgg gtctgccttc gatccagtca ggcgatgcaa cacaggccag cgcttccact 300
ccgttcatgg tgctgcgcat catgcataca ggggaaacag aggtctttgc cagcggtgag 360
tacctcgaca aattcaccac gatcgatggc aagttacgtc tgcaagaacg catcgcggtt 420
tgcgacagca cggtgacgga cacgctgatg gcattgccgc tatga 465

<210> SEQ ID NO 4
<211> LENGTH: 948
<212> TYPE: DNA
<213> ORGANISM: Artificial Sequence
<220> FEATURE:
<223> OTHER INFORMATION: tphB

<400> SEQUENCE: 4
atgacaatag tgcaccgtag attggctttg gccatcggcg atccccacgg tattggccca 60
gaaatcgcac tgaaagctct ccagcagctg tctgtcaccg aaaggtctct tatcaaggtc 120
tatggacctt ggagcgctct cgagcaagcc gcacgggttt gcgaaatgga gccgcttctt 180
caagacatcg ttcacgagga agccggcaca cttacacaac cagttcaatg gggagaaatc 240
accccgcagg ctggtctatc tacggtgcaa tccgcaacag cggctatccg agcgtgcgaa 300
aacggcgaag tcgatgccgt cattgcctgc cctcaccatg aaacggccat tcaccgcgca 360
ggcatagcgt tcagcggcta cccatctttg ctcgccaatg ttcttggcat gaacgaagac 420
caggtattcc tgatgctggt gggggctggc ctgcgcatag tgcatgtcac tttgcatgaa 480
agcgtgcgca gcgcattgga gcggctctct cctcagttgg tggtcaacgc ggcgcaggct 540
gccgtgcaga catgcacctt actcggagtg cctaaaccaa aagtcgctgt attcgggatc 600
aaccctcatg catctgaagg acagttgttc ggcctggagg actcccagat caccgttccc 660
gctgtcgaga cactgcgcaa gcgcggccta gcagtagacg gccccatggg agctgacatg 720
gttctggcac agcgcaagca cgacctgtat gtagccatgc tgcacgatca gggccatatc 780
cccatcaagc tgctggcacc taacggagcc agcgcactat ctatcggtgg cagggtggtg 840
ctttccagcg tgggccatgg cagcgccatg gacattgccg gccgtggcgt ggctgacgcc 900
acggccctcc tacgcacaat agccctactc ggagcccaac cggtctga 948

<210> SEQ ID NO 5
<211> LENGTH: 1095
<212> TYPE: DNA
<213> ORGANISM: Artificial Sequence
<220> FEATURE:
<223> OTHER INFORMATION: SlOMT

<400> SEQUENCE: 5
atgggatcga cagcaaatat ccagttagca acacaatcgg aagacgaaga gcgtaattgc 60
acgtacgcca tgcaactact ctcatcgtca gtgcttccct tcgttttgca ctcaactatc 120

```
caattggatg tttttgacat actcgcaaaa gataaagccg ccactaaact atctgcttta    180
gaaattgtgt ctcacatgcc taactgtaag aaccctgatg ccgctaccat gctagaccgg    240
atgctttatg tcctagctag ttattcttta ctcgattgct cggttgttga agagggaaat    300
ggggtgaccg aaaggcgcta tggtctgtca cgagtgggga aatttttgt acgtgatgaa     360
gatggtgcat ccatgggacc attgttggct ttgcttcaag ataaagtatt cattaacagc    420
tggtttgaac taaaagatgc agtacttgaa ggtggagttc catttgacag ggtgcatggt    480
gtacatgcat ttgaatatcc aaaattggac ccaaagttca atgatgtttt caaccaggca    540
atgataaacc acacaactgt tgtcatgaaa agaatacttg aaaattacaa aggttttgag    600
aatctcaaaa ctttggttga tgttggaggt ggtcttggtg ttaatctcaa gatgattaca    660
tctaaatacc ccacaattaa gggcactaat tttgatttgc ctcatgttgt tcaacatgca    720
ccttcctatc ctggggtgga tcatgttggg ggagatatgt ttgaaagtgt tccacaagga    780
gatgctattt ttatgaagtg gattcttcat gactggagtg atggtcactg cctcaaattg    840
ctgaagaact gtcataaggc tctaccggac aacggaaagg tgattgttgt ggaggccaat    900
ctaccagtga aacctgatac tgataccaca gtggttggag tttcacaatg tgatttgatc    960
atgatggctc agaatcccgg aggtaaagag cgttctgaac aggagtttcg ggcattggca   1020
agtgaagctg gattcaaagg tgttaaccta atatgttgtg tctgtaattt ttgggtcatg   1080
gaattttaca agtag                                                    1095
```

<210> SEQ ID NO 6
<211> LENGTH: 671
<212> TYPE: DNA
<213> ORGANISM: Artificial Sequence
<220> FEATURE:
<223> OTHER INFORMATION: HsOMT

<400> SEQUENCE: 6

```
atgggcgata ccaaagaaca gcgtattctg aatcatgttc tgcagcatgc cgaaccgggt     60
aatgcacaga gcgttctgga agcaattgat acctattgtg aacagaaaga atgggccatg    120
aatgtgggtg ataaaaaagg caaaattgtg gatgccgtga tccaagaaca tcagccgagc    180
gtgctgctgg aactgggtgc atattgtggt tatagcgcag ttcgtatggc acgtctgctg    240
agtccgggtg cacgtctgat taccattgaa attaacccgg attgtgcagc aattacccag    300
cgtatggttg attttgccgg tgttaaagat aaagttaccc tggttgttgg tgcaagccag    360
gatattattc cgcagctgaa aaaaaaatat gacgtggata ccctggatat ggtgtttctg    420
gatcattgga aagatcgtta tctgccggat accctgctgc tggaagaatg tggtctgctg    480
cgtaaaggca ccgttctgct ggcagataat gttatttgtc ctggtgcacc ggattttctg    540
gcacatgttc gtggtagcag ctgttttgaa tgtacccatt atcagtcctt tctggaatat    600
cgtgaagttg ttgatggtct ggaaaaagcc atctataaag gtccgggtag cgaagcaggt    660
ccgtaactta a                                                         671
```

<210> SEQ ID NO 7
<211> LENGTH: 1098
<212> TYPE: DNA
<213> ORGANISM: Artificial Sequence
<220> FEATURE:
<223> OTHER INFORMATION: MsOMT

<400> SEQUENCE: 7

```
atgggttcaa caggtgaaac tcaaataaca ccaacccaca tatcagatga agaagcaaac     60

ctcttcgcca tgcaactagc aagtgcttca gttcttccca tgattttgaa atcagctctt    120

gaacttgatc tcttagaaat cattgctaaa gctggacctg gtgctcaaat ttcacctatt    180

gaaattgctt ctcagctacc aacaactaac cctgatgcac cagttatgtt ggaccgaatg    240

ttgcgtctct tggcttgtta cataatcctc acatgttcag ttcgtactca acaagatgga    300

aaggttcaga gactttatgg tttggctact gttgctaagt atttggttaa gaatgaagat    360

ggtgtatcca tttctgctct taatctcatg aatcaggata aagtgctcat ggaaagctgg    420

tatcacctaa aagatgcagt ccttgatggg ggcattccat tcaacaaggc ttatggaatg    480

acagcctttg aataccatgg aacagatcca aggtttaaca aggttttcaa caaggggatg    540

tctgatcact ctaccatcac aatgaagaaa attcttgaga cctacacagg ttttgaaggc    600

cttaaatctc ttgttgatgt aggtggtggt actggagctg taattaacac gattgtctca    660

aaatatccca ctataaaggg tataaatttt gatttacccc atgtcattga agatgctcca    720

tcttatccag gagttgagca tgttggtgga gacatgtttg tcagtattcc aaaggctgat    780

gctgttttta tgaagtggat ttgtcatgac tggagtgatg agcactgctt gaaatttttg    840

aagaactgct atgaggcact gccagacaat ggaaaagtga ttgtggcaga atgcatactt    900

ccagtggctc cagattcaag cctggccaca aaaggtgtgg ttcacattga tgtgatcatg    960

ttggctcata atcctggtgg gaaagagaga acacaaaaag agtttgagga tcttgccaaa   1020

ggtgctggat tccaaggttt caaagtccat tgtaatgctt tcaacacata catcatggag   1080

tttcttaaga aggtttaa                                                 1098
```

<210> SEQ ID NO 8
<211> LENGTH: 1188
<212> TYPE: DNA
<213> ORGANISM: Artificial Sequence
<220> FEATURE:
<223> OTHER INFORMATION: pobA

<400> SEQUENCE: 8

```
atgaaaactc aggttgcaat tattggtgca ggtccgtctg gcctgctgct gggccagctg     60

ctgcacaagg ccggtatcga taacatcatc gtcgaacgcc agactgccga gtacgtacta    120

ggccgcatcc gcgccggggt gctagagcaa ggcacggtcg acctgctgcg cgaggctggc    180

gtggccgagc gcatggaccg tgaaggcctg gtgcacgagg gggttgaact gctggttggc    240

gggcgccgcc agcgtctgga tctcaaagcc ctgaccggcg gcaagacggt gatggtctac    300

ggccagaccg aagtcacccg tgacctgatg caggcccgcg aagccagtgg tgcgccgatc    360

atttattcag ccgccaacgt tcagccgcat gaattgaaag gcgagaagcc ctacctgacg    420

ttcgaaaagg atggccgggt gcagcggatt gactgcgact atatcgccgg ctgcgacggc    480

ttccacggta tctcgcggca gagcatcccg gagggcgtgc tgaaacagta tgagcgggtt    540

tacccgtttg gctggctggg cctgctgtcg gacacaccgc cagtcaatca cgagttgatc    600

tacgcccacc atgagcgcgg tttcgcgttg tgtagccaac gctcgcaaac acgcagccgc    660

tactatctgc aggtgccttt gcaggatcgg gtcgaggagt ggtctgacga gcgtttctgg    720

gacgaactga aagcccgtct gcccgccgag gtggcggcgg acctggtcac aggccccgcg    780

ttggaaaaaa gtattgcgcc gctgcgtagc ctggtggtcg aacccatgca gtatggtcac    840

ctgttcctgg tgggggacgc ggcgcacatc gtcccccccta cgggtgccaa aggccttaac    900

ctggcggcct ccgacgtcaa ctacctgtac cgcattctgg tcaaggtgta ccacgaaggg    960
```

```
cgcgtcgacc tgcttgcgca atactcgccg ctggcactgc gccgcgtgtg gaagggcgag   1020

cgcttcagct ggttcatgac ccaactgctg catgacttcg gtagccacaa ggacgcctgg   1080

gaccagaaga tgcaggaagc tgaccgcgag tacttcctga cctcgccggc gggcctggtg   1140

aacattgccg agaactatgt ggggctgccg ttcgaggaag ttgcctga                 1188


<210> SEQ ID NO 9
<211> LENGTH: 1188
<212> TYPE: DNA
<213> ORGANISM: Artificial Sequence
<220> FEATURE:
<223> OTHER INFORMATION: pobAMut

<400> SEQUENCE: 9

atgaaaactc aggttgcaat tattggtgca ggtccgtctg gcctgctgct gggccagctg     60

ctgcacaagg ccggtatcga taacatcatc gtcgaacgcc agactgccga gtacgtacta    120

ggccgcatcc gcgccggggt gctagagcaa ggcacggtcg acctgctgcg cgaggctggc    180

gtggccgagc gcatggaccg tgaaggcctg gtgcacgagg gggttgaact gctggttggc    240

gggcgccgcc agcgtctgga tctcaaagcc ctgaccggcg gcaagacggt gatggtctac    300

ggccagaccg aagtcacccg tgacctgatg caggcccgcg aagccagtgg tgcgccgatc    360

atttattcag ccgccaacgt tcagccgcat gaattgaaag gcgagaagcc ctacctgacg    420

ttcgaaaagg atggccgggt gcagcggatt gactgcgact atatcgccgg ctgcgacggc    480

ttccacggta tctcgcggca gagcatcccg gagggcgtgc tgaaacagta tgagcgggtt    540

tacccgtttg gctggctggg cctgctgtcg gacacaccgc cagtcaatca cgagttgatc    600

tacgcccacc atgagcgcgg tttcgcgttg tgtagccaac gctcgcaaac acgcagccgc    660

tactacctgc aagtgccttt gcaggatcgg gtcgaggagt ggtctgacga gcgtttctgg    720

gacgaactga aagcccgtct gcccgccgag gtggcggcgg acctggtcac aggccccgcg    780

ttggaaaaaa gtattgcgcc gctgcgtagc ctggtggtcg aacccatgca gtatggtcac    840

ctgttcctgg tgggggacgc ggcgcacatc gtcccccctg cgggtgccaa aggccttaac    900

ctggcggcct ccgacgtcaa ctacctgtac cgcattctgg tcaaggtgta ccacgaaggg    960

cgcgtcgacc tgcttgcgca atactcgccg ctggcactgc gccgcgtgtg gaagggcgag   1020

cgcttcagct ggttcatgac ccaactgctg catgacttcg gtagccacaa ggacgcctgg   1080

gaccagaaga tgcaggaagc tgaccgcgag tacttcctga cctcgccggc gggcctggtg   1140

aacattgccg agaactttgt ggggctgccg ttcgaggaag ttgcctga                 1188


<210> SEQ ID NO 10
<211> LENGTH: 1488
<212> TYPE: DNA
<213> ORGANISM: Artificial Sequence
<220> FEATURE:
<223> OTHER INFORMATION: aroY

<400> SEQUENCE: 10

atgcagaacc cgatcaacga cctgcgctcc gcgatcgcgc tgctgcaacg ccatccgggt     60

cactacatcg aaaccgacca cccggtcgac ccgaacgccg aactggccgg tgtgtaccgc    120

cacatcggtg cgggtggcac cgtgaaacgt ccgacccgca ccggtccagc catgatgttc    180

aacagcgtga agggctaccc aggcagccgc atcctggtgg gcatgcacgc cagccgtgaa    240

cgtgccgccc tgctgctggg ctgcgtgcca agcaaactgg cgcagcacgt gggccaggcc    300
```

-continued

```
gtgaagaacc cggtggcccc agtggtggtg ccagccagcc aagccccatg ccaagaacag    360
gtgttctacg ccgacgaccc ggacttcgac ctgcgcaagc tgctgccagc cccaaccaac    420
accccgatcg atgccggtcc gttcttctgc ctgggcctgg tgctggcgag cgacccggaa    480
gataccagcc tgaccgacgt gaccatccac cgcctgtgcg tgcaagagcg cgacgagctg    540
agcatgttcc tggccgccgg tcgccacatc gaggtgttcc gcaagaaggc cgaagccgcc    600
ggtaagccgc tgccggtgac catcaacatg ggcctggacc cagccatcta catcggtgcc    660
tgcttcgaag cgccaaccac cccgttcggc tacaacgagc tgggtgtggc cggtgccctg    720
cgtcagcaac cggtggaact ggtgcagggc gtggccgtga aagagaaggc gatcgcgcgt    780
gccgagatca tcatcgaggg cgaactgctg ccaggcgtgc gcgtgcgcga agatcagcac    840
accaacaccg gtcacgccat gccggaattc ccaggctact gcggtgaggc caacccgagc    900
ctgccggtga tcaaggtgaa ggccgtgacc atgcgcaacc acgccatcct gcagaccctg    960
gtgggtccgg gtgaggaaca caccaccctg gcgggtctgc cgaccgaagc cagcatccgc   1020
aacgccgtgg aagaggcgat cccaggcttc ctgcagaacg tgtacgccca caccgccggt   1080
ggcggtaagt tcctgggcat cctgcaggtc aagaagcgcc agccgagcga cgaaggccgt   1140
cagggccaag ccgccctgat cgccctggcc acctacagcg agctgaagaa catcatcctg   1200
gtggacgagg acgtggacat cttcgacagc gacgacatcc tgtgggccat gaccacccgc   1260
atgcagggcg acgtgagcat caccaccctg ccaggcatcc gtggccatca gctggacccg   1320
agccagagcc cagactacag caccagcatc cgtggcaacg gcatcagctg caagaccatc   1380
ttcgactgca ccgtgccgtg ggccctgaaa gcccgtttcg agcgtgcccc attcatggaa   1440
gtggacccga ccccgtgggc cccagagctg ttcagcgaca agaagtaa                1488
```

<210> SEQ ID NO 11
<211> LENGTH: 1473
<212> TYPE: DNA
<213> ORGANISM: Artificial Sequence
<220> FEATURE:
<223> OTHER INFORMATION: lpdC

<400> SEQUENCE: 11

```
atggcagaac aaccatggga tttgcgtcgc gtgcttgatg agatcaagga tgatccaaag     60
aactatcatg aaactgacgt cgaagttgat ccaaatgcgg aactttctgg tgtttatcgg    120
tatatcggtg ctggtgggac cgttcaacgg ccaacgcaag agggtccagc aatgatgttt    180
aacaacgtta aggggtttcc tgatacgcgg gtcttgactg gattgatggc gagtcgccgg    240
cgcgttggta agatgttcca ccacgattat cagacgttag ggcaatactt gaacgaagca    300
gtctctaatc cagtggcgcc agaaacggtt gctgaagcgg atgcgccagc tcacgatgtc    360
gtttataaag cgacggatga aggctttgat attcgtaagt tagtggcagc accaacgaat    420
acgccccaag atgctggacc atatattacg gtcggtgtgg tgtttggctc aagcatggac    480
aagtctaaga gtgatgtgac gattcaccga atggtccttg aagataagga taagttaggg    540
atttatatca tgcctggcgg tcggcacatt ggtgcgtttg cggaagagta tgagaaagct    600
aacaagccaa tgccaattac aattaatatt ggtttagatc cagccattac gattggtgca    660
actttcgaac caccgaccac gccattcggt tataacgaat taggtgttgc tggtgcgatt    720
cggaaccaag ctgttcaatt agttgacggg gtgaccgtcg atgaaaaggc gattgcgcgt    780
tctgaatata cgcttgaggg gtacattatg cctaacgaac gtattcagga agatatcaat    840
acgcatacgg gcaaggcgat gcctgaattt ccgggttatg atggtgacgc caacccagct    900
```

```
ttacaagtga ttaaggtgac ggcggtgact catcggaaga atgccatcat gcaaagcgtg    960

attggaccat ccgaagaaca tgtcagcatg gcgggcattc caactgaagc tagtatctta   1020

caattggtta accgtgccat tcctggtaaa gtgacgaatg tttataatcc gccggctggt   1080

ggtggtaagt tgatgaccat catgcagatt cacaaggata atgaagcgga tgaaggcatt   1140

caacggcaag ctgccttgct tgcgttctca gcctttaagg aattgaagac tgttatcctg   1200

gttgatgaag atgttgatat ttttgatatg aatgatgtga tttggacgat gaatacccgt   1260

ttccaagccg atcaggactt gatggtctta tcaggcatgc ggaatcatcc gttggaccca   1320

tcggaacgcc cacaatatga tccaaagtcg attcgtttcc gtgggatgag ttctaaacta   1380

gtgattgatg gcaccgtacc attcgatatg aaggaccaat ttgaacgggc ccaattcatg   1440

aaagtggctg actgggagaa gtatttgaag taa                               1473
```

<210> SEQ ID NO 12
<211> LENGTH: 261
<212> TYPE: DNA
<213> ORGANISM: Artificial Sequence
<220> FEATURE:
<223> OTHER INFORMATION: phK

<400> SEQUENCE: 12

```
atgacaactc aaccggaaac caaatccttt gaagagctga cccgatacat ccgagtgcgc     60

agtgagccgg gcgacaagtt cgtggaattc gacttcgcca ttgcttaccc cgagctcttc    120

gttgagctcg tgctgcctca cgaggccttc gagattttct gcaaacataa caaagtcgtc    180

cacatggact ccaacataat ccgcaaaatt gacgaagaca tggtcaagtg gcggttcgga    240

gagcatggca agcgctactg a                                              261
```

<210> SEQ ID NO 13
<211> LENGTH: 1002
<212> TYPE: DNA
<213> ORGANISM: Artificial Sequence
<220> FEATURE:
<223> OTHER INFORMATION: phL

<400> SEQUENCE: 13

```
atgagtattg aaatcaagac caattcggtg gaacctatcc gccatactta tggccacatc     60

gcccgtcgct tcggtgataa gccggctacc cgttatcagg aggccagcta cgacattgag    120

gcaaagacca atttccatta ccggccccag tgggattccg agcacaccct gaacgatccc    180

acgcgtaccg ccatccgcat ggaagactgg tgcgccgttt ccgatccccg ccagttttac    240

tatggcgcct atgtcggcaa ccgggccaag atgcaggagt cggccgagac cagctttggc    300

ttctgcgaaa agcgtaatct gctgacccgc ctttccgaag aaacccagaa gcaattgttg    360

cggctgctgg tgcccctgcg tcatgtcgag cttggcgcca acatgaacaa cgccaagatc    420

gccggtgatg ccaccgccac gaccgtctcc cagatgcaca tctacactgg gatggatcgc    480

ttgggcattg gccagtacct gtcccgtatt gcattgatga ttgatggcag caccggtgcc    540

gctctggatg agtccaaggc ctactggatg gatgacgaaa tgtggcaacc catgcgcaag    600

ctggtcgaag acacgcttgt ggtcgatgat tggtttgagc tgactctggt tcagaacatt    660

cttatcgacg gaatgatgta cccgctggtc tacgacaaga tggaccagtg gttcgaaagc    720

cagggtgctg aagatgtgtc catgctcacg gagttcatgc gtgactggta caaggaatcc    780

ctacgctgga ctaatgccat gatgaaagcc gtggccggtg aaagtgagac taaccgtgag    840
```

```
ttgcttcaaa aatggatcga tcactgggaa ccgcaggcct acgaagccct gaaacctctg    900

gccgaagcct ccgttggcat cgacgggctg aatgaagccc gggcggaact ctctgcccgc    960

ctgaagaaat tcgaactgca gagccgggga gtctcagcat ga                      1002
```

<210> SEQ ID NO 14
<211> LENGTH: 270
<212> TYPE: DNA
<213> ORGANISM: Artificial Sequence
<220> FEATURE:
<223> OTHER INFORMATION: phM

<400> SEQUENCE: 14

```
atgagccagc ttgtatttat tgtattccag gacaacgacg actcccgcta cctcgcggaa     60

gccgttatgg aagataaccc cgacgccgaa atgcagcacc agccggccat gatccggatc    120

caggcggaaa aacgtctggt gatcaaccgc gaaaccatgg aagaaaagct ggggcgagac    180

tgggatgttc aggaaatgct cataaatgtt atcagcatcg ccggcaacgt cgatgaagac    240

gatgatcact tcattcttga atggaattaa                                     270
```

<210> SEQ ID NO 15
<211> LENGTH: 1536
<212> TYPE: DNA
<213> ORGANISM: Artificial Sequence
<220> FEATURE:
<223> OTHER INFORMATION: phN

<400> SEQUENCE: 15

```
atggttagta aaaacaaaaa gcttaacctt aaagacaagt atcaatacct gacccgggat     60

atggcctggg aaccgaccta tcaggacaag aaagatattt ttccggagga ggattttgag    120

ggtatcaaga tcaccgactg gtcccagtgg gaagatccgt tccgcctgac catggatgcc    180

tactggaaat accaggcgga aaaagagaag aagctgtacg ccattttcga tgcatttgcc    240

cagaacaacg gccaccagaa catttcagac gcccgttatg tgaacgcgct aaaactgttc    300

atcagtggta tatctccgct tgaacatgcg gcgttccagg gttattccaa ggtcggtcgc    360

cagtttagcg gcgccggggc gcgggttgcc tgccagatgc aggcaattga cgagctgcgt    420

cattcccaga cccagcaaca cgcgatgagc cactacaaca agcacttcaa cggtctgcac    480

gatggcccgc acatgcacga tcgggtgtgg tacctgtcgg tgccgaaatc gttctttgat    540

gatgcacgct cggctggtcc gttcgagttc ctgacggcca tctcattctc gttcgagtat    600

gtgctcacca acctgttgtt cgtaccgttc atgtcgggcg ctgcctataa cggcgacatg    660

gcgacagtca ccttcggttt ctccgcccag tctgacgaag cccgtcatat gaccctgggc    720

cttgaggtga tcaagttcat cctcgagcag cacgaagata acgtgcccat cgttcagcgc    780

tggatcgaca agtggttctg gcgcggattt cgcctgctta gcctggtcag catgatgatg    840

gactacatgc tgccaaacaa ggtcatgtcc tggtccgagg catgggaagt ctattacgag    900

cagaacggcg gtgctctgtt caaggacctg gagcgatacg gcatccgccc gcccaaatac    960

caggacgtgg ctaacgatgc caaacatcac ctgagccacc agctttggac cactttctac   1020

cagtactgcc aggccaccaa cttccatact tggattccgg agaaggaaga gatggactgg   1080

atgtccgaga agtatccgga cactttcgac aagtactacc gtccgcgtta cgagtacctg   1140

gcgaaagagg ctgccgctgg ccgtcgcttc tacaacaaca ccctgccgca gctgtgccaa   1200

gtgtgtcaga tcccgaccat tttcaccgag aaagatgccc caaccatgct cagccatcgg   1260

cagatagaac atgagggcga acgctatcac ttctgctctg acggctgctg cgacatcttc   1320
```

aaacacgagc cggagaagta catacaggcc tggctgccgg tgcaccagat ctaccagggc 1380
aactgtgaag gcggggatct cgagaccgtg gtgcagaagt attaccacat caatatcgga 1440
gaggacaatt tcgactacgt tggatcgccc gaccagaaac actggctgtc gatcaagggc 1500
cggaagcctg cagacaagaa ccaggacgcc gcctga 1536

<210> SEQ ID NO 16
<211> LENGTH: 360
<212> TYPE: DNA
<213> ORGANISM: Artificial Sequence
<220> FEATURE:
<223> OTHER INFORMATION: phO

<400> SEQUENCE: 16
atgagtgtaa acgcacttta cgactacaag tttgaaccta aagacaaggt cgagaacttc 60
cacggcatgc agctgctgta tgtctactgg cccgatcacc tgctgttctg cgcgcccttc 120
gcgctgctgg tgcagccggg tatgaccttc agtgccctgg tggacgagat tctcaagccg 180
gctaccgccg cgcacccgga ctctgccaag gcggacttcc tgaatgccga gtggttgctg 240
aacgatgaac cgttcacacc caaggctgac gccagcctga aagagcaggg tattgatcac 300
aagagcatgc tgacggtgac cacgccgggc ctgaagggca tggcgaacgc cggttactga 360

<210> SEQ ID NO 17
<211> LENGTH: 1062
<212> TYPE: DNA
<213> ORGANISM: Artificial Sequence
<220> FEATURE:
<223> OTHER INFORMATION: phP

<400> SEQUENCE: 17
atgagttaca ccgtcactat tgagccgatc ggcgagcaga ttgaggtaga ggatggccag 60
actatcctcg ccgccgccct gcgccagggt gtctggctgc cctttgcctg cggccacggc 120
acctgtgcta cctgtaaggt tcaggtgctt gaaggtgatg tcgagatcgg aaacgcctcg 180
ccctttgcgc tgatggatat cgaacgtgac gagggcaagg ttctggcctg ctgcgccacg 240
gttgagagcg acgtcaccat tgaggtggac atcgatgtgg atccggattt tgagggctac 300
ccggtggagg actatgccgc catagcgacc gatatcgtcg aactctctcc gaccatcaag 360
ggcattcacc tgaaactgga ccggccgatg acattccagg ccggccagta catcaatatc 420
gaactgccgg gtgttgaagg cgcgagggcc ttctccctgg ccaacccgcc cagcaaagca 480
gacgaagtgg agctgcatgt gcgcctcgtt gagggcggtg ctgccaccac ctacatccac 540
gaacaactga aaacgggtga tgcgctgaac ctttcaggcc cttacggcca gttcttcgtg 600
cgtagttccc aacccggcga tctgattttc atcgccggcg gatccggatt gtccagtccc 660
cagtcgatga tccttgatct gcttgagcag aacgatgagc gcaagatcgt tctgttccag 720
ggtgcccgaa acctggcaga gctttacaac cgggagctgt ttgaggctct ggatcgcgac 780
cacgacaatt tcacctacgt accggcgctt agccaagccg acgaagaccc tgactggaag 840
ggcttccgag gctatgtcca tgaggcggcc aacgcccatt tcgatggccg gtttgccggt 900
aacaaggcat acctgtgcgg cccgcctcca atgatcgatg cggctatcac ggcattgatg 960
caggggcggc tgttcgagcg tgacatcttc atggagaaat tcctgacagc ggcggacgga 1020
gctgaagaca cccagcgttc ggccctgttc aagaagatat ag 1062

<210> SEQ ID NO 18

<211> LENGTH: 309
<212> TYPE: DNA
<213> ORGANISM: Artificial Sequence
<220> FEATURE:
<223> OTHER INFORMATION: phQ

<400> SEQUENCE: 18

```
atgggcatgg gtttcctagt gttcaaccgc acaacgggag gtcactttac ctgccaggag     60

ggccagagtg tgctcaaggc catggagcag aggggcctga agtgtgtccc cgtgggctgc    120

cggggtggtg gttgcggatt ttgtaagatc cgggttctgg aagggtattt cgagtgcggc    180

aagatgagca agcggcacgc cccgcctgaa gccgttgaaa aaggggaagt tctggcctgc    240

cggatctacc cactgactga tctgatcatt gagtgtccgc cgcaaccggc ggcggacttt    300

gcgagctag                                                            309
```

<210> SEQ ID NO 19
<211> LENGTH: 936
<212> TYPE: DNA
<213> ORGANISM: Artificial Sequence
<220> FEATURE:
<223> OTHER INFORMATION: catA

<400> SEQUENCE: 19

```
atgaccgtga aaatttccca cactgccgac attcaagcct tcttcaaccg ggtagctggc     60

ctggaccatg ccgaaggaaa cccgcgcttc aagcagatca ttctgcgcgt gctgcaagac    120

accgcccgcc tgatcgaaga cctggagatt accgaggacg agttctggca cgccgtcgac    180

tacctcaacc gcctgggcgg ccgtaacgag gcaggcctgc tggctgctgg cctgggtatc    240

gagcacttcc tcgacctgct gcaggatgcc aaggatgccg aagccggcct tggcggcggc    300

accccgcgca ccatcgaagg cccgttgtac gttgccgggg cgccgctggc ccagggcgaa    360

gcgcgcatgg acgacggcac tgacccaggc gtggtgatgt tccttcaggg ccaggtgttc    420

gatgccgacg gcaagccgtt ggccggtgcc accgtcgacc tgtggcacgc caatacccag    480

ggcacctatt cgtacttcga ttcgacccag tccgagttca acctgcgtcg gcgtatcatc    540

accgatgccg agggccgcta ccgcgcgcgc tcgatcgtgc cgtccgggta tggctgcgac    600

ccgcagggcc caacccagga atgcctggac ctgctcggcc gccacggcca gcgcccggcg    660

cacgtgcact tcttcatctc ggcaccgggg caccgccacc tgaccacgca gatcaacttt    720

gctggcgaca agtacctgtg ggacgacttt gcctatgcca cccgcgacgg gctgatcggc    780

gaactgcgtt ttgtcgagga tgcggcggcg gcgcgcgacc gcggtgtgca aggcgagcgc    840

tttgccgagc tgtcattcga cttccgcttg cagggtgcca agtcgcctga cgccgaggcg    900

cgaagccatc ggccgcgggc gttgcaggag ggctga                               936
```

<210> SEQ ID NO 20
<211> LENGTH: 47
<212> TYPE: DNA
<213> ORGANISM: Artificial Sequence
<220> FEATURE:
<223> OTHER INFORMATION: pKE112-HsOMT-F(forward)

<400> SEQUENCE: 20

```
ggtacctttc acacaggaaa cagaccatgg gcgataccaa agaacag                  47
```

<210> SEQ ID NO 21
<211> LENGTH: 27
<212> TYPE: DNA
<213> ORGANISM: Artificial Sequence
<220> FEATURE:
<223> OTHER INFORMATION: pKE112-HsOMT-R(reverse)

<400> SEQUENCE: 21
ggatccttaa gttacggacc tgcttcg 27

<210> SEQ ID NO 22
<211> LENGTH: 67
<212> TYPE: DNA
<213> ORGANISM: Artificial Sequence
<220> FEATURE:
<223> OTHER INFORMATION: pKE112-HsOMTHis-F(forward)

<400> SEQUENCE: 22
ggtacctttc acacaggaaa cagaccatgc atcaccatca ccatcatggc gataccaaag 60
aacagcg 67

<210> SEQ ID NO 23
<211> LENGTH: 27
<212> TYPE: DNA
<213> ORGANISM: Artificial Sequence
<220> FEATURE:
<223> OTHER INFORMATION: pKE112- HsOMTHis -R(reverse)

<400> SEQUENCE: 23
ggatccttaa gttacggacc tgcttcg 27

<210> SEQ ID NO 24
<211> LENGTH: 44
<212> TYPE: DNA
<213> ORGANISM: Artificial Sequence
<220> FEATURE:
<223> OTHER INFORMATION: pET28a- HsOMTHis -F(forward)

<400> SEQUENCE: 24
catatgcatc accatcacca tcatggcgat accaaagaac agcg 44

<210> SEQ ID NO 25
<211> LENGTH: 27
<212> TYPE: DNA
<213> ORGANISM: Artificial Sequence
<220> FEATURE:
<223> OTHER INFORMATION: pET28a- HsOMTHis -R(reverse)

<400> SEQUENCE: 25
ctcgagttaa gttacggacc tgcttcg 27

<210> SEQ ID NO 26
<211> LENGTH: 28
<212> TYPE: DNA
<213> ORGANISM: Artificial Sequence
<220> FEATURE:
<223> OTHER INFORMATION: pET28a-PobA-F(forward)

<400> SEQUENCE: 26
catatgaaaa ctcaggttgc aattattg 28

<210> SEQ ID NO 27
<211> LENGTH: 26
<212> TYPE: DNA
<213> ORGANISM: Artificial Sequence
<220> FEATURE:
<223> OTHER INFORMATION: pET28a-PobA-R(reverse)

<400> SEQUENCE: 27
ctcgagtcag gcaacttcct cgaacg 26

<210> SEQ ID NO 28
<211> LENGTH: 53
<212> TYPE: DNA
<213> ORGANISM: Artificial Sequence
<220> FEATURE:
<223> OTHER INFORMATION: pKE112-PobA-F(forward)

<400> SEQUENCE: 28
cctgcaggtt tcacacagga aacagaccat gaaaactcag gttgcaatta ttg 53

<210> SEQ ID NO 29
<211> LENGTH: 26
<212> TYPE: DNA
<213> ORGANISM: Artificial Sequence
<220> FEATURE:
<223> OTHER INFORMATION: pKE112-PobA-R(reverse)

<400> SEQUENCE: 29
aagctttcag gcaacttcct cgaacg 26

<210> SEQ ID NO 30
<211> LENGTH: 25
<212> TYPE: DNA
<213> ORGANISM: Artificial Sequence
<220> FEATURE:
<223> OTHER INFORMATION: pET28a-LpdC-F(forward)

<400> SEQUENCE: 30
catatggcag aacaaccatg ggatt 25

<210> SEQ ID NO 31
<211> LENGTH: 30
<212> TYPE: DNA
<213> ORGANISM: Artificial Sequence
<220> FEATURE:
<223> OTHER INFORMATION: pET28a-LpdC-R(reverse)

<400> SEQUENCE: 31
ctcgagttac ttcaaatact tctcccagtc 30

<210> SEQ ID NO 32
<211> LENGTH: 24
<212> TYPE: DNA
<213> ORGANISM: Artificial Sequence
<220> FEATURE:
<223> OTHER INFORMATION: pET28a-AroY-F(forward)

<400> SEQUENCE: 32
catatgcaga acccgatcaa cgac 24

<210> SEQ ID NO 33
<211> LENGTH: 28
<212> TYPE: DNA
<213> ORGANISM: Artificial Sequence
<220> FEATURE:
<223> OTHER INFORMATION: pET28a-AroY-R(reverse)

<400> SEQUENCE: 33
ctcgagttac ttcttgtcgc tgaacagc 28

<210> SEQ ID NO 34
<211> LENGTH: 49
<212> TYPE: DNA
<213> ORGANISM: Artificial Sequence -continued

```
<220> FEATURE:
<223> OTHER INFORMATION: pKE112-CatA-F(forward)

<400> SEQUENCE: 34

ggtacctttc acacaggaaa cagaccatga ccgtgaaaat ttcccacac               49


<210> SEQ ID NO 35
<211> LENGTH: 24
<212> TYPE: DNA
<213> ORGANISM: Artificial Sequence
<220> FEATURE:
<223> OTHER INFORMATION: pKE112-CatA-R(reverse)

<400> SEQUENCE: 35

ggatcctcag ccctcctgca acgc                                          24
```